(12) United States Patent
Massaro et al.

(10) Patent No.: US 12,114,647 B2
(45) Date of Patent: Oct. 15, 2024

(54) DEVICES, SYSTEMS, AND METHODS FOR TRANSPORTING LIVE INSECTS

(71) Applicant: Verily Life Sciences LLC, South San Francisco, CA (US)

(72) Inventors: Peter Massaro, San Carlos, CA (US); Charles Behling, Brisbane, CA (US); Brian Wasson, Columbus, OH (US)

(73) Assignee: Verily Life Sciences LLC, Dallas, TX (US)

( * ) Notice: Subject to any disclaimer, the term of this patent is extended or adjusted under 35 U.S.C. 154(b) by 98 days.

(21) Appl. No.: 17/447,585

(22) Filed: Sep. 14, 2021

(65) Prior Publication Data

US 2022/0079126 A1 Mar. 17, 2022

Related U.S. Application Data

(60) Provisional application No. 62/706,845, filed on Sep. 14, 2020.

(51) Int. Cl.
*A01K 67/033* (2006.01)
*B65B 31/00* (2006.01)
(Continued)

(52) U.S. Cl.
CPC ............ *A01K 67/033* (2013.01); *B65B 31/00* (2013.01); *B65D 81/2084* (2013.01);
(Continued)

(58) Field of Classification Search
CPC .. A01K 67/033; B65B 31/00; B65D 81/2084; B65D 81/3825; B65D 85/50
See application file for complete search history.

(56) References Cited

U.S. PATENT DOCUMENTS 3,375,808 A   4/1968  Freeman
3,468,289 A * 9/1969  Daniel ................. B65D 81/266
                                                       119/6.5
(Continued)

FOREIGN PATENT DOCUMENTS

CN      107672905 A  *  2/2018

OTHER PUBLICATIONS

International Application No. PCT/US2021/050281, International Search Report and the Written Opinion, Mailed On Feb. 4, 2022, 13 pages.

(Continued)

*Primary Examiner* — Monica L Perry
*Assistant Examiner* — Aaron M Rodziwicz
(74) *Attorney, Agent, or Firm* — Kilpatrick Townsend & Stockton LLP

(57) ABSTRACT

An insect container for transportation of live insects including a first and second container portion. The first and second container portions are configured to be coupled together to enclose a volume. Each of the first and second container portions include a backing plate defining a set of vent holes. The backing plate is rotatable when the insect container is in an open configuration. Each of the first and second container portions include a wall defining a container perimeter and including a non-rotating coupling feature, in which the backing plate and the wall together define a cavity. The non-rotating coupling features of the first and second container portions enable the container portions to couple together to fully enclose a volume to prevent relative rotation of the first and second container portions.

18 Claims, 25 Drawing Sheets

(51) Int. Cl.
  *B65D 81/20* (2006.01)
  *B65D 81/38* (2006.01)
  *B65D 85/50* (2006.01)

(52) U.S. Cl.
  CPC ......... *B65D 81/3825* (2013.01); *B65D 85/50* (2013.01); *B65B 2220/16* (2013.01)

(56) References Cited

U.S. PATENT DOCUMENTS

| | | | | |
|---|---|---|---|---|
| 3,855,727 | A * | 12/1974 | Canoy | A01M 1/106 43/65 |
| 4,212,267 | A * | 7/1980 | Patterson | A01K 1/031 119/6.5 |
| 4,334,498 | A | 6/1982 | Bedding | |
| 5,031,573 | A * | 7/1991 | De Marco | A01K 1/0245 206/429 |
| 5,398,642 | A * | 3/1995 | Harwich | A01K 67/033 119/6.5 |
| 5,586,406 | A * | 12/1996 | Lin | A01K 97/04 43/56 |
| 5,630,374 | A * | 5/1997 | Cunningham | A01K 97/04 119/6.5 |
| 5,895,310 | A * | 4/1999 | Otomo | A01K 67/033 449/20 |
| 6,561,125 | B1 * | 5/2003 | Lohsomboon | A01K 67/033 119/6.5 |
| 2003/0070348 | A1 * | 4/2003 | Spragins | A01M 1/026 43/121 |
| 2006/0266292 | A1 * | 11/2006 | Duckworth | A01K 1/0245 119/6.5 |
| 2010/0043276 | A1 | 2/2010 | Eget, Jr. et al. | |
| 2014/0295733 | A1 | 10/2014 | Waite et al. | |

OTHER PUBLICATIONS

PCT/US2021/050281, "Invitation to Pay Additional Fees and, Where Applicable, Protest Fee", Nov. 24, 2021, 2 pages.

\* cited by examiner

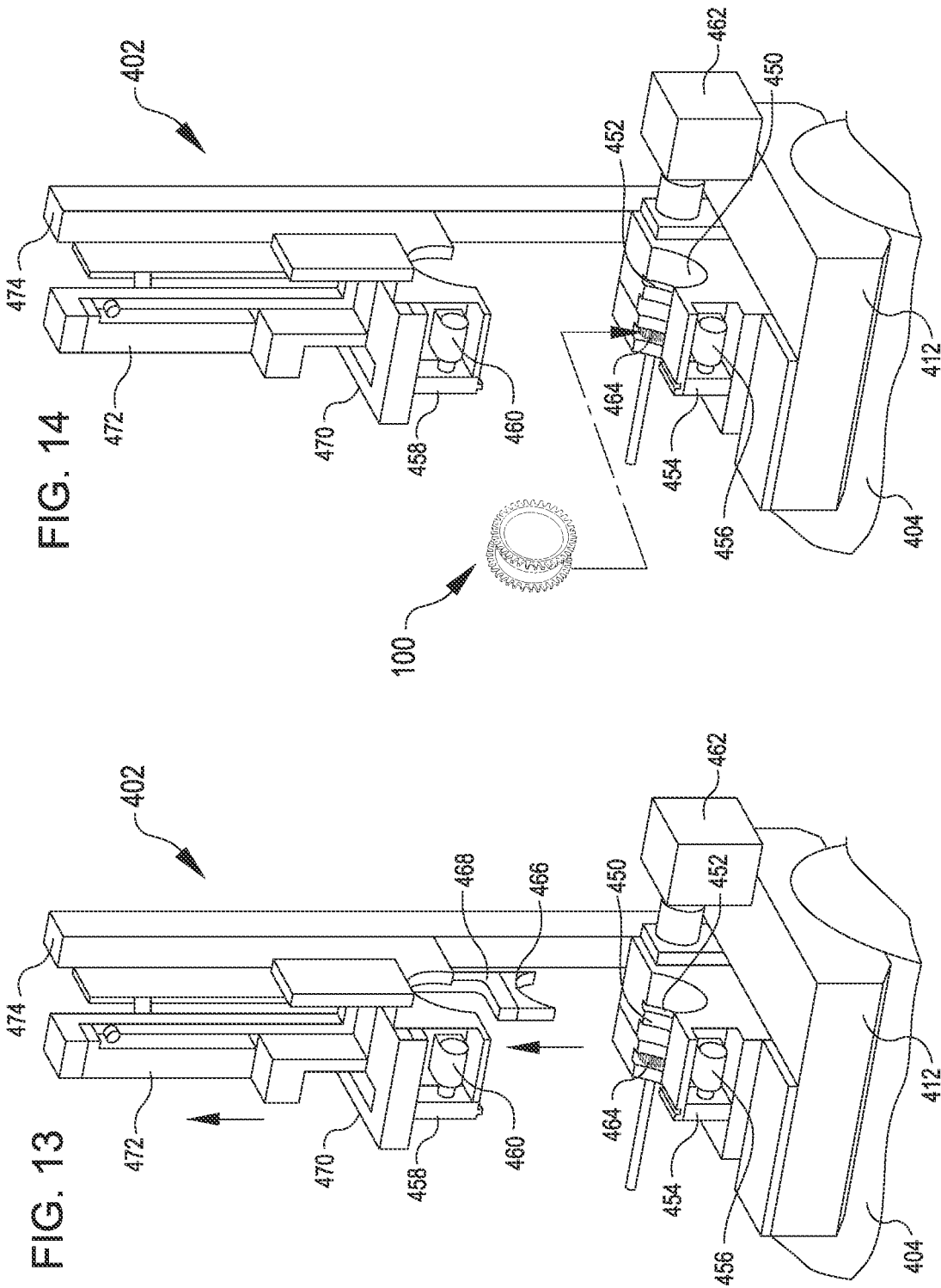

DEVICES, SYSTEMS, AND METHODS FOR TRANSPORTING LIVE INSECTS

CROSS-REFERENCE TO RELATED APPLICATIONS

This application claims priority to U.S. Provisional Patent Application No. 62/706,845, filed Sep. 14, 2020, titled "Devices, Systems, And Methods For Transporting Live Insects," the entirety of which is hereby incorporated by reference.

BACKGROUND

Many Sterile Insect Technique (SIT) programs require processing insects and moving insects between various locations for processing, distribution, and release. During some transfer processes, insects may escape or be damaged while moving between locations. It is important to transport and deliver insects for SIT programs in the best condition possible for the program to be as successful as possible.

SUMMARY

Various examples are described including systems, methods, and devices relating to transportation of live insects.

One general aspect includes an insect transportation container, including a first container portion and a second container portion, the first container portion configured to be coupled to the second container portion to enclose a volume. Each of the first and second container portions includes a backing plate having an engaging surface at a perimeter of the backing plate. The respective engaging surface of each container portion defines a set of protrusions extending in a plane defined by the backing plate radially away from a center of the backing plate. The respective backing plate of each container portion also defines a plurality of vent holes providing a conduit for air to travel through the backing plate to provide air to insects stored in the insect container. The respective backing plate of each container portion is also rotatable about a respective axis of rotation perpendicular to the backing plate when engaged with a rotating mechanism at the respective engaging surface to rotate the respective first or second container portion to agitate insects to fall from the respective first or second container portion when the insect transportation container is in an open configuration. The insect transportation container also includes a wall extending from a first surface of the respective backing plate in a direction parallel to the respective axis of rotation, the wall defining a container perimeter and including a non-rotating coupling feature at a distal end of the wall from the backing plate, where the backing plate and the wall together define a cavity, and where the non-rotating coupling feature of the first container portion and the non-rotating coupling feature of the second container portion enable the first and second container portions to couple together to fully enclose a volume including the cavity and prevent relative rotation of the first and second container portions to prevent damage to insects stored therein.

Another general aspect includes an insect transportation container, including a first container portion. The first container portion includes a first circular backing plate having teeth formed around a perimeter thereof. The first container portion also includes a first raised wall extending from a first surface of the first circular backing plate, an edge of the first raised wall opposite the first circular backing plate including a first profile. The insect transportation container includes a second container portion. The second container portion also includes a second circular backing plate having teeth formed around a perimeter thereof and a second raised wall extending from a first surface of the second circular backing plate, an edge of the second raised wall opposite the second backing plate including a second profile, where the first profile and the second profile mate together to releasably interlock the first container portion and the second container portion. The first profile and the second profile mate together and also prevent rotation of the first container portion with respect to the second container portion. The first container portion and the second container portion define an interior volume configured to receive a population of insects when interlocked with each other.

Another general aspect includes a system for loading insect transportation containers, including a trough with a bottom and walls defining a volume to receive a plurality insect transportation containers for loading. The system also includes an insect dispenser maintained in a position adjacent an upper opening of the trough and defining a gas port and an insect port in a wall thereof, the insect port selectively openable to enable loading and unloading of insects into the insect transportation container. The system also includes an insect transportation container positionable within the volume to retain insects during transportation, the insect transportation container sized to receive insects from the insect dispenser through the insect port in a compact volume after cooling within the insect dispenser. The system also includes a gas system including a conduit coupled to gas port of the insect dispenser to direct gas into the insect dispenser through the gas port. The system also includes a refrigeration system positioned to cool the trough.

Another general aspect includes a method for loading insect transportation containers including filling an insect dispenser with a plurality of insects, the insects in a first state. The method also includes cooling a trough to decrease a temperature within the trough below an ambient temperature. The method further includes connecting the insect dispenser to a gas system positioned adjacent the trough. The method also includes directing gas into the insect dispenser, the gas affecting the insects within the insect dispenser such that the insects transition to a second state. The method also includes positioning an insect transportation container adjacent to a loading port of the insect dispenser within the trough. The method further includes opening the loading port of the insect dispenser to release the insects in the second state into the insect transportation container. The method also includes sealing the insect transportation container. Other embodiments of this aspect include corresponding devices and systems each configured to perform the actions of the methods.

Another general aspect includes an insect transportation packaging system, including an insulated shipping container including a shipping box with insulation lining interior surfaces of the shipping box. The insect transportation packaging system also includes a pressure vessel removable from the insulated shipping container, the pressure vessel including a chamber body and a lid coupleable together to seal a volume within the pressure vessel. The insect transportation packaging system also includes a removable tray with recesses shaped to receive insect transportation containers and to maintain the insect transportation containers in place within the pressure vessel. The insect transportation packaging system also includes an environment management system for detecting and controlling environmental conditions within the pressure vessel during transportation.

One general aspect includes an insect transportation packaging system including an insulated shipping container including a shipping box with insulation lining interior surfaces of the shipping box. The insect transportation packaging system also includes a pressure vessel removable from the insulated shipping container, the pressure vessel including a chamber body and a lid coupleable together to seal a volume within the pressure vessel. The system also includes an environment management system including environment sensors to detect environmental conditions within the volume and environment adjusters to alter the environmental conditions within the volume in response to information from the environment sensors. The insect transportation packaging system also includes a plurality of trays having a perimeter corresponding to an interior of the pressure vessel, individual trays of the plurality of trays having semi-cylindrical recesses to receive insect transportation containers and to maintain the insect transportation containers in place within the pressure vessel, the plurality of trays configured to stack on one another in layers within the pressure vessel.

One general aspect includes a method of packaging insects for transportation including providing a shipping box, the shipping box lined with insulation on all inner surfaces of the shipping box. The method of packaging insects also includes providing a pressure vessel capable of maintaining an internal pressure against varying external pressures. The method also includes placing the pressure vessel within the shipping box. The method further includes placing a container tray in an interior of the pressure vessel, the container tray including recesses shaped to receive a plurality of insect containers and placing one or more insect transportation containers into the recesses of the container tray. The method of packaging insects also includes activating an environment monitoring system within the pressure vessel. The method of packaging insects also includes sealing the pressure vessel. The method further includes closing the shipping box around the pressure vessel. Other embodiments of this aspect include corresponding devices and systems each configured to perform the actions of the methods.

One general aspect includes a carbon dioxide scrubbing system for insect transportation within a pressure vessel including a porous container allowing free exchange of fluid from an interior to an exterior of the porous container and vice versa, the porous container positioned inside the pressure vessel. The carbon dioxide scrubbing system also includes a carbon dioxide scrubbing compound contained within the porous container. The carbon dioxide scrubbing system also includes a gas reservoir tank, the gas reservoir tank filled with a pressurized mixture of oxygen and carbon dioxide. The carbon dioxide scrubbing system also includes a pressure regulator coupled in-line between the gas reservoir tank and the pressure vessel.

Another general aspect includes a method for scrubbing carbon dioxide within a pressure vessel for insect transportation including providing a pressure vessel to contain insects during transportation at a controlled temperature and pressure. The method also includes providing a carbon dioxide scrubbing compound within the pressure vessel. The method further includes coupling a gas reservoir to the pressure vessel via a gas regulator, the gas reservoir including a mixture of carbon dioxide and oxygen and the gas regulator configured to introduce gas from the gas reservoir into the pressure vessel in response to a pressure within the pressure vessel dropping below a predetermined threshold.

Other embodiments of this aspect include corresponding devices and systems each configured to perform the actions of the methods.

Another general aspect includes a carbon dioxide scrubbing system for insect transportation within a pressure vessel including a porous container allowing free exchange of fluid from an interior to an exterior of the porous container and vice versa, the porous container positioned inside the pressure vessel. The carbon dioxide scrubbing system also includes a carbon dioxide scrubbing compound contained within the porous container. The carbon dioxide scrubbing system also includes a reservoir of hydrogen peroxide and a reaction catalyst. The carbon dioxide scrubbing system also includes a metering system coupled to the reservoir of hydrogen peroxide to control a flow rate of hydrogen peroxide from the reservoir to the reaction catalyst. Other embodiments of this aspect include corresponding devices and systems each configured to perform the actions of the methods.

Another general aspect includes a method for scrubbing carbon dioxide within a pressure vessel for insect transportation including providing a pressure vessel to contain insects during transportation at a controlled temperature and pressure. The method also includes providing a carbon dioxide scrubbing compound within the pressure vessel and providing an oxygen generation system within the pressure vessel. The method also includes controlling a metering system of the oxygen generation system to produce oxygen within the pressure vessel to maintain an oxygen level within the pressure vessel as insects consume oxygen. Other embodiments of this aspect include corresponding devices and systems each configured to perform the actions of the methods.

One general aspect includes an insect transportation container unloading system including an insect receiving chamber defining an insect loading opening and an insect transportation container unloader coupled to the insect receiving chamber to unload insects from insect transportation containers into the insect receiving chamber through the insect loading opening. The insect transportation container unloader includes an insect transportation container dock defining a recess for receiving an insect transportation container and an opening corresponding to the insect loading opening through which insects are loaded into the insect receiving chamber. The insect transportation container unloader also includes a securing gate coupled to an actuator, the actuator positioned to position the securing gate in a securing position where the insect transportation container is retained within the insect transportation container dock and in a free position where the insect transportation container is not retained within the insect transportation container dock. The insect transportation container unloader also includes a clamp coupled to an opening actuator, the opening actuator and clamp positionable to selectively open and close the insect transportation container within the insect transportation container dock. The insect transportation container unloader also includes an agitation device configured to agitate insect transportation containers positioned within the insect transportation container dock and a gate coupled to a gate actuator, the gate positionable by the gate actuator in a first position where the gate seals the insect loading opening and a second position where the gate does not seal the insect loading opening.

Another general aspect includes an insect transportation container unloading system including an insect receiving chamber defining an insect loading opening and an insect transportation container unloader coupled to the insect receiving chamber to unload insects from insect transportation containers into the insect receiving chamber through the insect loading opening. The insect transportation container unloader includes an insect transportation container dock defining a recess for receiving an insect transportation container and an opening corresponding to the insect loading opening through which insects are loaded into the insect receiving chamber. The insect transportation container unloader also includes an opening actuator, the opening actuator and positionable to selectively open and close the insect transportation container within the insect transportation container dock. The insect transportation container unloader also includes an insect directing system that causes the insects to travel through the insect loading opening after the insect transportation container is opened within the insect transportation container dock.

Another general aspect includes a method for unloading insect transportation containers including positioning an insect transportation container in a dock of an insect transportation container unloading system. The method also includes positioning a securing gate in contact with the dock to secure the insect transportation container in the dock and separating a first portion and a second portion of the insect transportation container. The method also includes agitating the insect transportation container to release insects from an interior volume of the insect transportation container through an opening in the dock. The method further includes positioning a securing gate to close the opening of the dock and coupling the first portion and the second portion of the insect transportation container. The method also includes positioning the securing gate in an open position to enable removal of the insect transportation container. Other embodiments of this aspect include corresponding devices and systems each configured to perform the actions of the methods.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIG. 13 illustrates a step in a process of unpacking insects from an insect transportation container using the unpacking device of FIG. 12, according to at least some examples.

FIG. 14 illustrates a step in a process of unpacking insects from an insect transportation container using the unpacking device of FIG. 12, according to at least some examples.

DETAILED DESCRIPTION

Figure 1:
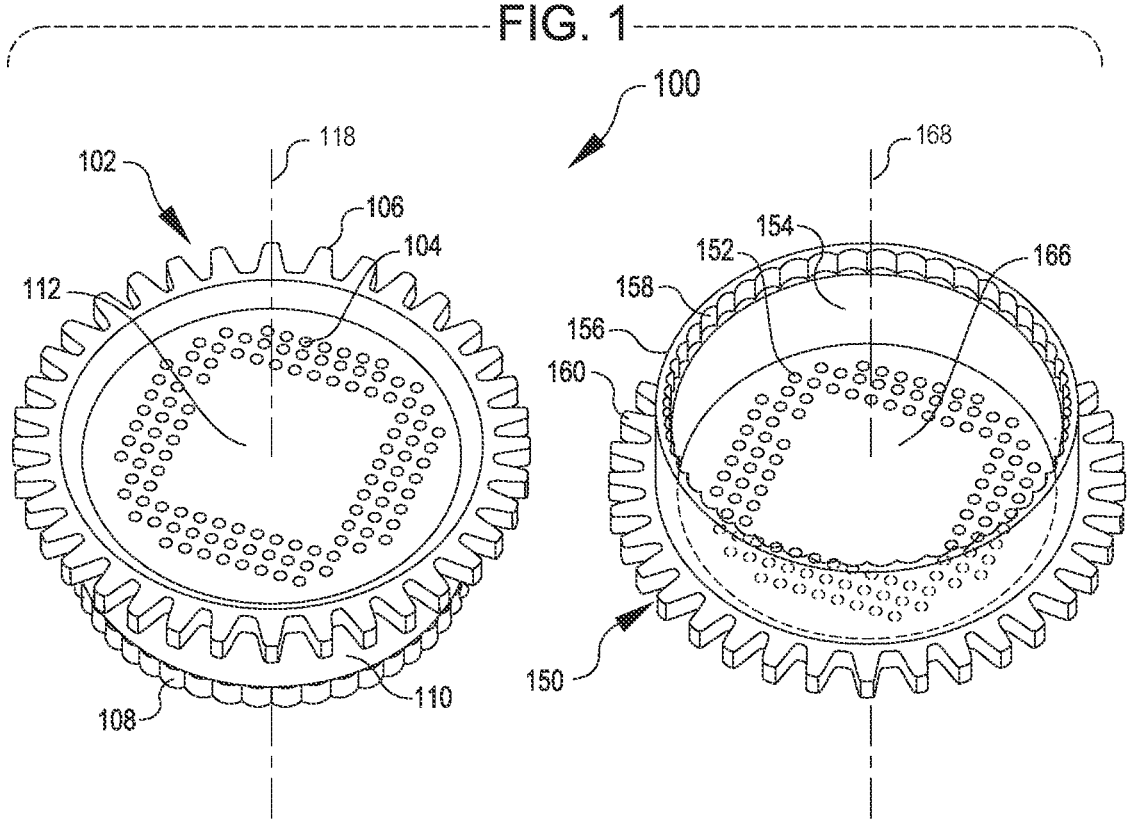
FIG. 1 illustrates an insect transportation container, according to at least some examples.

Examples are described herein in the context of transporting live adult mosquitoes. Those of ordinary skill in the art will realize that the following description is illustrative only and is not intended to be in any way limiting. For example, the techniques described herein may be used to transport other live insects and/or other creatures for various purposes not limited to SIT programs. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Live insects such as adult mosquitoes as part of an SIT program may be reared at a facility remote from a release location for the program. The live insects must be able to survive transit and arrive at the release location intact and undamaged. In addition, the live insects are intended to be released only at the final release location as part of the SIT program and should be controlled and not allowed to escape during any part of the transportation process. The systems and methods described herein provide efficient transportation for live insects while ensuring the insects arrive undamaged and intact while also preventing accidental or unintentional release. Furthermore, during transportation it is advantageous to maintain the insects in a dormant state such that the insects can be packed into a relatively small volume and can readily survive transportation. To achieve these and other purposes, described herein is an insect loading system for loading insects into insect transportation containers, the insect transportation containers useful for retaining insects during transportation, an insect transportation packaging system that receives and retains multiple insect transportations containers, a carbon dioxide scrubbing device for use in the insect transportation packaging system, and an unpacking system for unpacking the insects from the insect transportation containers.

Beginning with an illustrative example of the insect loading system a support system that includes one or more insect dispensers, the insect dispensers each include insect loading ports and air ports. Insects are moved into the insect dispensers via that insect loading ports, while the air ports allow refrigerated air or gas to be forced into the insect container to cause any insects within the insect containers to enter a dormant state. The insect dispensers may be initially filled with insects as they are raised or as part of a rearing system. The refrigerated air or gas is directed into the insect container through a gas conduit. Insect transportation containers are then positioned adjacent the insect loading port such that insects can be loaded after transitioning into a dormant state. The insect loading system may rest within a cooled chamber, such as a refrigerated trough, such that the insects are maintained in the dormant state.

In an illustrative example of the insect transportation container, the insect transportation container includes a two-part container that couples together to enclose a volume where insects are stored for transportation. The two-part container couples together such that the two parts are rotationally locked with respect to one another. The rotation lock prevents damage to insects stored therein. The insect transportation container has openings that allow air to pass from an outside to an inside of the container. Additionally, the insect transportation container includes an engaging surface around the perimeter of each of the two parts that allows an unloading device to agitate the insect transportation container and cause insects to fall out of the insect transportation container when open. Once the insects are put into the dormant state, they fit within a compact volume, much more compact than a volume of active insects. The insects can then be directed out of a loading port of the insect dispenser into an insect transportation container. The insect transportation container includes cushioning to protect the insects as they fall into the insect transportation container and during transport.

In an illustrative example of the transportation packaging system, the transportation packaging system includes an external box, an insulation layer, a pressure device, and an environment regulation system. The external box contains other elements of the system for shipping. The insulation layer resists heat transfer from a surrounding environment into the pressure device, or from the pressure device to the surrounding environment. The pressure device is a vessel capable of maintaining a constant internal pressure against a varying external pressure. The environment regulation system may regulate or maintain an oxygen level, a carbon dioxide level, a humidity level, a temperature, or other environmental condition within the pressure device to provide a safe, stable environment for the insects. The insect transportation container containing insects, along with other insect transportation containers are fit within a shaped recess of a tray that fits within a pressure vessel having an openable lid. The tray with the insect transportation containers is placed within the pressure vessel. The pressure vessel is designed to withstand a pressure differential between an interior and exterior of the pressure vessel.

In an illustrative example of the carbon dioxide scrubber, the carbon dioxide scrubber removes carbon dioxide from the environment and an oxygen generation system introduces or maintains oxygen levels within the pressure device. Within the pressure vessel there is a carbon dioxide scrubber that scrubs carbon dioxide produced by the insects while the oxygen generation system ensures a fresh supply of oxygen is available for the insects throughout transportation. In an example passive carbon dioxide scrubber, a container or package having an air-permeable enclosure is placed within the pressure device. The air-permeable enclosure may have a fine mesh, weave, or holes therein to allow transfer of air through the enclosure but to retain particles within the enclosure. The air-permeable enclosure of the carbon dioxide scrubbing device may include a soda lime substance or other scrubbing substance that removes carbon dioxide from the environment. The carbon dioxide scrubber is placed within or connected to the pressure vessel and the pressure vessel is closed. The an oxygen generation system may include a pressure tank coupled to the pressure device through a pressure regulator or generate oxygen through the use of metered reactants. The pressure vessel fits within an insulated, optionally refrigerated shipping container. The shipping container cushions the pressure vessel and ensures that the temperature of the shipping container remains constant throughout shipment. In some examples, the shipping container is insulated and therefore resists heating or cooling of the pressure vessel and contents throughout the shipping process.

Upon reaching a destination, such as a distribution hub for the SIT program, the insect transportation containers are unpacked from the pressure vessel. The insect transportation containers are placed within an unpacking device that opens, unloads, and closes the insect transportation containers within a closed environment such that the insects are not released while removing the insects from the insect transportation containers. The unpacking device receives the insects into a chamber that is coupled to a release device that is removable from the unpacking device. Following the loading of the insects into the release device, the insects can be released at the ultimate location of the SIT program.

In an illustrative example of the unpacking system, the system includes a receiving chamber where insects are unpacked and unloaded into, a dock providing a platform for a series of unpacking devices, a release device, and a transfer device for transferring insects from the receiving chamber into the release device. The unpacking system receives insect transportation containers and unloads the insects in a controlled, closed environment to ensure no accidental release of insects occurs during transition into the release device. The insect transportation containers are placed into respective unpacking devices which open, agitate to remove insects, and re-seals the insect transportation containers. Actuators of the unpacking devices enable a securing gate to lower and secure the insect transportation container in the dock and subsequent actuators separate the components of the insect transportation container to enable insects stored therein to exit. An agitation device engages with the perimeter of the insect transportation container to spin the insect transportation container and loosen insects from the interior thereof. A gate is actuated to lower between the components of the insect transportation container to close an opening in the dock while the insect transportation container, now empty, is removed from the unpacking device.

Turning now to the Figures, FIGS. 1-4 illustrate an example insect transportation container 100, according to at least some examples. The insect transportation container 100 provides a compact storage unit for insects during transportation. The insect transportation container 100 is sealable, cushioned, and ventilated to provide protection and oxygen to insects during transportation. The insect transportation container 100 secures together to prevent rotation of the components thereof and therefore prevent damage to the insects. The insect transportation container 100 is loaded from an insect loading device, such as described with respect to FIGS. 5-7. The insect transportation container 100 is then packed with other insect transportation containers 100 within the transportation device of FIGS. 8-11 until it reaches a destination. Upon reaching the destination, the insect transportation container 100 is unpacked with the unpacking device of FIGS. 12-18 to remove insects from the insect transportation container 100 and place them within a release device to release as part of an SIT program. The insect transportation container 100 includes a first portion 102 and a second portion 150 that together form the insect transportation container 100 and when coupled together enclose a volume where insects can be stored for transportation. It should be appreciated that the examples depicted in these figures and described below are illustrative examples of the various components and configurations. Other configurations, components, etc. may be used while remaining within the scope of the present disclosure.

Figure 2:
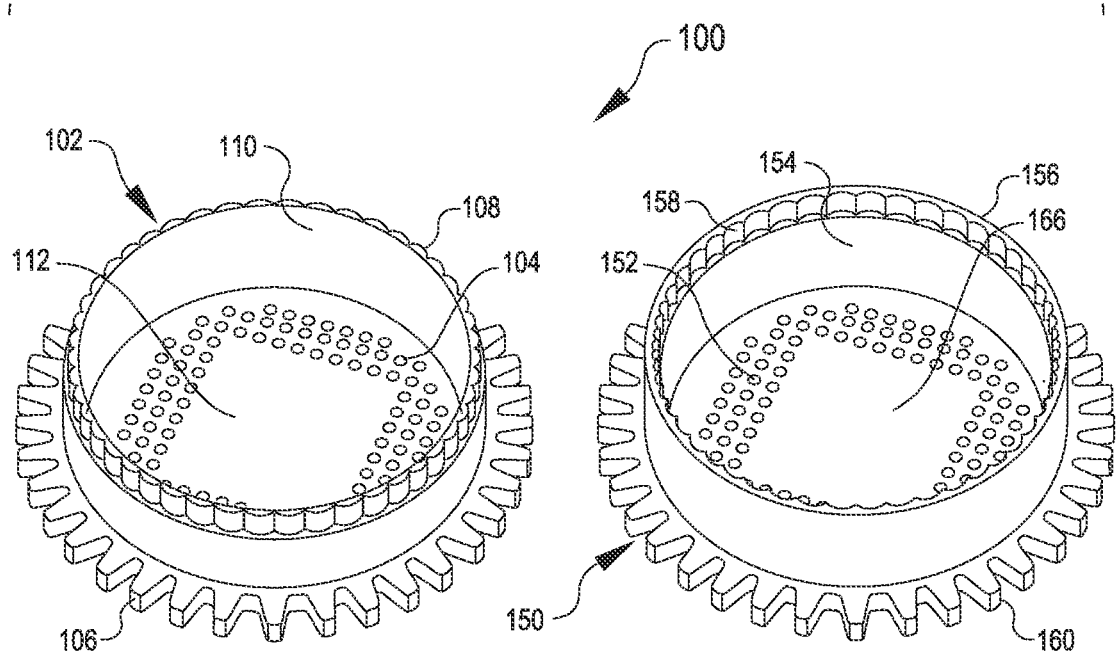
FIG. 2 illustrates additional views of the insect transportation container of FIG. 1, according to at least some examples.

In particular, FIGS. 1-2 show a first portion 102 of an insect transportation container 100 and a second portion 150 of the insect transportation container 100. The first portion 102 is shown with a base 112 facing upwards in the figure and the second portion 150 is shown with a base 166 facing downwards with respect to the figure. The first portion 102 and the second portion 150 can couple together to form the insect transportation container 100. The first portion 102 is shown flipped vertically in FIG. 2 below to illustrate differences between the first portion 102 and the second portion 150. The first portion 102 includes a base 112 that forms a surface from which wall 110 extends in the direction of axis 118. The base 112 has a round perimeter, though other shapes and perimeters may be used for the base 112. For example, square, rectangular, oval, and any other geometric or non-geometric shape can be used for the base 112. The base 112 has an engaging surface 106 and a wall 110 extending from the base 112. The base 112 has a diameter in a range of two to ten centimeters, though in some examples, the base 112 may have a diameter greater than ten centimeters or smaller than two centimeters, depending on the type or quantity of insects to be transported.

The engaging surface 106 extends in the same plane as the base 112 and has a number of pyramidal protrusions extending from the base 112 and around its perimeter, similar to teeth on a gear. The engaging surface 106 is useful for engaging with an agitating device of an unpacking device 402, as shown and described with respect to FIGS. 12-18. The agitating device engages with the engaging surface 106 to agitate, by rotating, vibrating, shaking, or otherwise agitating the first portion 102 to cause insects stored therein to come out of the interior of the first portion 102. The engaging surface 106 may be shaped as gear teeth, as shown, or may include other shapes and styles of engaging surfaces that enable an agitating device to agitate the first portion 102. Examples of engaging surfaces may include gear teeth, slots, keys, pinholes, threads, a frictional surface, or any other device that enable translation of motion or force from an agitating device to the first portion 102. The round perimeter of the base 112 may be useful for enabling the engaging surface 106 to cause the first portion 102 to rotate around an axis 118 perpendicular to the base 112 when engaged with the agitating device. In other examples, such as with a base 112 having a non-circular perimeter, the engaging surface may be useful for enabling translation of a vibratory motion or a force from the agitating device to the first portion 102.

The wall 110 extends perpendicular to the base 112, in a direction parallel to axis 118. The wall 110 and base 112 together partially enclose a cavity, the cavity fully enclosed when the first portion 102 is coupled with the second portion 150. The wall 110 has a perimeter identical to the perimeter of the base 112. The wall 110 extends in a direction perpendicular to the plane of the base 112 and extends a distance in a range of one to five centimeters, though in some examples the wall 110 may extend greater than five centimeters. For example, when wall 110 is greater than five centimeters, the volume enclosed within the insect transportation container 100 is large enough to contain five hundred insects. In some examples, the volume may be large enough to contain up to several thousand insects. In some examples, the volume may contain between one thousand and three thousand insects, between one thousand five hundred insects and two thousand insects. In some examples the volume may be large enough to contain up to one hundred thousand insects or as few as a few hundred insects.

Within the base 112 is formed a series of vent holes 104. The vent holes 104 extend through the base 112 from a first side of the base 112 to a second side of the base 112. The vent holes 104 enable air to flow through the base 112 from an exterior of the insect transportation container 100 to an interior of the insect transportation container 100. The vent holes 104 also enable air to flow from the interior to the exterior of the insect transportation container 100. The vent holes 104 are shown arrayed across the base 112. In some examples, instead of or in addition to the vent holes 104 being formed in the base 112, the vent holes 104 may extend through the wall 110 to provide airflow into and out of the insect transportation container 100.

The vent holes 104 have a diameter, width, or other cross-sectional dimension in the case of non-circular vent holes, that is smaller than a cephalothorax width of a representative insect to be transported within the insect transportation container 100. The size of the vent holes 104 ensure that insect cannot escape through the vent holes 104. In some examples, the value of the width dimension for the vent holes 104 may range from 800 microns to 1500 microns, which may be appropriate for containing certain species of mosquitos. Values larger than 1500 microns and smaller than 800 microns may be appropriate for other insect species. In a particular example, the value of the width dimension can be about 1200 microns.

At a distal end of the wall 110, opposite the base 112, the first portion 102 includes a first coupling portion 108. The first coupling portion 108 couples with a second coupling portion 158, of the second portion 150, to releasably couple the first portion 102 to the second portion 150. The first coupling portion 108 and the second coupling portion 158 couple together such that the first portion 102 and the second portion 150 are not able to rotate relative to one another. Rotation of the first portion 102 relative to the second portion 150 may result in damage to insects stored within the insect transportation container 100. Therefore, the first coupling portion 108 and the second coupling portion 158 resist or prevent relative rotation of the first portion 102 and the second portion 150.

As illustrated, the first coupling portion 108 includes a series of scalloped surfaces around the edge of the wall 110. The scalloped surfaces of the first coupling portion 108 is a male connector that interfaces with the second coupling portion 158, which is a female connector. The scalloped surfaces interface with scalloped surfaces of the second coupling portion 158 to couple together releasably. The scalloped surfaces, when coupled together, prevent rotation as described above. In some examples, the first coupling portion 108 may include other interface shapes and designs that serve to couple the first portion 102 and the second portion 150 together and prevent relative rotation when coupled together. As such, a threaded connection may be unsuited for coupling the first portion 102 and the second portion 150. In some examples, the first coupling portion 108 may include a key, channel, alignment pin, or other feature that only enables the first portion 102 and the second portion 150 to move along a direction parallel to an axis 118 perpendicular to the base 112 once the first coupling portion 108 and the second coupling portion 158 come into contact. In one example, the first coupling portion 108 may include a single or a series of keys that extend along the direction of the wall 110 that interfaces with corresponding recesses of the second coupling portion 158.

The insect transportation container 100, including the first portion 102 and the second portion 150 may be formed of a plastic, such as an injection moldable plastic, three dimensional printing plastic, or any other plastic. In some examples, the plastic may be polylactic acid (PLA), polypropylene, polyvinyl chloride, polycarbonate, acrylonitrile butadiene styrene (ABS), or polyethylene terephthalate (PETG). In some examples, the insect transportation container 100 may be formed of multiple materials, for example with base 112 formed of a first plastic in which openings 104 can be easily machined with wall 110 molded or secured to the base 110. In some examples, the insect container 110 may be formed of any rigid material, including plastics, resins, metals, or other such materials. The insect transportation container 100 may be formed by injection molding, additive manufacturing, machining, overmolding, or otherwise formed in any manner known to those with skill in the art.

Like the first portion 102, the second portion 150 includes a base 166 that forms a bottom of the second portion 150. The second portion 150 is identical to the first portion 102 with the exception of the second coupling portion 158, which mates with the first coupling portion 108. The base 166 has a round perimeter, though other shapes and perimeters may be used for the base 166. For example, square, rectangular, oval, and any other geometric or non-geometric shape can be used for the base 166. The base 166 has an engaging surface 160 and a wall 154 extending from the base 166. The base 166 has a diameter in a range of two to ten centimeters, though in some examples, the base 166 may have a diameter greater than ten centimeters.

The engaging surface 160 extends in the same plane as the base 166, the engaging surface 160 having a profile of pyramidal protrusions extending along the plane of the base 166. The engaging surface 160 is useful for engaging with an agitating device of an unpacking device 402, as shown and described with respect to FIGS. 12-18. The agitating device engages with the engaging surface 160 to agitate, by rotating, vibrating, shaking, or otherwise agitating the second portion 150 to cause insects stored therein to come out of the interior of the second portion 150. The engaging surface 160 may be shaped as gear teeth, as shown, or may include other shapes and styles of engaging surfaces that enable an agitating device to agitate the first portion. Examples of engaging surfaces may include gear teeth, slots, keys, pinholes, threads, a frictional surface, or any other device that enable translation of motion or force from an agitating device to the second portion 150. The round perimeter of the base 166 may be useful for enabling the engaging surface 160 to cause the second portion 150 to rotate around an axis 168 perpendicular to the base 166 when engaged with the agitating device. In other examples, such as with a base 166 having a non-circular perimeter, the engaging surface may be useful for enabling translation of a vibratory motion or a force from the agitating device to the second portion 150.

The wall 154 extends perpendicular to the base 166, in a direction parallel to a rotation axis 168 of the second portion 150. The wall 154 and base 166 together partially enclose a cavity, the cavity fully enclosed when the first portion 102 is coupled with the second portion 150. The wall 154 has a perimeter identical to the perimeter of the base 166. The wall 154 extends in a direction perpendicular to the plane of the base 166 and extends a distance in a range of one to five centimeters, though in some examples the wall 154 may extend greater than five centimeters, for example when the volume enclosed within the insect transportation container 100 is large enough to contain up to several thousand insects.

Within the base 166 there are a series of vent holes 152. The vent holes 152 extend from a first side of the base 166 to a second side of the base 166. The vent holes 152 enable air to flow through the base 166 from an exterior of the insect transportation container 100 to an interior of the insect transportation container 100. The vent holes 152 also enable air to flow from the interior to the exterior of the insect transportation container 100. The vent holes 152 are shown arrayed across the base 166. In some examples, the vent holes 152 may also extend through the wall 154 to provide additional airflow into and out of the insect transportation container 100.

The vent holes 152 have a diameter or width dimension in the case of non-circular vent holes, that is smaller than a cephalothorax width of a representative insect. The size of the vent holes 152 ensure that insect cannot escape through the vent holes 152. In some examples, the value of the width dimension for the vent holes 152 may range from 800 microns to 1500 microns, which may be appropriate for separating mosquitos. Values larger than 1500 microns and smaller than 800 microns may be appropriate for other insect species. In a particular example, the value of the width dimension can be about 1200 microns.

At a distal end of the wall 154, opposite the base 166, the second portion 150 includes a second coupling portion 158. The second coupling portion 158 couples with the first coupling portion 108 to releasably couple the first portion 102 to the second portion 150. The second coupling portion 158 and the first coupling portion 108 couple together such that the first portion 102 and the second portion 150 are not able to rotate relative to one another. Rotation of the first portion 102 relative to the second portion 150 may result in damage to insects stored within the insect transportation container 100. Therefore, the first coupling portion 108 and the second coupling portion 158 resist or prevent relative rotation of the first portion 102 and the second portion 150.

In particular, the second coupling portion 158 includes a series of scalloped surfaces around the edge of the wall 154. The scalloped surfaces interface with scalloped surfaces of the first coupling portion 108 to couple together releasably. The second coupling portion 158 includes a female connector around the perimeter 156 of the wall 154 that interfaces with the male first coupling portion 108. The scalloped surfaces, when coupled together, prevent rotation as described above. In some examples, the second coupling portion 158 may include other interface shapes and designs that serve to couple the first portion 102 and the second portion 150 together and prevent relative rotation when coupled together. As such, a threaded connection may be unsuited for coupling the first portion 102 and the second portion 150. In some examples, the second coupling portion 158 may include a key, channel, alignment pin, or other feature that only enables the first portion 102 and the second portion 150 to move along a direction parallel to an axis 168 perpendicular to the base 166 once the second coupling portion 158 and the first coupling portion 108 come into contact. In one example, the second coupling portion 158 may include a single or a series of keys that extend along the direction of the wall 154 that interfaces with corresponding recesses of the first coupling portion 108.

Figure 3:
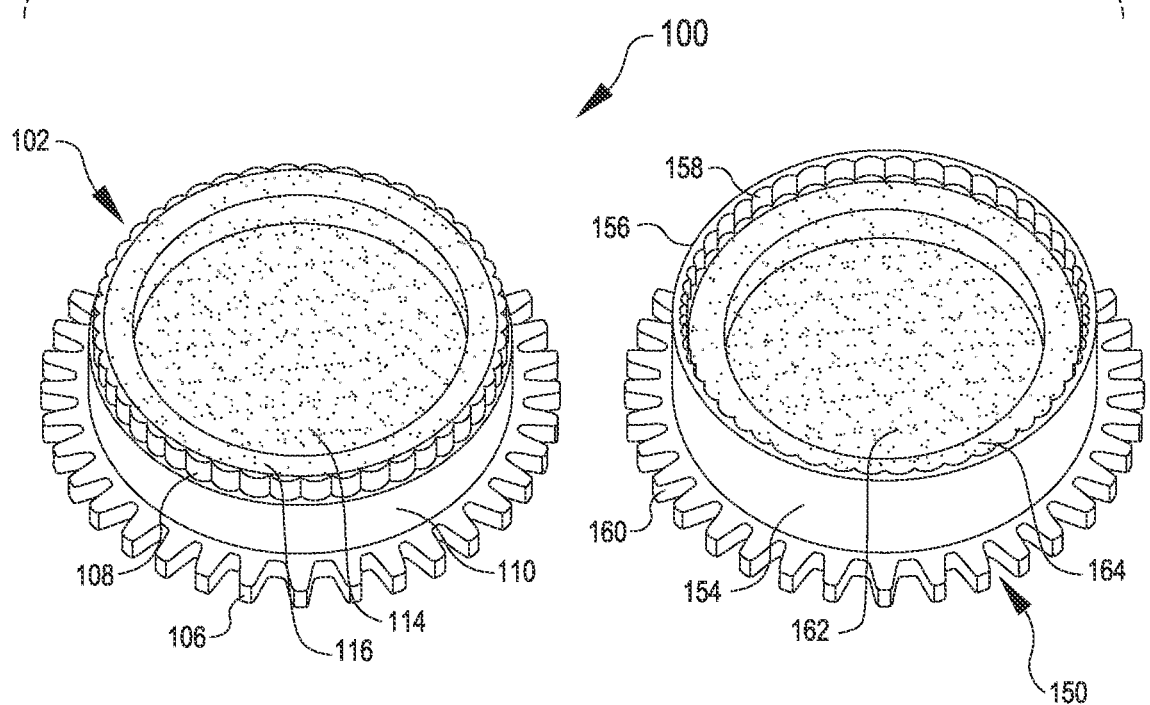
FIG. 3 illustrates the insect transportation container of FIG. 1 including foam inserts, according to at least some examples.

FIG. 3 illustrates the insect transportation container 100 of FIG. 1, with flexible inserts 114 and 162 for cushioning insects stored within the insect transportation container 100. The flexible insert 114 of the first portion 102 and the flexible insert 162 of the second portion 150 each include a rim around the perimeter that has a thickness greater than a thickness of the flexible insert 114 or flexible insert 162. The flexible insert 114 forms a base or bottom of the resilient material with the rim 116 around the perimeter to partially enclose a volume. The rim 116 may be integrally formed with the flexible insert 114 or may be a separate piece of foam that is stacked with the flexible insert 114. The flexible insert 114 and rim 116 form a cavity where insects may be retained and cushioned within the insect transportation container 100 when the first portion 102 and the second portion 150 are coupled together. The flexible insert 162 also includes a rim 164 the results in a cavity shape within the second portion 150 similar to the cavity described with respect to the first portion 102. The insect transportation container 100 forms a void within the device where insects are loaded for transportation after being placed in a dormant state, for example with the void defined by flexible inserts 114 and 162 and rims 116 and 164. In some examples, the flexible insert 162 may not include a rim 164, for example if the cavity for storing insects is entirely defined in the first portion 102. In some examples, the flexible insert 114 and the flexible insert 162 may each include only a single foam thickness and not include a rim 116 or rim 164. In such examples, the flexible insert 114 or flexible insert 162 may be formed of a compressible foam that compresses to cushion insects rather than apply sufficient force to damage an insect. The flexible insert 114, flexible insert 162, rim 116, and rim 164 may include a resilient foam such as a reticulated foam, a compressed polyester, a polyester fiberfill, a polyurethane foam, or an open cell foam that is highly compressible to prevent damage to the insects.

Figure 4:
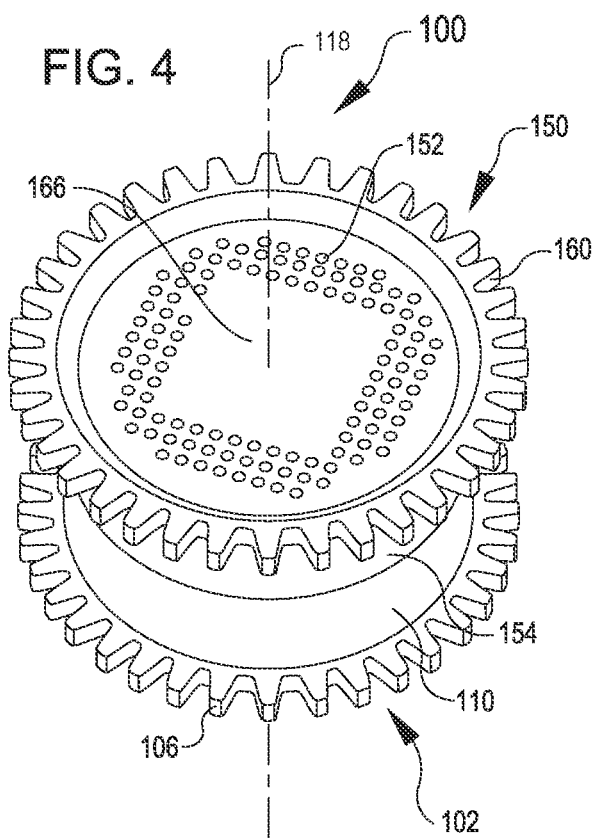
FIG. 4 illustrates the insect transportation container of FIG. 1 assembled together, according to at least some examples.

FIG. 4 illustrates the insect transportation container 100 with the first portion 102 and the second portion 150 coupled together, according to at least some examples. The insect transportation container 100 may be secured together with a band around the exterior of the device that fits between adjacent teeth of the engaging surface 160 and adjacent teeth of engaging surface 106. In some examples, the first coupling portion 108 and the second coupling portion 158 may include a feature or shape to ensure the first portion 102 and the second portion 150 remain secured together during transportation. The feature may include a frictional fit, a ball detent, a deformable tab, or other such engageable securing device. In some examples, the feature may include an external feature such as the external band described above or a connector pin that passes through an opening of both the first portion 102 and the second portion 150 to retain them together. Any other securing device or feature may be used to maintain the first portion 102 and the second portion 150 in contact when assembled together.

Figure 5:
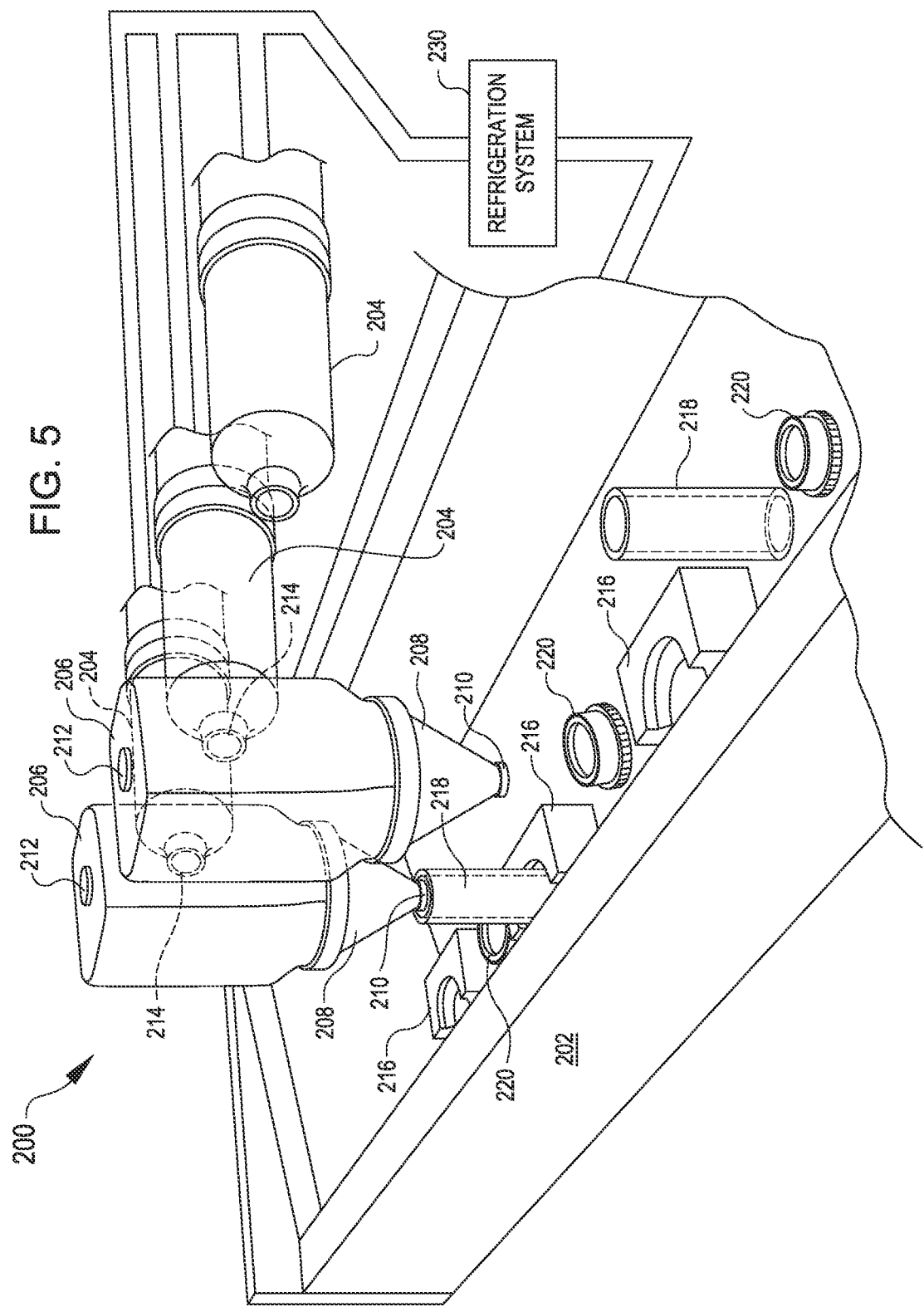
FIG. 5 illustrates a loading system for insect transportation containers in a conditioned environment, according to at least some examples.
Figure 6:
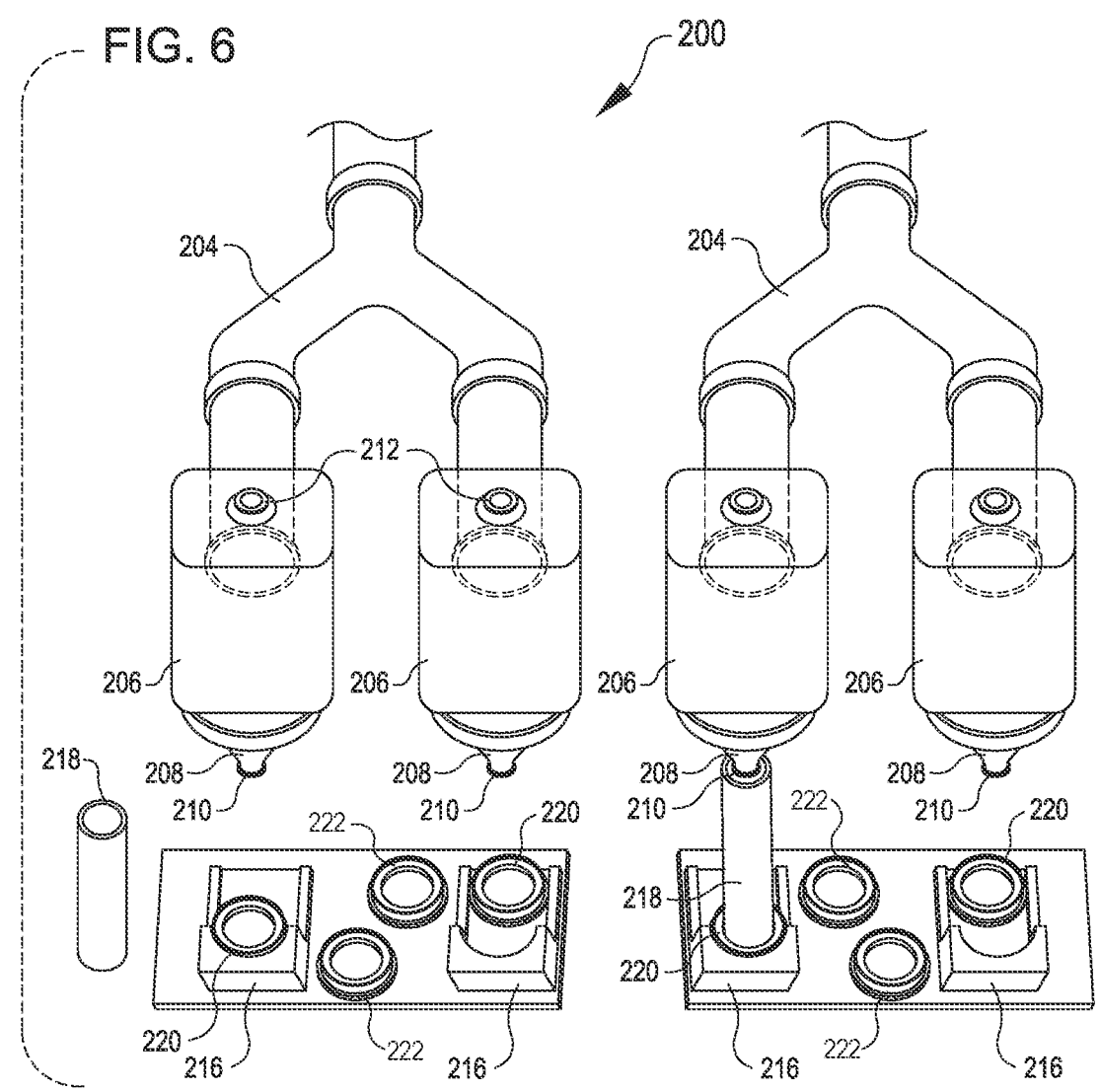
FIG. 6 illustrates a loading system for insect transportation containers, according to at least some examples.
Figure 7:
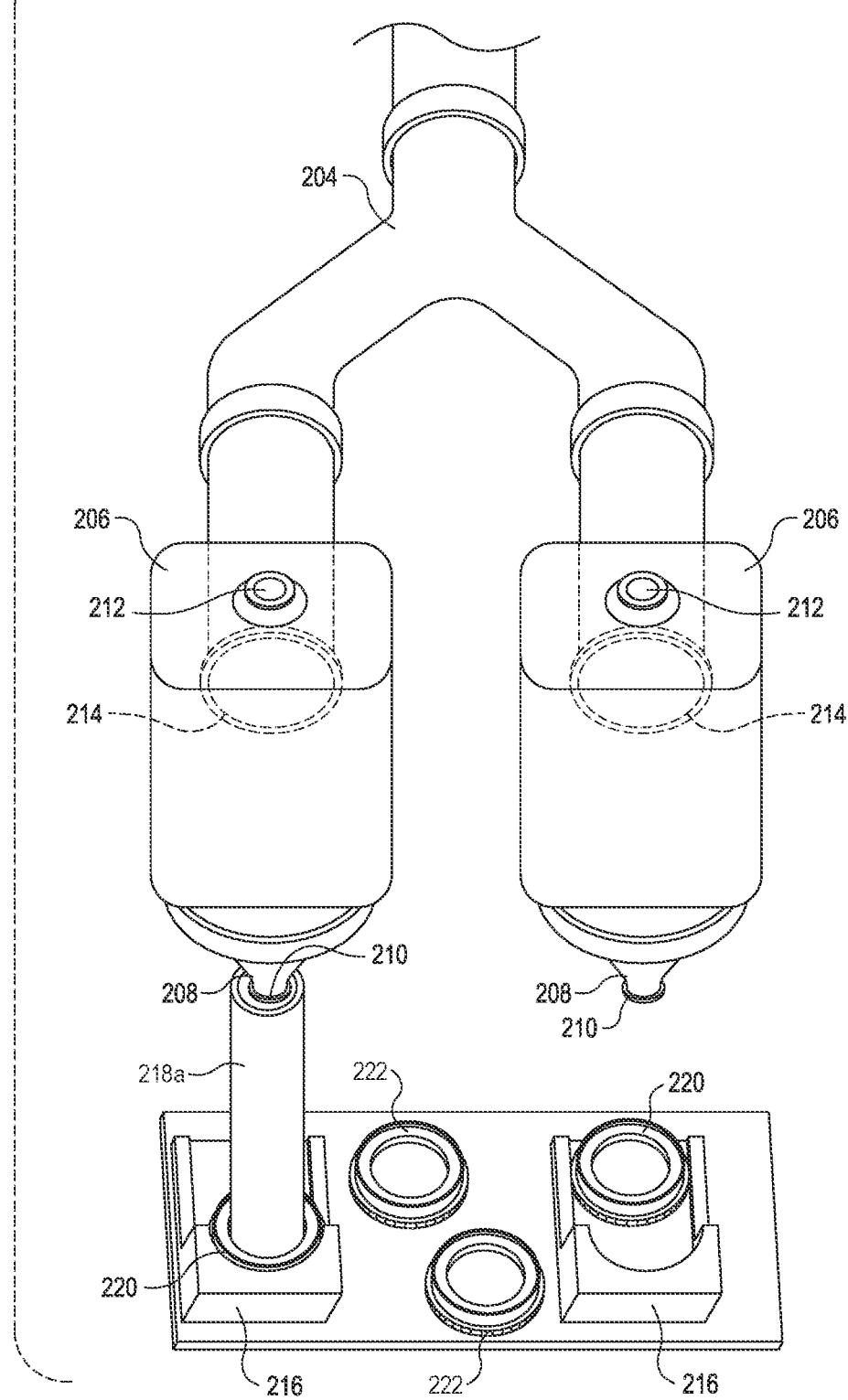
FIG. 7 illustrates a portion of the loading system for insect transportation containers of FIG. 6, according to at least some examples.

FIGS. 5-7 illustrate a system 200 for loading insect transportation containers 220 with insects, according to at least some examples. The insect transportation containers 220 are examples of the insect transportation container 100 shown and described with respect to FIGS. 1-4. The system 200 may be used to load the insect transportation container 220 according to a process 1900 shown and described with respect to FIG. 19. In an example, the system 200 is usable for receiving insects in an insect dispenser 206, for example received from an insect rearing system, putting the insects into a dormant or inactive state, and transferring the dormant insects into insect transportation containers 220 which are more compact for transportation to a destination and use in an SIT program. In this example, the system 200 includes a trough 202 to hold and retain insect transportation containers 220 during loading, insect dispensers 206 to transfer insects from an interior volume to the insect transportation containers 220, and one or more gas inlets 204 to which the insect dispensers 206 are removably mountable and through which cooled air or other gas is introduced into the interior volume of the insect dispensers 206, through opening 214 to sedate the insects therein. The gas inlets 204 direct gas, such as cooled air or knockdown gas, including any gas to displace oxygen. The knockdown gas may include carbon dioxide, nitrogen, high concentrations of oxygen, and other such gases, into the insect dispensers 206 through opening 214. The gas can come from a refrigeration system 230 or cooling system, such as the cooling system that cools the trough 202. The opening 214 includes a fine mesh or screen to prevent escape of insects while also enabling introduction of gas into the insect dispenser 206.

The system 200 includes a trough 202 in which the insect transportation container 220 may be placed to fill with insects from an insect dispenser 206. The trough 202 may be cooled by a refrigeration system 230 to maintain the interior of the trough 202 at a temperature lower than a surrounding ambient temperature. In some examples, the trough 202 may include a refrigeration system 230 integral to the trough 202 to lower a temperature of the trough 202 by cooling the walls of the trough 202. In some examples, the trough 202 may be insulated such that an interior of the trough 202 may be cooled and maintained at a cooler temperature by introducing a cooled gas into the trough 202. A cover (not shown) may enclose the system 200 to retain the cooled gas and ensure the trough 202 and other elements of the system 200 are maintained at the lower temperature. In some examples, a cover may enclose the trough 202 only. The lower temperature may cause insects within the system 200 to become dormant, by cooling below a temperature at which the insects do not remain active. The temperature within the trough 202 may be lowered to less than 8 degrees Celsius or fifty degrees Fahrenheit. The temperature within the trough 202 is also maintained above a freezing temperature to prevent damage to the insects that may occur while freezing.

Within the trough 202, the insect transportation containers 220 may be retained in a single position by a dock 216 which includes a slot that retains a first portion of the insect transportation container 220 for loading from an insect dispenser 206. The insects from the insect dispenser 206 may be conveyed from the insect dispenser 206 to the insect transportation container 220 through a conduit 218, the conduit 218 moveable and positionable when loading insects and enabling guiding of the insects such that insects from the insect dispensers 206 are retained entirely within the insect transportation container 220 after being transported and preventing accidental spilling or release of insects.

In some examples, the trough 202 may include a conveyor belt along the bottom surface of the trough 202. the conveyor belt may advance insect transportation containers 220 into, across, and out of the trough 202 for loading with insects. The conveyor belt may be controlled by a computing device, such as the computing device 2400 of FIG. 24 to advance the insect containers until they are aligned with an insect dispenser 206 for loading with insects. An electronic eye, laser gate, optical sensor, proximity sensor, or other such sensor may be positioned within the trough 202 to detect when the insect transportation container 220 is adjacent or in a proper location for loading through the loading port 210 of an insect dispenser 206. The computing device may also actuate a valve of the loading port 210 to release insects from the insect dispenser 206 into the insect transportation container 220. The conveyor belt may then advance the insect transportation container 220 along or out of the trough 202. The insect transportation container 220 may be closed by positioning a second portion of the insect transportation container 222 in contact with, and sealing the insect transportation container 220. This may be performed by a robotic arm controlled by the computing device in some examples.

The insect dispensers 206 include a funnel 208 and loading port 210 for loading insects into the insect transportation containers 220. The insect dispensers 206 may be loaded initially with insects from a rearing operation as part of an SIT program. The insects loaded within the insect dispensers 206 may be active and free to fly within the insect dispensers 206 after being loaded. The insect dispensers 206 are connected to a hanger (not shown) as part of the system 200 that maintains the insect dispensers 206 in a position adjacent the trough 202. In some examples, the insect dispensers 206 are connected or mounted to the gas inlets 204 to enable air to flow through the gas inlet 204 as well as support the weight of the insect dispensers 206. For example, the insect dispenser 206 may couple to the gas inlet 204 at opening 214. The mounting of the insect dispenser 206, either to a hanger system or to the gas inlet 204 may enable three dimensional alignment and positioning of the insect dispenser 206 with respect to the insect transportation containers 220. The insect dispensers 206 are removable to enable loading of insects from a rearing station or system and then subsequently transported to the system 200 for loading insect transportation containers 220. The insect dispensers 206 are shown maintained in a position vertically above the trough 202 such that gravity may be used to enable transfer of the insect to the insect transportation containers 220. The loading port 210 includes a cap or valve that can be opened to enable release of insects through the loading port 210. The funnel 208 ensures that insects within the insect dispenser 206, once put into a dormant state, settle to the bottom of the insect dispenser 206, at the funnel 208. The funnel 208 directs the insects to the loading port 210. In the example shown in FIGS. 5-7, the insects may travel along the funnel 208 through the loading port 210 due to gravity, which causes the insects to fall through the loading port 210, through the conduit 218, and into the insect transportation container 220.

In some examples, the insects may be removed from the insect dispenser 206 through the use of forced air. Gas is introduced into the insect dispenser 206 through gas inlets 204 and opening 214. As the gas is introduce into the insect dispenser 206 when the loading port 210 is open, the forced air will carry insects with the airflow out of the loading port 210. In some examples, the insect dispenser 206 includes a valve 212 for allowing air to escape from the insect dispenser 206 without allowing escape of insects. The valve 212 may be sealable such that when air is introduced into the insect dispenser 206 to drive the insects out through the loading port 210, the air only exits through the loading port 210 and not through the valve 212.

The system 200 may be operated manually or automatically. In automatic operation, an insect transportation container 220 is placed within the system 200, the system 200 automatically opens the insect transportation container 220 and positions it beneath the insect dispenser 206. A transfer tube or the insect dispenser 206 is lowered towards the insect transportation container 220. In some examples, the insect transportation container 220 may be raised towards the insect dispenser 206. The insects are knocked down within the insect dispenser 206. The insect dispenser 206 is agitated to remove insects from the insect dispenser 206. The insect transportation device 220 can be closed by the system 200 and subsequently removed from the system 200 after loading.

FIGS. 6-7 illustrates the system 200 of FIG. 5 showing a top view of the system 200, according to some examples. The gas inlets 204 are shown branching from a single trunk to multiple branches, this branching system enables the system 200 to accommodate multiple insect dispensers 206 at a single time and load multiple insect transportation containers 220 at the same time. The system 200 may be automated to fill the insect transportation devices through the use of a conveyor belt as described above.

To prepare the system to load insect transportation containers 220, a first portion of each of the insect transportation containers 220 is loaded into dock 216. The insect transportation containers 220 may be loaded by a human or automated operator that loads half of the insect transportation container 220. This enables insects to transfer into the half of the insect transportation container 220 which can then be closed by putting the second half on the insect transportation container 220 to enclose the insects within an inner volume and subsequently removing the insect container enclosing insects from the dock 216.

Conduit 218a is shown positioned below one of the loading ports 210 and resting on an insect transportation container 220. The conduit 218a may be coupled to or in close proximity with the loading port 210 in some examples, such that the funnel 208 and loading port 210 extend until in contact with, or within several millimeters of the insect transportation containers 220.

FIGS. 8-11 and 25 illustrates a live insect transportation packaging system 300, according to at least some examples. The transportation packaging system 300 enables transportation of live insects at a controlled temperature and pressure. Insects transported for SIT programs may need to travel great distances and through varying environments, including in cargo compartments of aircraft, but should ideally be maintained at or near constant temperatures and pressures throughout shipping to minimize or prevent damage to insects. The controlled temperature and pressure ensure that the insects remain dormant throughout shipping and are not damaged in transportation. The transportation packaging system 300 includes a package 302, insulation 304, a cooling device 306, and a pressure vessel 308. The package 302 is a reinforced shipping container, such as a package formed of cardboard, paperboard, plastic, metal, Styrofoam, or other rigid materials. The package 302 protects the internal elements from damage during transportation.

Figure 25:
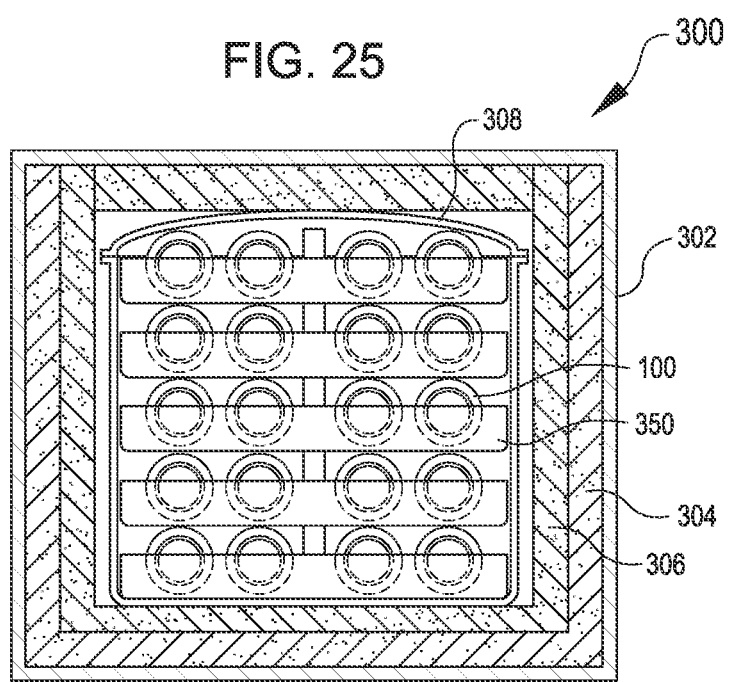
FIG. 25 illustrates a section view of the live insect transportation system of FIG. 8, according to at least some examples.

As illustrated in FIG. 25, which shows a section view of the live insect transportation system 300, The package 302 encloses the insulation 304, cooling device 306, and pressure vessel 308. The pressure vessel 308 includes trays 350 stacked on top of each other within the pressure vessel 308, the trays 350 each including recesses to receive insect transportation containers 100 with insects stored therein for transportation. The pressure vessel may be pressurized to greater than ambient pressure or may de-pressurized to less than ambient pressure.

The insulation 304 within the package 302 helps maintain the temperature within the package 302 at or near a constant temperature throughout the shipping process. The insulation 304 can include any type of insulation including fiberglass, foam, open cell foam, closed cell foam, aerogel, vacuum insulation, or other known insulation types.

Within the insulation 304 is a cooling device 306. The cooling device lowers the temperature within the package 302 to below an ambient temperature and serves as a temperature source that causes the temperature within the package 302 to remain near constant, when used in connection with the insulation 304. The cooling device 306 may include an ice pack or other passive cooling device. In some examples, the cooling device 306 may include a powered conditioning system that relies on a power source to provide cooling to the package 302. Battery powered cooling systems may enable transportation of insects over greater distances than passive cooling systems.

The package 302 is configured to hold the pressure vessel 308 that contains insect transportation devices, such as the insect transportation container 100 of FIGS. 1-4. The pressure vessel 308 may be formed of a thermally conductive material such that cooling device 306 is able to maintain a temperature within the pressure vessel 308. The pressure vessel 308 includes a lid that can be sealed and is openable for loading with insect transportation devices, as shown in FIG. 10.

Figure 8:
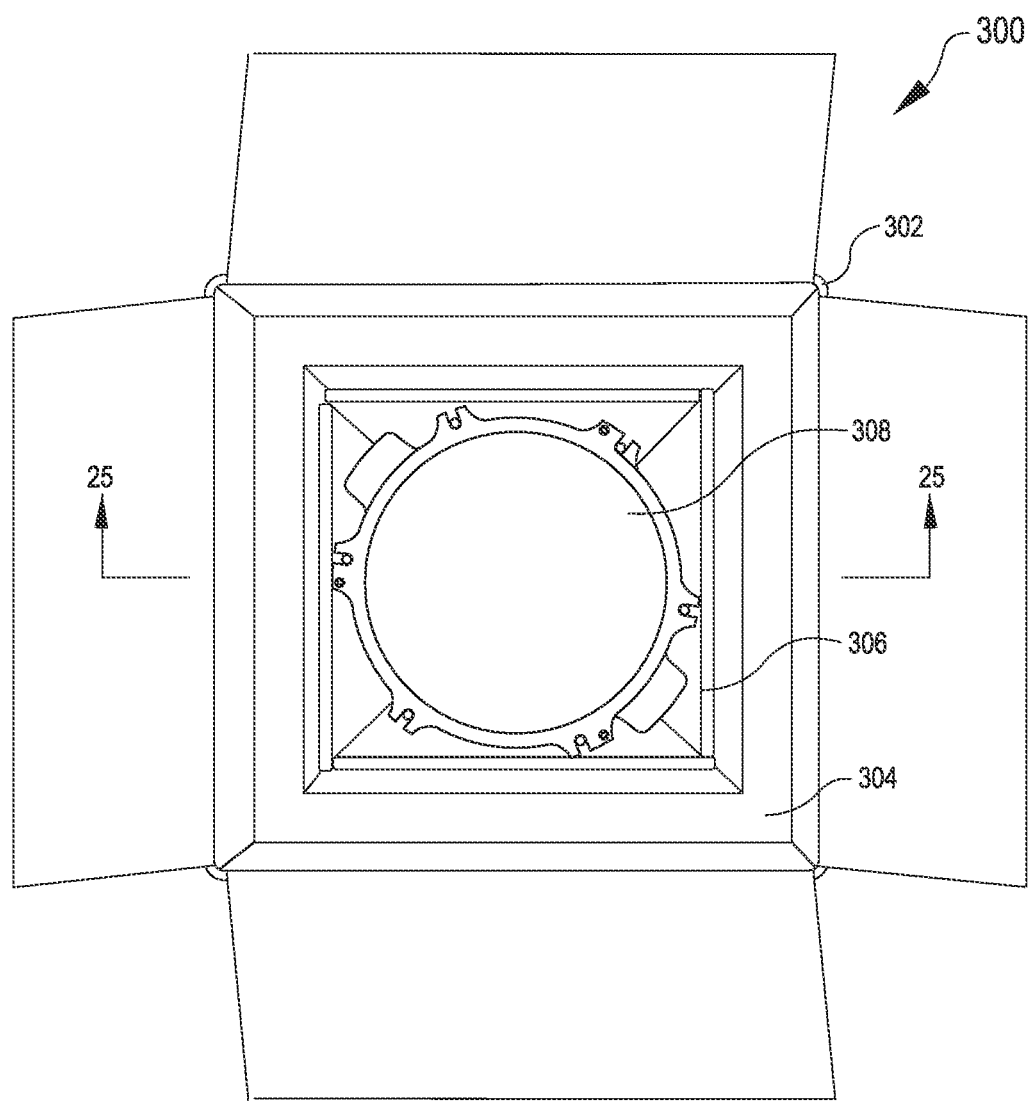
FIG. 8 illustrates a live insect transportation packaging system, according to at least some examples.
Figure 9:
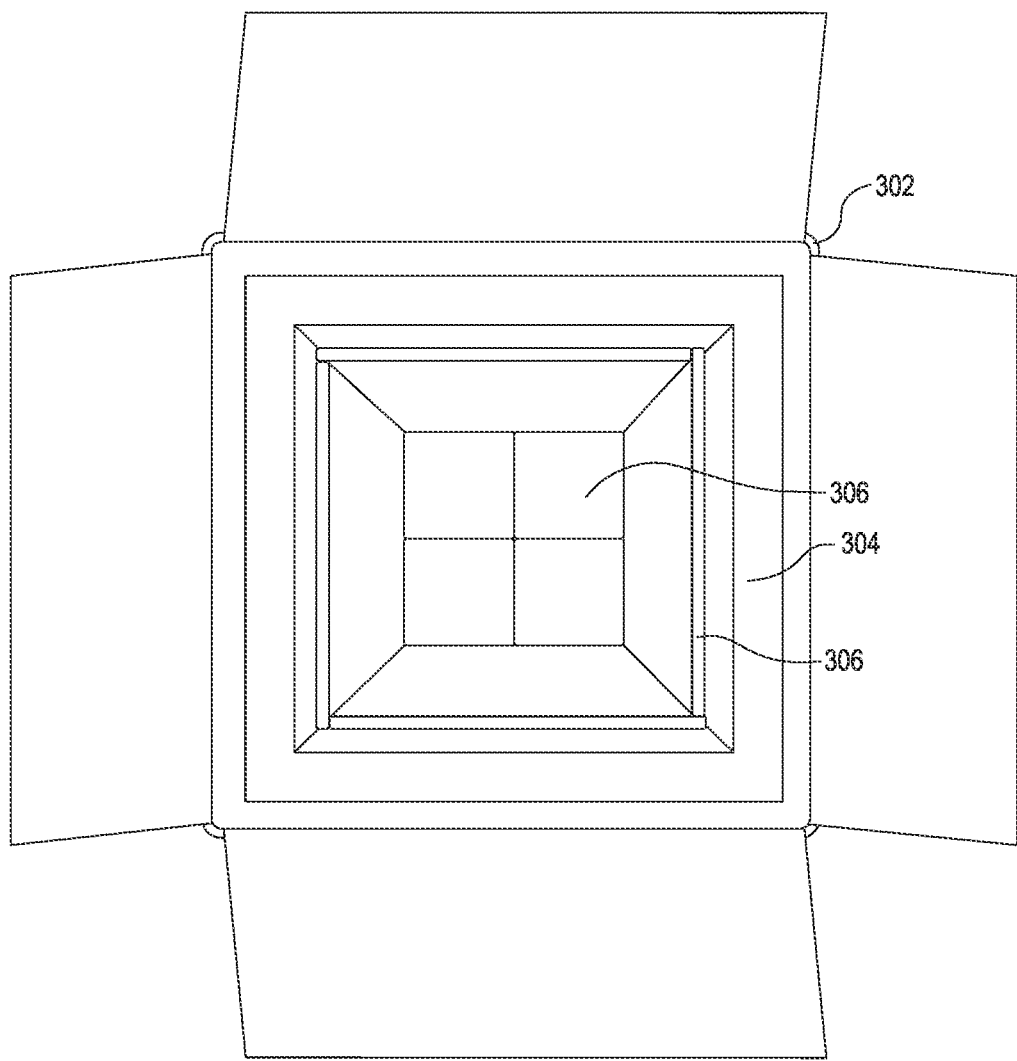
FIG. 9 illustrates external packaging of the live insect transportation packaging system of FIG. 8, according to at least some examples.

FIG. 9 illustrates external package 302 of the live insect transportation packaging system of FIG. 8, according to at least some examples. The package 302 is shown with the pressure vessel 308 removed. The package 302 includes insulation 304 around all surfaces of the interior of the package 302 and also includes cooling device 306 around all surfaces of the insulation 304. In some examples, such as including a powered cooling device 306, the cooling device may be positioned in a single location within the package 302 rather than all around the inside.

Figure 10:
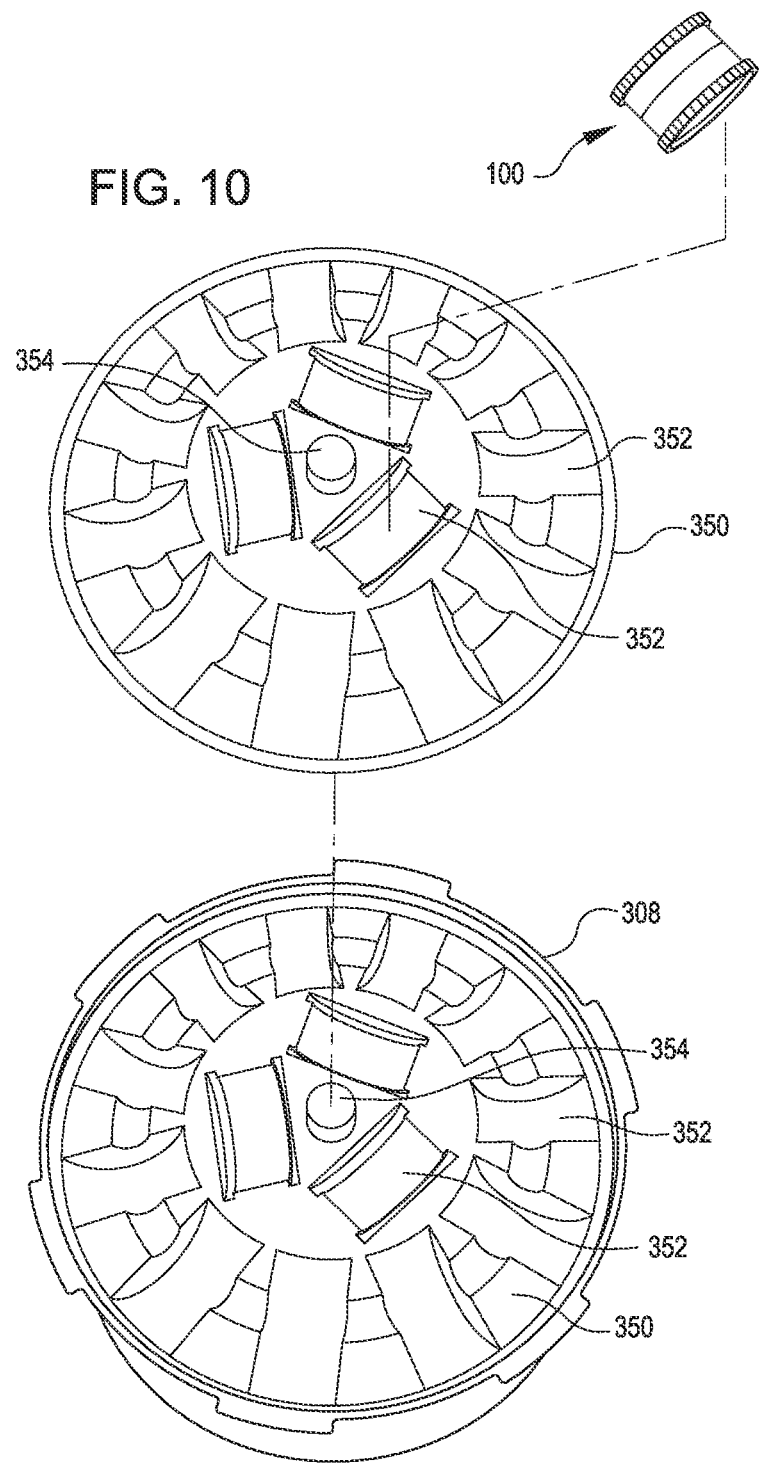
FIG. 10 illustrates an internal compartment of the live insect packaging system of FIG. 8 showing packing trays, according to at least some examples.

FIG. 10 illustrates an internal compartment of the pressure vessel 308 of FIG. 8 showing packing trays, according to at least some examples. The pressure vessel 308 includes a lid (not shown) that seals the pressure vessel to prevent fluctuations in pressure experienced by the insects during transportation. Within the pressure vessel 308 are a series of trays 350. The trays have an exterior perimeter that corresponds to an interior perimeter of the pressure vessel 308. The trays 350 include shaped recesses 352 on an upper side of each tray 350, the shaped recesses 352 corresponding to a shape of insect transportation devices 100. The insect transportation devices 100 may be the insect transportation container 100 of FIGS. 1-4. The trays 350 rest on top of one another to stack within the pressure vessel 308.

In some examples, the pressure vessel 308 may be a rigid or semi-rigid container capable of resisting a pressure difference between and internal and external volume. The pressure vessel 308 may include a flexible or deformable pouch, such as a sealable plastic pouch capable of withstanding internal and external pressures. The pressure vessel 308 may also include other vessels such as vacuum sealable pouches, rubber enclosures, elastic vessels, flexible bladder tanks such as used for holding fuel or water onboard aircraft, and other such flexible pressure vessels 308. Rigid pressure vessels may include those formed of metals, hard plastics, sealed through the use of gaskets around openings and/or ports to provide access into the pressure vessel 308.

The trays 350 also include a carbon dioxide scrubbing device 354, or position for placing the same within the pressure vessel. The carbon dioxide scrubbing device 354 may scrub or remove carbon dioxide from the environment within the pressure vessel 308 to ensure the concentration of carbon dioxide does not exceed a threshold at which the insects may become damaged.

The carbon dioxide scrubbing device 354 may be passive or active, but in either case is to remove carbon dioxide from the environment. In an example passive carbon dioxide scrubber 354, a container or package having an air-permeable enclosure is placed within the pressure vessel 308. The air-permeable enclosure may have a fine mesh, weave, or holes therein to allow transfer of air through the enclosure but to retain particles within the enclosure. The air-permeable enclosure of the carbon dioxide scrubbing device 354 may include a soda lime substance that removes carbon dioxide from the environment. In some examples, the air-permeable enclosure may also include activated carbon, amines such as monoethanolamine, quicklime, serpentinite, olivine, sodium hydroxide, lithium hydroxide, potassium hydroxide, metal-organic frameworks, or other known carbon dioxide scrubbing compounds. The passive carbon dioxide scrubber can operate to remove carbon dioxide without the need for a power supply, thereby increasing a distance the package may be shipped and/or increasing a time the insects can be contained within the pressure vessel 308. An active carbon dioxide scrubbing device may include powered elements such as a fan to circulate and drive carbon dioxide into contact with a soda lime compound. In some examples, the powered carbon dioxide scrubbers may include regenerative carbon dioxide removal systems and membrane gas separators. As carbon dioxide is scrubbed from the environment within the pressure vessel 308, the pressure within the pressure vessel may decrease, and in some examples there may be insufficient oxygen to maintain the insects during transportation.

FIG. 11 illustrates a live insect transportation system 300 of FIG. 10 including a gas supply system, according to at least some examples. The gas supply system includes a reservoir 360, a regulator 362, and a gas-tight connection 364. The gas-tight connection 364 couples the pressure vessel to the regulator 362 and reservoir 360. In some examples, the reservoir 360 and regulator 362 may be included within the pressure vessel 308 and therefore eliminate the need for a gas-tight connection 364. The regulator 362 causes a pressure within the gas-tight connection 364 and pressure vessel 308 to remain constant as carbon dioxide is scrubbed, thereby reducing the gas and pressure within the pressure vessel. The regulator 362 may be any known regulator that is capable of maintaining a pressure in a container based on release of gas from a pressurized reservoir. In some examples, the rate of gas release through the regulator 362 may be regulated and controlled by an on-board computing device coupled to an environment sensor (such as pressure and humidity sensors) within the pressure vessel 308. As the pressure sensor detects a pressure that is decreasing, the computing device may cause the regulator 362 to release additional gas into the pressure vessel 308 to maintain a pressure level.

The reservoir 360 includes oxygen for introduction into the pressure vessel 308 for insects respiration during transportation. In some examples, the reservoir 360 includes a mixture of gases, such as oxygen and carbon dioxide in a mixture. The reservoir 360 may include gases mixed with the oxygen to reduce a concentration of oxygen for shipping purposes. During shipping there are regulations on shipping methods and requirements for oxygen concentrations and pressures above particular thresholds. By mixing the oxygen with carbon dioxide, or another gas, the oxygen concentration can be reduced and thereby increase the safety of shipping the package. In some examples, inert gases may be mixed with the oxygen. In some examples, carbon dioxide may be a preferred gas to mix with the oxygen. As the carbon dioxide and oxygen mixture is introduced into the pressure vessel 308, the carbon dioxide will be scrubbed by the carbon dioxide scrubber 354 leaving only the introduced oxygen for use by the insects. The oxygen and carbon dioxide may be mixed at a ratio such that no special precautions are needed during shipment, for example at a mixture of around eighty percent carbon dioxide and twenty percent oxygen. Other mixture ratios are envisioned and intended to be covered by this disclosure, so long as the mixture of oxygen and carbon dioxide can be safely shipped.

In some examples, other systems may be used for oxygen introduction into the pressure vessel 308 besides the reservoir 360. Some systems may include the use of reactants that, when reacted together, produce oxygen gas as a byproduct of the reaction. One such exemplary reaction may include hydrogen peroxide reacting with a reactant to produce oxygen and water. Such systems produce only oxygen and water which are safe for insects within the pressure vessel 308. Reactant systems rely on a metering system and process to produce oxygen at a controlled rate such that the pressure and concentration of oxygen within the pressure vessel 308 is maintained at a constant or near-constant level.

Controlling systems for reactant-based oxygen production systems may include a sensor array within the pressure vessel 308. The sensor array may include temperature, humidity, pressure, oxygen, and carbon dioxide sensors. The sensor array may be included with other elements within the pressure vessel 308. In an example, the sensor array may be incorporated with the carbon dioxide scrubbing device 354. In some examples, the sensor array may be positioned on the wall of the pressure vessel 308 and sense environmental parameters through openings in the wall of the pressure vessel 308 sealed around the sensor array. The sensor array may be in communication with an on-board computing device of the shipping system 300. The sensor array may be useful for aiding in control of an active cooling device 306, for example by enabling control of the active cooling device 306 based on the temperature sensor within the pressure vessel 308. In the case of oxygen production, the oxygen and/or carbon dioxide sensors may be in communication with the computing device. The computing device may be a computing device 2400 as shown and described with respect to FIG. 2400. The computing device 2400 may be configured to cause a reactant based oxygen production system to produce oxygen when the oxygen level detected by the oxygen sensor drops below a threshold level. In some examples, the computing device may cause the oxygen production system to maintain a constant oxygen level within the pressure vessel 308.

Turning to the reactant-based oxygen production system, the system may rely on a reaction between a reservoir of hydrogen peroxide and a reactant, such as platinum. The reaction between the two produces water and oxygen. By controlling a flow of hydrogen peroxide into contact with the reactant, the rate of oxygen production may be controllable by the computing device. For example, the use of a controllable valve allows the computing device to adjust the flow rate of hydrogen peroxide and thereby control the rate of oxygen production. In some examples, other reactants may be used for oxygen production, such as sodium percarbonate, water, and a reactant in some systems. In some examples an electrolysis system may be used to produce oxygen from water stored within the system. Other reactants may include sodium chlorate and potassium permanganate. The oxygen production systems ensure that the insects being transported have adequate oxygen for respiration during transportation and arrive at an unpacking device 400 ready for packing into a release device as part of the SIT program.

FIG. 12 illustrates an unpacking system 400 for unpacking insects from insect transportation devices and loading the insects into an insect release device 410, according to at least some examples. The unpacking system 400 includes a receiving chamber 404, a dock 412, a series of unpacking devices 402, a release device 410, dividers 408 for the release device 410, and a divider connector 406. The unpacking system 400 receives insect transportation devices, such as the insect transportation devices 100 of FIGS. 1-4 and unloads the insects in a controlled, closed environment to ensure no accidental release of insects occurs during transition into the release device 410. The unpacking devices 402 receive insect transportation devices including insects stored therein and open the devices to transfer the insects into the receiving chamber 404 as described with respect to FIGS. 13-18.

The insect release device 410 can be any insect release device for releasing insects, for example as part of an SIT program. The insect release device 410 can include optional dividers 408 and a divider connector 406 to divide a population of insects into multiple chambers for staged releases. Additionally, the divider connector 406 and dividers 408 can be used to enable movement of the insects from the receiving chamber 404 into the release device 410.

The unpacking system 400 may be manually operated, according to method 2300 of FIG. 23, below. The unpacking system 400 may also be automated and controlled by a computing device, such as computing device 2400. The automatic operation of the unpacking system 400 may include steps similar or identical to the manual operation of the unpacking system 400.

FIGS. 13-18 describes a series of states of the unpacking system 400 corresponding to a series of steps of a process for unpacking insects from insect transportation devices. Beginning with FIG. 13, FIG. 13 illustrates a first step in the process of unpacking insects from an insect container using the unpacking device 402 of FIG. 12, according to at least some examples. The unpacking device 402 includes a dock 450 shaped to receive an insect transportation container 100. The dock 450 defines a passageway 452 extending between the portion that receives the insect transportation container 100 and the internal volume of the receiving chamber 404. When the insect transportation container 100 is opened, the insects travel from the insect transportation container 100 through the passageway and into the internal volume of the receiving chamber 404. Within the dock 450 there is an agitation device 464 and an opening actuator 456.

In an example, the unpacking device 402 unpacks insects from insect transportation containers 100 after they are placed in dock 450. In particular, the unpacking device 402 includes vertical actuators 472 and 474 to move an upper gate 470 and a passageway seal 466 to enclose the insect transportation container 100 within the dock 450 and prevent insects from escaping. Opening actuators 456 separate portions of the insect transportation containers 100 after they are secured in the dock 450. Agitation device 464 engages with the open insect transportation container 100 to agitate insects out of the insect transportation container 100 and through the passageway 452 into the chamber 404. From the chamber 404, the insects can be transferred into the release device 410.

When the insect transportation container 100 is loaded into the dock 450 and the upper gate is closed, the agitation device 464 engages with the engaging surface 106 of the insect transportation container 100 and agitates the insect transportation container 100 to cause insects contained therein to release and pass through the passageway 452. The agitating device 464 includes a gear driven by a motor 462 to cause rotation of the gear. When engaged with the insect transportation container 100, the rotation causes the insect container to rotate. In some examples, the agitation device may include a vibration mechanism, such as an offset flywheel that introduces a vibratory motion into the insect transportation device. Additional agitation devices may include mechanisms to apply force or movement to the insect transportation container 100 or to agitate insects within the insect transportation container 100. In some examples, the agitation device may include an air nozzle directed to blow air between the two parts of the insect transportation container 100 to agitate and cause insects held therein to fall into the passageway 452.

When the insect transportation container 100 is loaded into the dock 450 and the upper gate is closed, the opening actuator 456 actuates a plate 454 between an open position and a closed position. In the closed position, an insect transportation container 100 held within the dock 450 is closed, with the two portions remaining in contact with one another. In the open position, the plate 454 applies a force to one portion of the insect transportation container 100 to open the insect transportation container 100 (e.g., drive the two portions of the insect transportation container 100 apart or drive one portion relative to the other). In some examples, the plate 454 may apply the force to the engaging surface of the insect transportation container 100 or may apply the force to the base of one portion of the insect transportation container 100. A corresponding opening actuator 460 is likewise positioned on the upper gate 470 such that when the upper gate 470 is in contact with the dock 450, the opening actuator 460 and plate 458 can apply a force to open and close the insect transportation container 100.

The upper gate 470 is actuated vertically towards and away from the dock 450 by a vertical actuator 474 coupled to the upper gate 470. The upper gate 470 includes a receiving surface (not shown) shaped to partially surround the insect transportation container 100 similar to the dock 450 to receive an insect transportation container 100 and hold it securely between the dock 450 and the upper gate 470. The receiving surface may, in an example, have an arch shape that corresponds to the radius of the insect transportation container 100.

A passageway seal 466 and lifter 468 are actuated vertically by a vertical actuator 472 to move the passageway seal 466 into and out of contact with the passageway 452 to seal the passageway 452 and prevent escape of insects from the receiving chamber 404. The vertical actuator 472 moves the passageway seal 466 independent of the actuation of the upper gate 470 by the vertical actuator 474. The lifter 468 is a surface that is actuated by the vertical actuator 472 and interfaces with the insect transportation container 100 after unloading the insects to lift the insect transportation container 100 out of the dock 450. After the vertical actuator 472 actuates the lifter 468 vertically downward such that the passageway seal 466 closes the passageway 452, the lifter 468 is positioned beneath the insect transportation container 100. After the insect transportation container 100 is closed, the lifter 468 applies a force to lift the insect transportation container 100 out of the dock 450 as the vertical actuator 472 moves the lifter 468 to an upper position.

With reference to FIG. 13, the unpacking device 402 is shown in an open configuration. In the open configuration, the dock 450 is free of any insect transportation devices 100, the passageway 452 is unsealed, and the upper gate 470, passageway seal 466, and lifter 468 are all positioned at an open position, away from the dock 450.

With reference to FIG. 14, an insect transportation container 100 is loaded into the dock 450, with a seam between the two portions of the insect transportation container 100 positioned over the passageway 452. The insect transportation container 100 is loaded with insects in a dormant state, ready to be unpacked and loaded into a release device as part of the SIT program. The insect transportation container 100 is loaded into the dock 450 such that the engaging surface of the insect transportation container 100 interfaces with the agitation device 464 for subsequent agitation of the insect transportation container 100.

Figure 15:
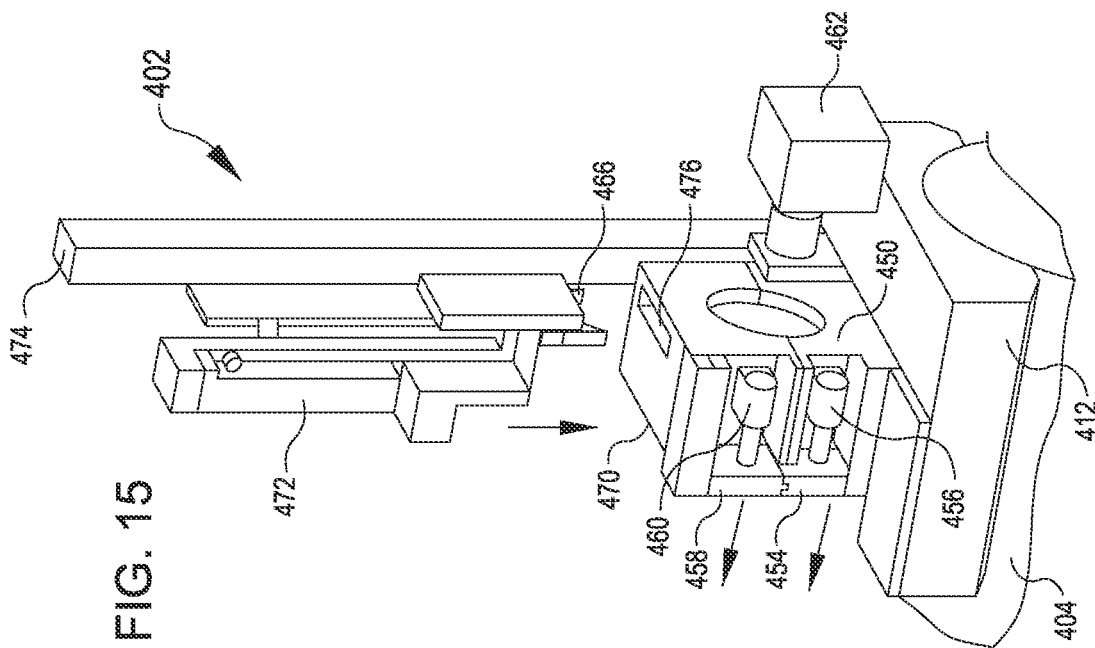
FIG. 15 illustrates a step in a process of unpacking insects from an insect transportation container using the unpacking device of FIG. 12, according to at least some examples.

With reference to FIG. 15, once the insect transportation container 100 has been loaded into the dock 450 (as illustrated in FIG. 14), the upper gate 470 is lowered by the vertical actuator 474 to enclose the insect transportation container 100 within the upper gate 470 and the dock 450. Enclosing the insect transportation container 100 ensures that as insects are released from the device they are not free to escape into the surrounding environment.

After the upper gate 470 is lowered onto the dock 450, the opening actuators 456 and 460 move the plates 454 and 458 from the closed position to the open position. In moving from the closed position to the open position, the plates 454 and 458 apply a force to one part of the insect transportation container 100 to drive the insect container into separate components and allow release of the insects stored therein through the passageway 452 into the receiving chamber 404.

Figure 16:
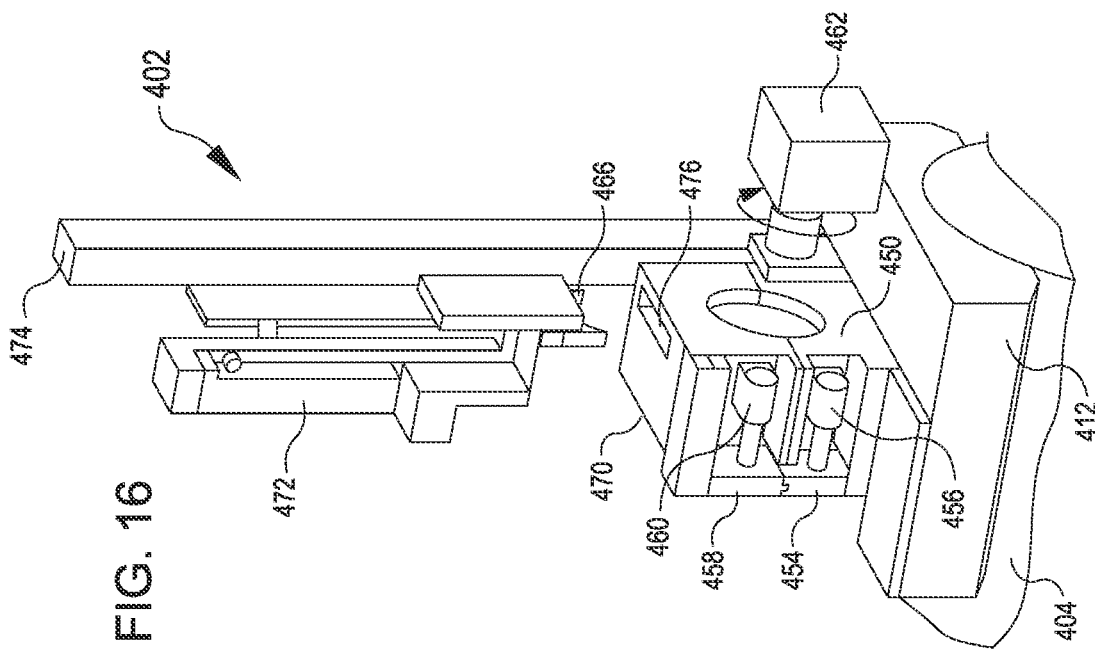
FIG. 16 illustrates a step in a process of unpacking insects from an insect transportation container using the unpacking device of FIG. 12, according to at least some examples.

With reference to FIG. 16, after the insect transportation container 100 is opened (as described with reference to FIG. 15), the agitating device 464 is rotated by the motor 462. The rotation of the motor 462 drives the agitating device 464 and causes the agitating device to apply a rotational force to the insect transportation container 100. The rotational force causes the insect transportation container 100 to spin within the dock 450 and agitate any insects that may cling to the foam inserts to fall out and through the passageway 452. Additionally, an air nozzle positioned in the upper gate 470 may direct a blast of air towards the passageway 452 between the two portions of the insect container to drive any remaining insects through the passageway 452.

Figure 17:
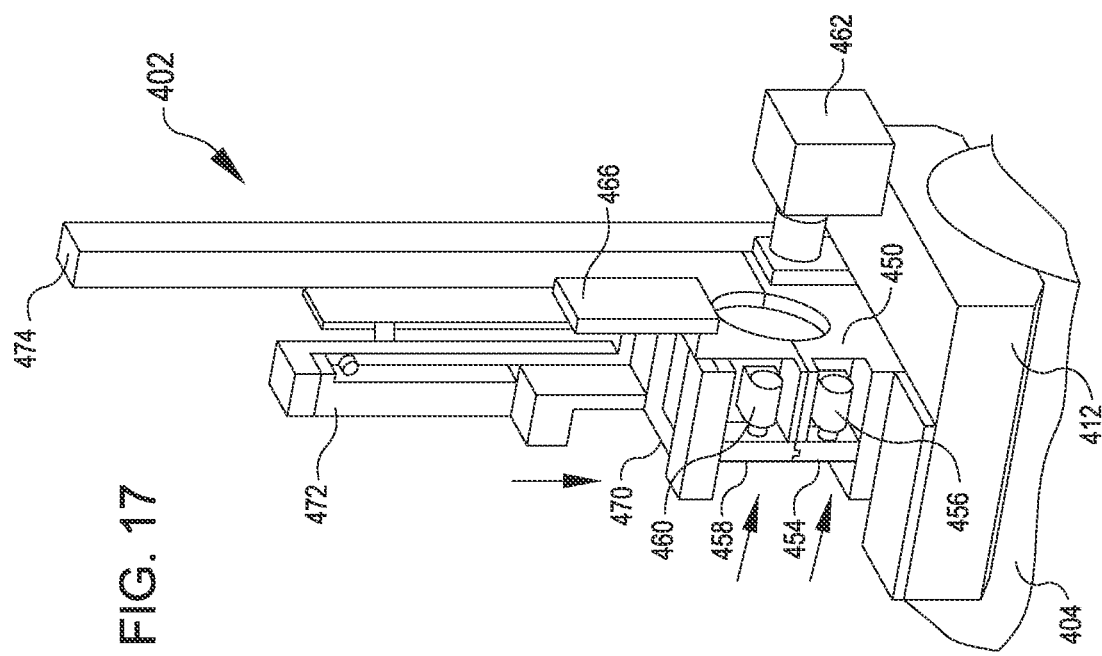
FIG. 17 illustrates a step in a process of unpacking insects from an insect transportation container using the unpacking device of FIG. 12, according to at least some examples.

With reference to FIG. 17, after the agitating device 464 has caused the insect container to empty of insects stored therein (as described with reference to FIG. 16), the vertical actuator 472 causes the passageway seal 466 and lifter 468 to descend into the upper gate 470 and dock 450. The passageway seal 466 and lifter 468 pass through the upper gate 470 through an opening 476 and between the two portions of the insect transportation container 100. The lifter 468 includes a "c" shape that allows the two portions of the insect transportation container 100 to be brought together after the lifter 468 has descended fully with the passageway seal 466 positioned to seal the passageway 452.

After the passageway seal 466 and lifter 468 have descended, opening actuators 456 and 460 cause the plates 454 and 458 to move to the closed position, as illustrated in FIG. 17. In moving to the closed position, the plates 454 and 458 apply a closing force to bring the two parts of the insect transportation container 100 together.

After the insects from the insect transportation container 100 are transferred into the receiving chamber 404, the dividers 408 and divider connector 406 can be driven laterally to push or move the insects into the release device 410. This action causes the receiving chamber 404 to once again empty of insects and is prepared to receive additional insects for another release device 410.

Figure 18:
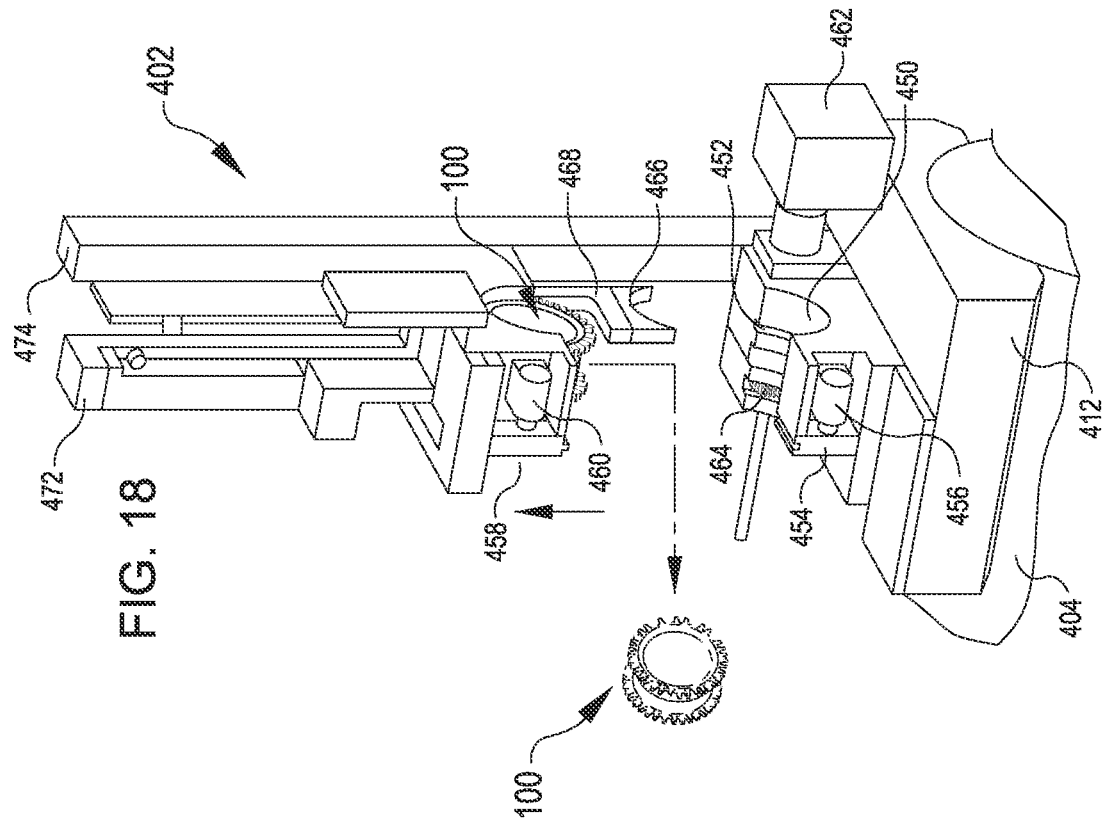
FIG. 18 illustrates a step in a process of unpacking insects from an insect transportation container using the unpacking device of FIG. 12, according to at least some examples.

With reference to FIG. 18, after the insect transportation container 100 has closed as shown in FIG. 17, the upper gate 470, passageway seal 466 and lifter 468 are actuated by the vertical actuators 472 and 474 to lift to an open position, as shown in FIG. 13. While lifting, the surface of the lifter 468 contacts the insect transportation container 100 and raises it out of the dock 450 for removal. The process beginning at FIG. 13 may then be repeated with another insect transportation container 100.

FIGS. 19-23 illustrate example processes 1900, 2000, 2100, 2200, and 2300 corresponding methods of packaging and transporting insects, according to at least some examples.

Figure 19:
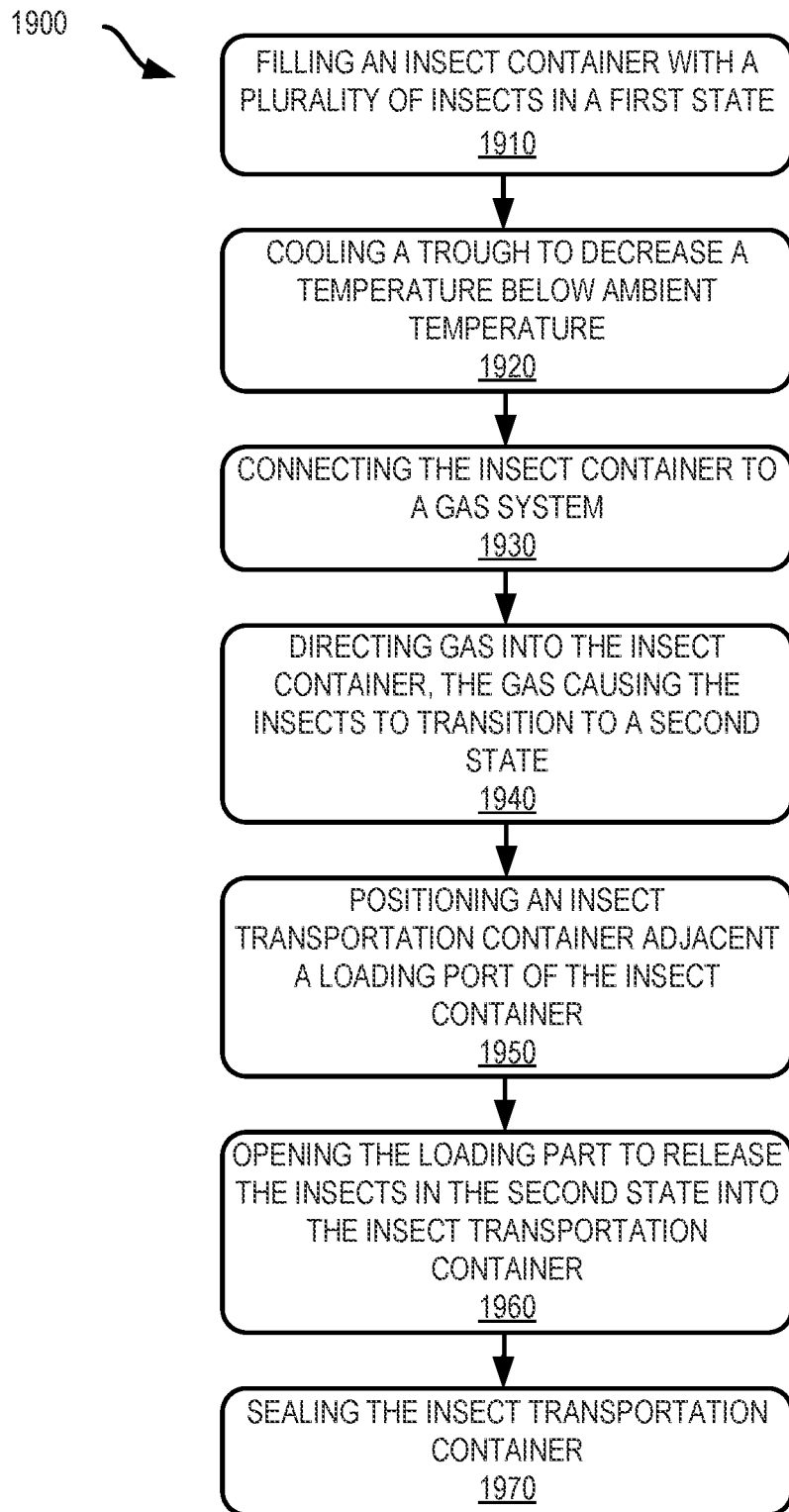
FIG. 19 illustrates a flowchart showing a process for packing insects into an insect transportation container, according to at least some examples.

Referring now to FIG. 19, FIG. 19 illustrates a flowchart showing a process 1900 for packing insects into an insect transportation container 100, according to at least some examples. The process 1900 may be performed using a system 200 as described with respect to FIGS. 5-7. The insect container may be an insect transportation container 100 as described with respect to FIGS. 1-4.

At 1910, the process 1900 includes filling an insect container with a plurality of insects in a first state. The insect container may be the insect dispenser 206 and the insect dispenser 206 may be filled with insects from a rearing system. The insects are introduced in to the insect container in a first state, where the insects are active. In some examples, the insects may be in a dormant state when introduced into the insect container. In some examples, the insects may be introduced into the insect container at a pupal stage or other early developmental stage and subsequently develop into their final insect stage within the insect container.

At 1920, the process 1900 includes cooling a trough to decrease a temperature within the trough below an ambient temperature. The trough may be cooled by a cooling system directly including a refrigeration system, heat exchanger, or other such heat management system. In some examples, the trough may be cooled by introducing a cooled gas into the trough. The temperature within the trough may be reduced to around or below eight degrees Celsius.

At 1930, the process 1900 includes connecting the insect container filled with insects to a gas system positioned adjacent the trough. The gas system may be a gas inlet 204 as described with respect to system 200 that provides a flow of refrigerated gas into the insect dispenser 206, such as refrigerated air from the refrigeration system 230 or may be a gas system that provides a knockdown gas into the insect container.

At 1940, the process 1900 includes directing gas, via the gas system, into the insect container, the gas causing the insects to transition to a second state. The insects in their first state may be active and the second state may be a dormant state for the insects. The gas may be cooled, in which case the temperature within the insect container may drop to a level such that the insects enter a dormant state. In some examples the gas may be a knockdown gas (e.g., carbon dioxide, nitrogen, or any other suitable substitute for oxygen that causes the insects to change to a dormant state without causing prolonged injury to the insects).

At 1950, the process 1900 includes positioning an insect container adjacent a loading port of the insect container. The insect container may be an insect transportation container 100. The insect container may be positioned vertically below the loading port. In some examples, the insect container may be positioned by advancing a conveyor system through the trough and stopping the conveyor system when a sensor within the trough detects that the insect container is adjacent the loading port.

At 1960, the process 1900 includes opening the loading port to release the insects in the second state into the insect container. the insects may be released to fall, under gravity, through the loading port and into the insect container. In some examples, the insects may be driven through the loading port by a gas, such as the gas inserted into the insect container.

At 1970, the process 1900 includes sealing the insect container. This may include closing a lid or securing two parts of an insect container. The securing of the insect container may be accomplished using the actuators 456 and 460 and plates 458 and 454 as described with respect to FIGS. 15-17 above.

It should be appreciated that the blocks described above have been discussed in a particular order, however, it should be appreciated that other orderings of the blocks may be used in some examples. For example, blocks 1930-1940 may be performed before block 1920. Similarly, block 1950 may be performed any time before block 1960. Further, in some examples, one or more blocks may be omitted. For example, in some examples, block 1920 may be omitted. Still other variations are contemplated within the scope of the present application.

Figure 20:
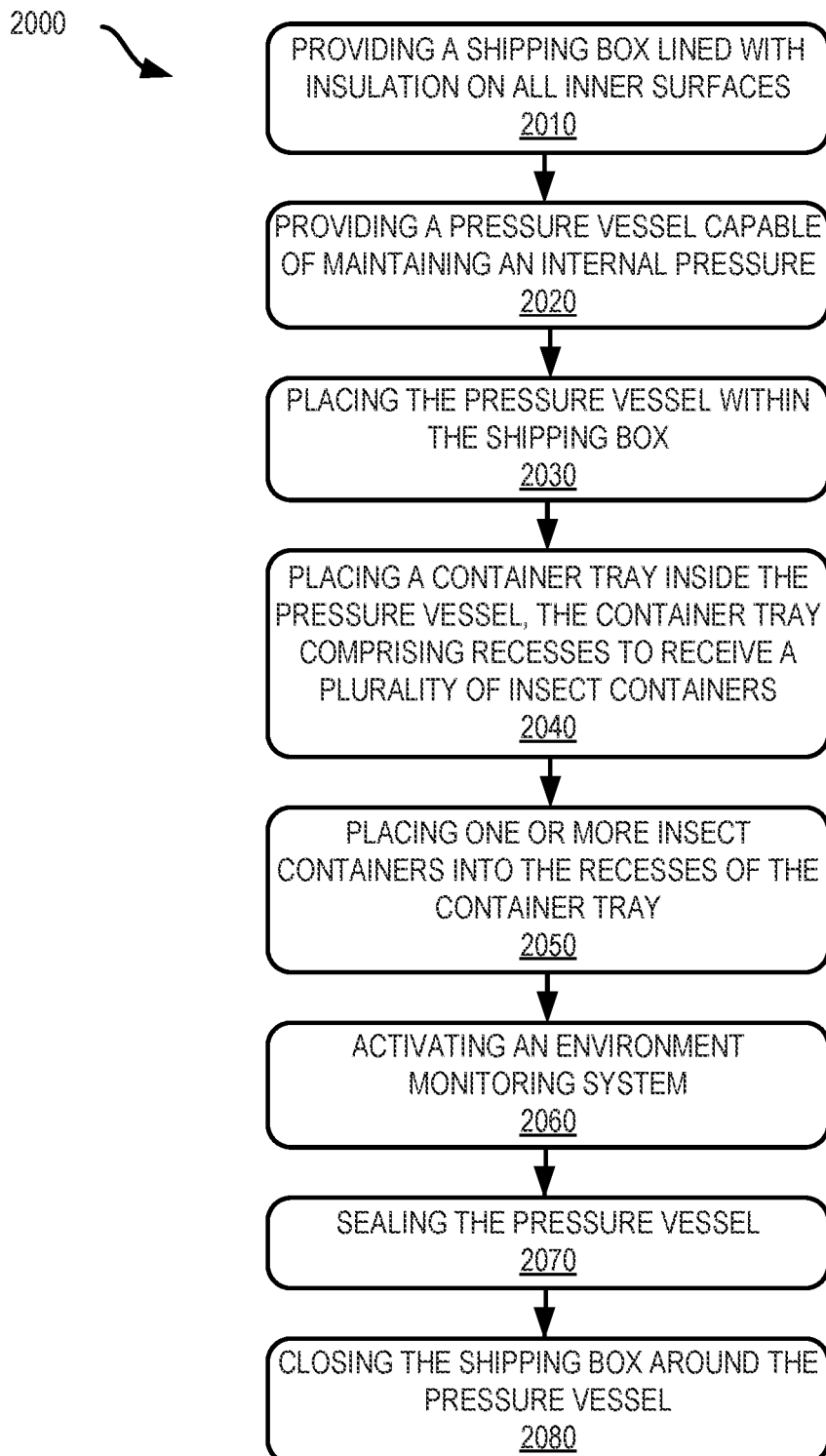
FIG. 20 illustrates a flowchart showing a process for packing insects into a packaging system for transportation, according to at least some examples.

FIG. 20 illustrates a flowchart showing a process 2000 for packing insects into a packaging system for transportation, according to at least some examples. The packaging system may be the packaging system of FIGS. 8-11.

At 2010, the process 2000 includes providing a shipping box lined with insulation on all inner surfaces. The shipping box may be the package 302 of FIGS. 8-11 including the insulation 304 and the cooling device 306.

At 2020, the process 2000 includes providing a pressure vessel capable of maintaining an internal pressure against varying external pressures. The pressure vessel may be the pressure vessel 308 of FIGS. 8-11.

At 2030, the process 2000 includes placing the pressure vessel within the shipping box. The pressure vessel may fit within the shipping box, including the insulation and cooling device such that a minimum amount of air is contained within the shipping box, i.e., the pressure vessel, insulation, and cooling device occupy nearly the entire inner volume of the shipping box.

At 2040, the process 2000 includes pacing a container tray inside the pressure vessel, the container tray including recesses to receive a plurality of insect containers. The container tray may be the tray 350 shown in FIG. 10 and the insect containers may be the insect transportation container 100 of FIGS. 1-4.

At 2050, the process 2000 includes placing one or more insect containers into the recesses of the container tray. In some examples, the process 2000 may also further include placing additional container trays and insect containers within the pressure vessel to fill an internal volume of the pressure vessel.

At 2060, the process 2000 includes activating an environment monitoring system. The environment monitoring system may include humidity, temperature, pressure, oxygen, and carbon dioxide sensors as described herein. Additionally, the environment monitoring system may include active components such as a carbon dioxide scrubbing system and an oxygen production system as described with respect to FIGS. 8-11 above. The environment monitoring system may include an on-board computing device in communication with the various sensors and active components of the system that may also be activated. In some examples, the process 2000 further includes adjusting an environmental parameter within the pressure vessel based on data from the environment monitoring system, such as by receiving a temperature reading and adjusting control of the cooling device or adjusting a rate of oxygen generation in response to a change in pressure or oxygen levels within the pressure vessel.

At 2070, the process 2000 includes sealing the pressure vessel to isolate the internal environment of the pressure vessel against an external environment. In some examples, the pressure within the pressure vessel may be set to a particular pressure level by introducing or removing air from within the pressure vessel after sealing. In some examples, a pressure level within the pressure vessel may be increased by around three to five pounds per square inch by introducing additional oxygen gas or oxygen mixed gas after sealing the pressure vessel. In some examples, the pressure may be increased more than three to five pounds per square inch or less than three to five pounds per square inch. The increase in pressure results in additional oxygen molecules within the pressure vessel for insects to consume during transportation. The increased pressure system within the pressure vessel may work in conjunction with the carbon dioxide scrubbing device described above without the need to generate additional oxygen, and instead only scrubs carbon dioxide during transportation.

At 2080, the process 2000 includes closing the shipping box around the pressure vessel and shipping the system.

It should be appreciated that the blocks described above have been discussed in a particular order, however, it should be appreciated that other orderings of the blocks may be used in some examples. For example, blocks 2040-2050 may be performed before block 2030. Similarly, block 2060 may be performed any time before block 2070. Further, in some examples, one or more blocks may be omitted. For example, in some examples, block 2080 may be omitted. Still other variations are contemplated within the scope of the present application.

Figure 21:
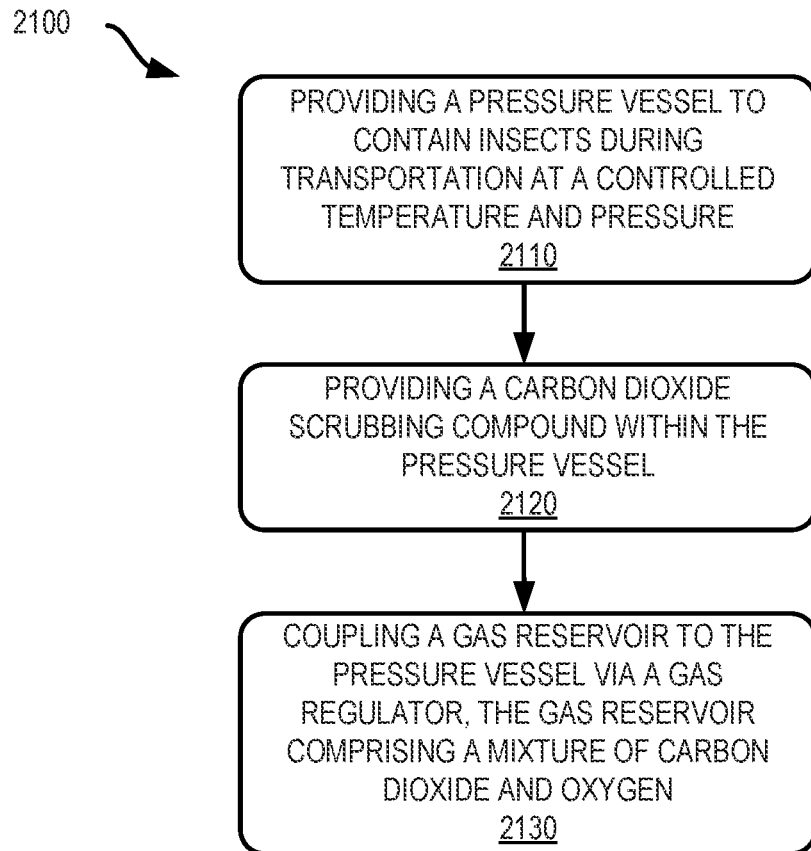
FIG. 21 illustrates a flowchart showing a process for scrubbing carbon dioxide within a packaging system for transporting live insects, according to at least some examples.

FIG. 21 illustrates a flowchart showing a process 2100 for scrubbing carbon dioxide within a packaging system for transporting live insects, according to at least some examples. The packaging system may include the packaging system 300 of FIGS. 8-11 and may include a system for scrubbing carbon dioxide, such as the carbon dioxide scrubber 354.

At 2110, the process 2100 includes providing a pressure vessel to contain insects during transportation at a controlled temperature and pressure. The pressure vessel may be pressure vessel 308 sealed against an external environment.

At 2120, the process 2100 includes providing a carbon dioxide scrubbing compound within the pressure vessel. the carbon dioxide scrubbing compound may include a passive scrubbing element such as soda lime. In some examples, the carbon dioxide scrubbing compound may also include a circulation fan for circulating air within the pressure vessel. In some examples, the carbon dioxide scrubbing compound may include an active carbon dioxide scrubbing device.

At 2130, the process 2100 includes coupling a gas reservoir to the pressure vessel via a gas regulator, the gas reservoir including a mixture of carbon dioxide and oxygen. The gas regulator may be set to introduce gas into the pressure vessel from the reservoir to maintain an internal pressure of the pressure vessel as carbon dioxide gas within the pressure vessel is scrubbed and the pressure decreases. The mixture of carbon dioxide and oxygen may be mixed at a ratio of twenty percent oxygen to eighty percent carbon dioxide. In some examples, the gas reservoir may include a mixture of oxygen with another gas, such as nitrogen.

It should be appreciated that the blocks described above have been discussed in a particular order, however, it should be appreciated that other orderings of the blocks may be used in some examples. For example, block 2130 may be performed before block 2120. Further, in some examples, one or more blocks may be omitted. For example, in some examples, block 2120 may be omitted. Still other variations are contemplated within the scope of the present application.

Figure 22:
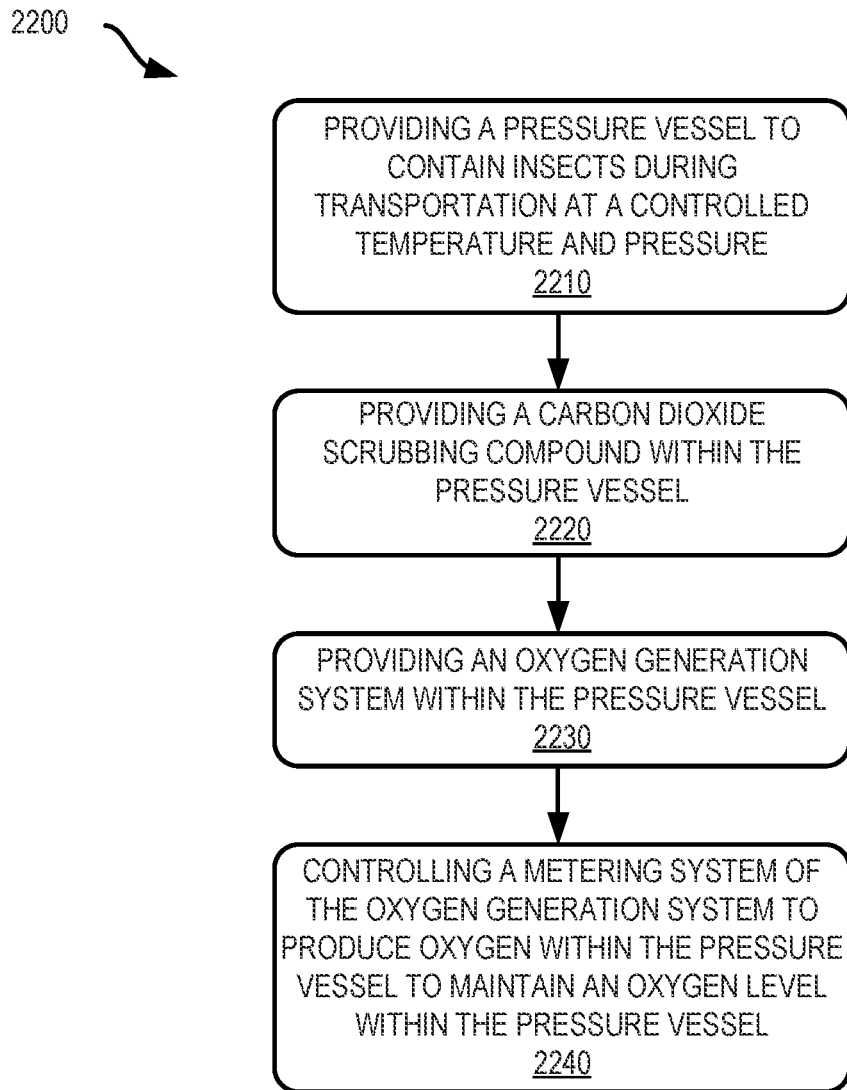
FIG. 22 illustrates a flowchart showing a process for scrubbing carbon dioxide within a packaging system for transporting live insects, according to at least some examples.

FIG. 22 illustrates a flowchart showing a process 2200 for scrubbing carbon dioxide within a packaging system for transporting live insects, according to at least some examples. The packaging system may include the packaging system 300 of FIGS. 8-11 and may include a system for scrubbing carbon dioxide, such as the carbon dioxide scrubber 354.

At 2210, the process 2200 includes providing a pressure vessel to contain insects during transportation at a controlled temperature and pressure. The pressure vessel may be pressure vessel 308 sealed against an external environment.

At 2220, the process 2200 includes providing a carbon dioxide scrubbing compound within the pressure vessel. the carbon dioxide scrubbing compound may include a passive scrubbing element such as soda lime. In some examples, the carbon dioxide scrubbing compound may also include a circulation fan for circulating air within the pressure vessel. In some examples, the carbon dioxide scrubbing compound may include an active carbon dioxide scrubbing device.

Figure 11:
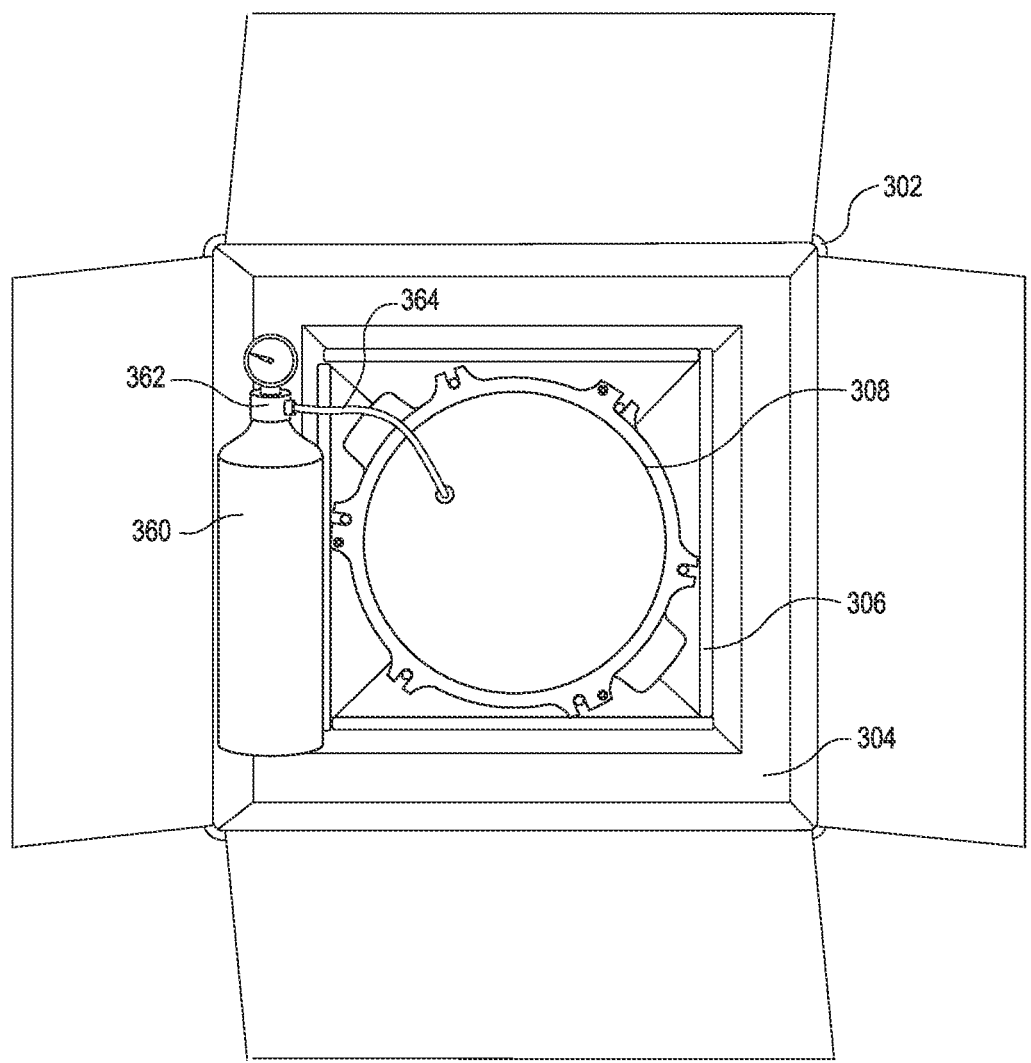
FIG. 11 illustrates a live insect transportation system including a gas supply system, according to at least some examples.
Figure 12:
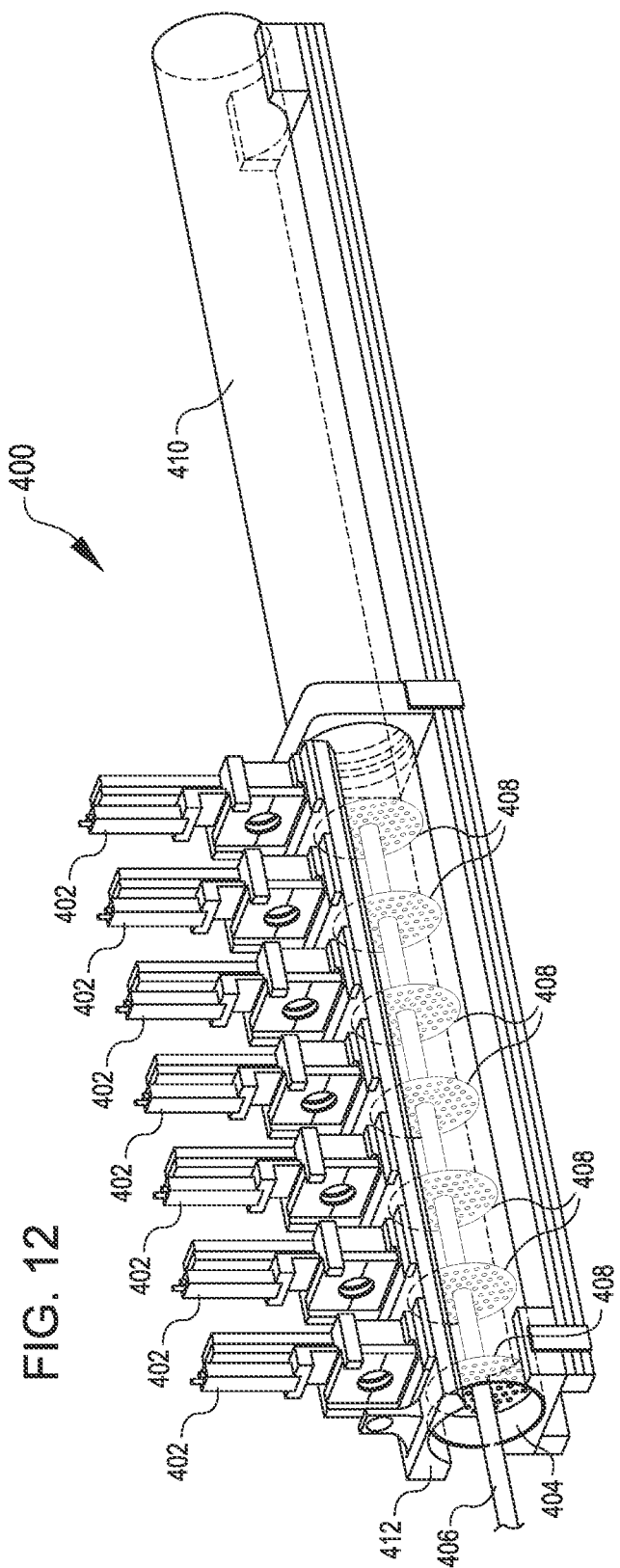
FIG. 12 illustrates an unpacking device for unpacking insects from insect transportation containers and loading the insects into an insect release device, according to at least some examples.

At 2230, the process 2200 includes providing an oxygen generation system within the pressure vessel. In some examples, the oxygen generation system may include a gas reservoir as shown in FIG. 11. In some examples, the oxygen generation system may include a system that produces oxygen by reacting reactants. The reactants may include hydrogen peroxide and a reactant such as platinum. Any suitable reactants that produce oxygen when reacted together may be suitable for use with the oxygen generation system.

At 2240, the process 2200 includes controlling a metering system of the oxygen generation system to produce oxygen within the pressure vessel to maintain a n oxygen level within the pressure vessel. Controlling systems for reactant-based oxygen production systems may include a sensor array within the pressure vessel. The sensor array may include temperature, humidity, pressure, oxygen, and carbon dioxide sensors. The sensor array may be in communication with an on-board computing device of the shipping system. In the case of oxygen production, the oxygen and/or carbon dioxide sensors may be in communication with the computing device. The computing device may be a computing device 2400 as shown and described with respect to FIG. 2400. The computing device 2400 may be configured to cause a reactant based oxygen production system to produce oxygen when the oxygen level detected by the oxygen sensor drops below a threshold level. In some examples, the computing device may cause the oxygen production system to maintain a constant oxygen level within the pressure vessel.

With respect to a reactant-based oxygen production system, the system may rely on a reaction between a reservoir of hydrogen peroxide and a reactant, such as platinum. The reaction between the two produces water and oxygen. By controlling a flow of hydrogen peroxide into contact with the reactant, the rate of oxygen production may be controllable by the computing device. For example, the use of a controllable valve allows the computing device to adjust the flow rate of hydrogen peroxide and thereby control the rate of oxygen production.

It should be appreciated that the blocks described above have been discussed in a particular order, however, it should be appreciated that other orderings of the blocks may be used in some examples. For example, block 2230 may be performed before block 2220. Further, in some examples, one or more blocks may be omitted. For example, in some examples, block 2240 may be omitted. Still other variations are contemplated within the scope of the present application.

Figure 23:
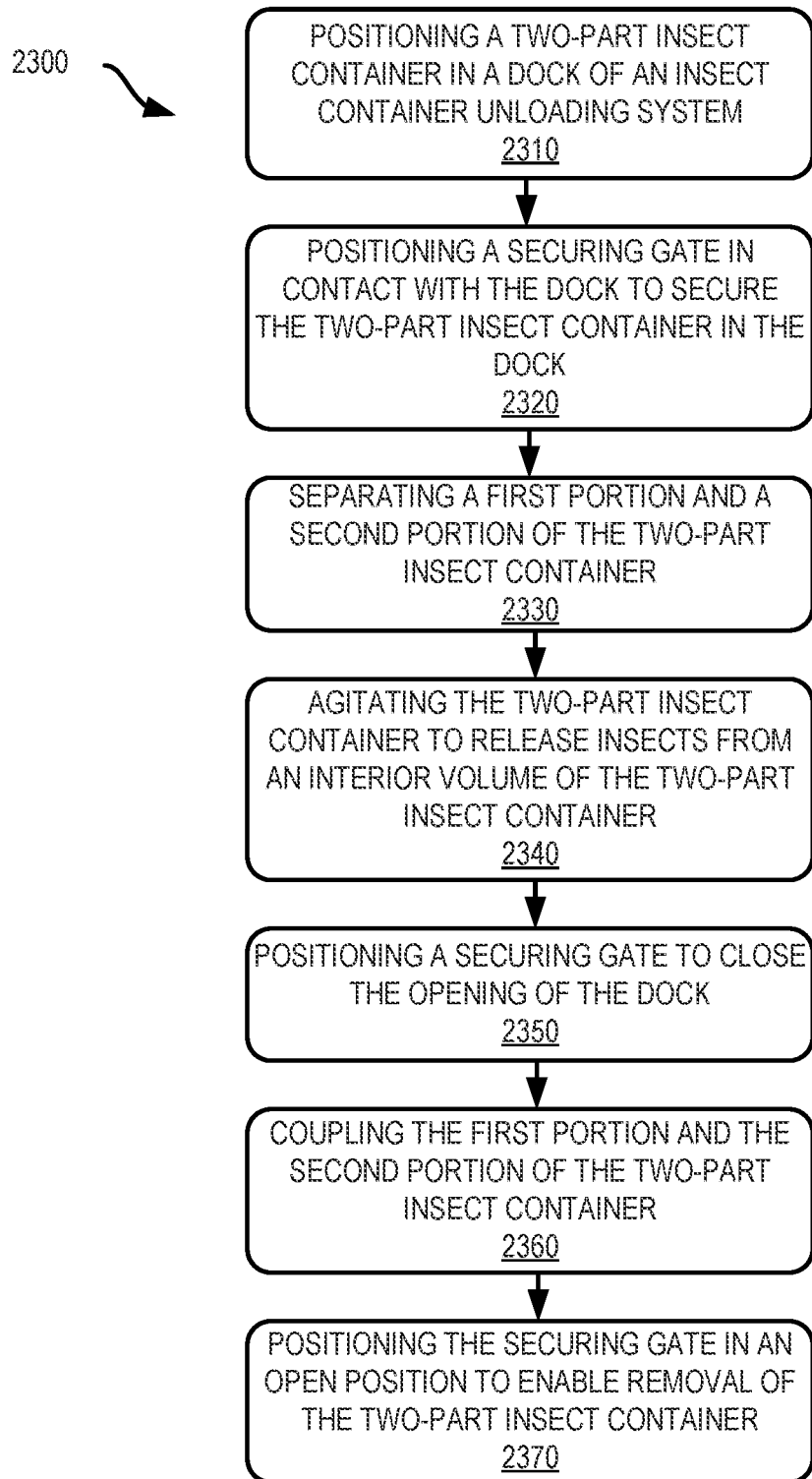
FIG. 23 illustrates a flowchart showing a process for unpacking insects from an insect transportation container using an unpacking device, according to at least some examples.

FIG. 23 illustrates a flowchart showing a process 2300 for unpacking insects from an insect container using an unpacking device, according to at least some examples. The process 2300 may be implemented by an unpacking system, such as the unpacking system 400 and follow the steps outlined in FIGS. 13-18 for unpacking insects from an insect container. The insect container may be the insect transportation container 100 of FIGS. 1-4.

At 2310, the process 2300 includes positioning an insect container in a dock of an insect container unloading system. The insect container may be placed in a dock 450 of the unpacking device 402 of the unpacking system 400. The unpacking device 402 may be one unpacking device of several unpacking devices 402 as part of an unpacking system 400. The insect container device is initially filled with insects in an internal void thereof. The step performed at 2310 is illustrated by FIGS. 13-14.

At 2320, the process 2300 includes positioning a securing gate in contact with the dock to secure the insect container in the dock. The securing gate may be the upper gate 470 of securing device 402. The securing gate may be lowered into a closed position to secure the insect container in the dock as illustrated in FIG. 15. The securing gate may be positioned by actuating a vertical actuator (e.g., the vertical actuator 474).

At 2330, the process 2300 includes separating a first portion and a second portion of the insect container. The step at 2330 may be performed as described with respect to the opening actuators of FIG. 15. In particular, the opening actuators 456 and 460 move the plates 454 and 458 from the closed position to the open position. In moving from the closed position to the open position, the plates 454 and 458 apply a force to one part of the insect container to drive the insect container into separate components and allow release of the insects stored therein through the passageway 452 into the receiving chamber 404.

At 2340, the process 2300 includes agitating the insect container to release insects from an interior volume of the insect container. The step at 2340 may be performed as described with respect to FIG. 16. In particular, after the insect container is opened, the agitating device 464 is rotated by the motor 462. The rotation of the motor 462 drives the agitating device 464 and causes the agitating device to apply a rotational force to the insect container. The rotational force causes the insect container to spin within the dock 450 and agitate any insects that may cling to the foam inserts to fall out and through the passageway 452. Additionally, an air nozzle positioned in the upper gate 470 may direct a blast of air towards the passageway 452 between the two portions of the insect container to drive any remaining insects through the passageway 452.

At 2350, the process 2300 includes positioning a sealing gate to close the opening of the dock. The sealing gate may include the passageway seal 466 and the lifter 468 and positioning the sealing gate may include causing a vertical actuator to move the sealing gate from a first position to a second position. The step at 2350 includes the elements and movements described with respect to FIG. 17.

At 2360, the process 2300 includes coupling the first portion and the second portion of the insect container. The first portion and the second portion of the insect container may be coupled together as shown in FIG. 17, but actuating the opening actuators 456 and 460 to cause the plates 454 and 458 to apply a force to the first portion of the insect container and bring the insect container together.

At 2370, the process 2300 includes positioning the securing gate in an open position to enable removal of the insect container. This step is illustrated in FIG. 18 and includes actuating a vertical actuator to position the upper gate in an open position such that the insect container is free to remove from the unpacking device 402.

In some examples, the process 2300 may further include transferring insects from the receiving chamber 404 into a release device for release as part of the SIT program. In some examples this may include moving dividers to cause the insects to advance from the receiving chamber 404 into the release device 410.

It should be appreciated that the blocks described above have been discussed in a particular order, however, it should be appreciated that other orderings of the blocks may be used in some examples. For example, block 2340 may be performed before block 2330. Similarly, block 2360 may be performed before block 2350. Further, in some examples, one or more blocks may be omitted. For example, in some examples, blocks 2320 and 2370 may be omitted. Still other variations are contemplated within the scope of the present application.

Figure 24:
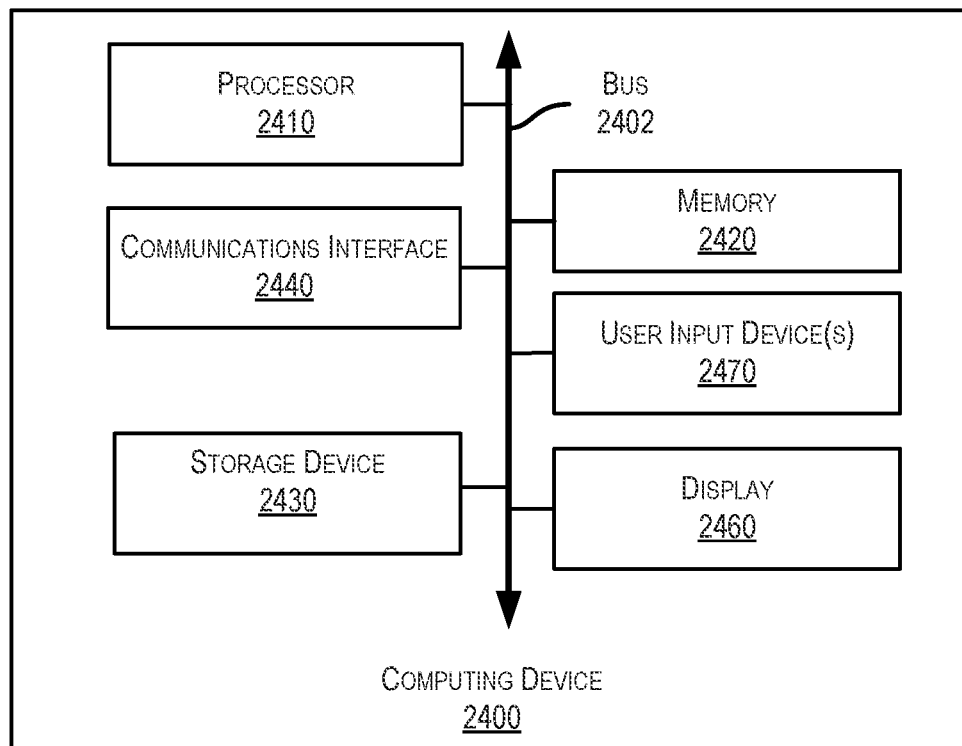
FIG. 24 illustrates a block diagram of a computing device for implementing processes and methods described herein, according to at least some examples.

Referring now to FIG. 24, computing device 2400 shows computing device 2400 suitable for use in example systems or methods for packing, transporting, and unpacking insects. For example, computing device 2400 may be an on-board computer of a packaging system, a computing device associated with an insect packing system, a computer associated with an unpacking system or other computing devices included herein. Computing device 2400 includes a processor 2410 which is in communication with the memory 2420 and other components of the computing device 2400 using one or more communications buses 2402. The processor 2410 is configured to execute processor-executable instructions stored in the memory 2420 to perform methods of example processes 1900, 2000, 2100, 2200, and 2300 described above with respect to FIGS. 19-23. The computing device 2400, in this example, also includes one or more user input devices 2470, such as a keyboard, mouse, touchscreen, microphone, etc., to accept user input. The computing device 2400 also includes a display 2460 to provide visual output to a user.

The computing device 2400 can include or be connected to one or more storage device 2430 that provides non-volatile storage for the computing device 2400. The storage device 2430 can store system or application programs and data used by the computing device 2400, such as software implementing the functionalities provided by the processes 1900, 2000, 2100, 2200, and 2300. The storage device 2430 might also store other programs and data not specifically identified herein.

The computing device 2400 also includes a communications interface 2440. In some examples, the communications interface 2440 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

Figure 26:
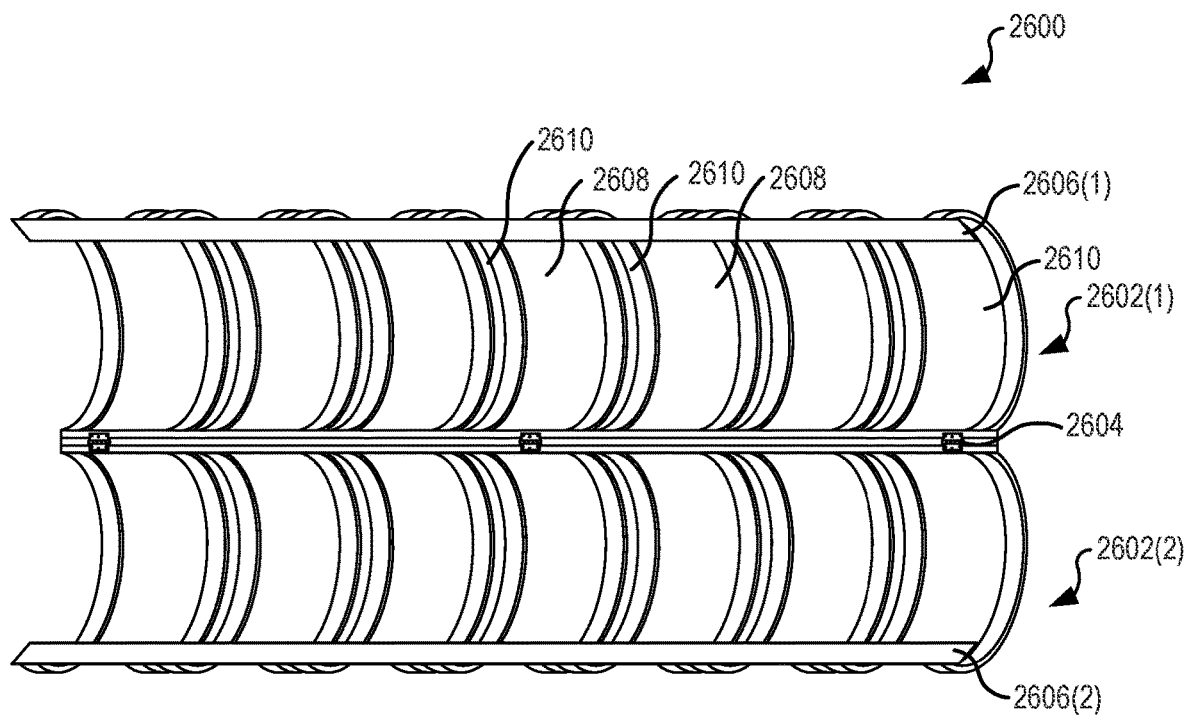
FIG. 26 illustrates an example tray for retaining a plurality of insect containers, according to at least some examples.

FIG. 26 illustrates an example tray 2600 for retaining a plurality of the insect containers 110, according to at least some examples. In this manner, the tray 2600 performs a similar function as the tray 350 described herein. The tray 2600 however includes a bottom section and a top section connected via a hinge. The orientation of the tray 2600 is linear, meaning that the insect containers 110 will be held in a linear orientation. Other orientations, including multiple rows and/or columns of insect containers 110 may be held in trays 2600 having such structure. The tray 2600 may be suitable for use in a flexible pressure vessel such as those shown in FIGS. 29, 30, 32, and 33.

The tray 2600 includes two corresponding semi-circular frames 2602 and 2602 generally from two rigid frames 2602(1) and 2602(2). The frames 2602 are each half of a circle such that when they are brought together they define a complete circle. Of course, other shapes and configuration that are non-circular are also possible. The frames 2602 includes connecting surfaces 2606(1) and 2606(2) that, when the tray 2600 is in a closed state, come into contact with each other. In some examples, the connecting surfaces 2606 may include means for retaining the two surfaces together. For example, snaps, hook and look, interference fit between grooves and bumps, or any other suitable fastener may be used. The frames 2602 each include a series of repeating curved ribs 2608 spaced to define container openings 2610. The ribs 2608 provide supportive structure to the tray 2600 and support the containers 110 when they are received into the openings 2610 between the rigs 2608.

The frames 2602 are connected via one or more hinges 204 disposed along back surfaces of the frames 2602. In some examples, the hinge 204 is formed as a live hinge. In any event, with the hinged connection between the frames 2602, the tray 2600 can move between an open state (as shown) and a closed state, e.g., on in which the containers 110 are held within the tray 2600.

Figure 27:
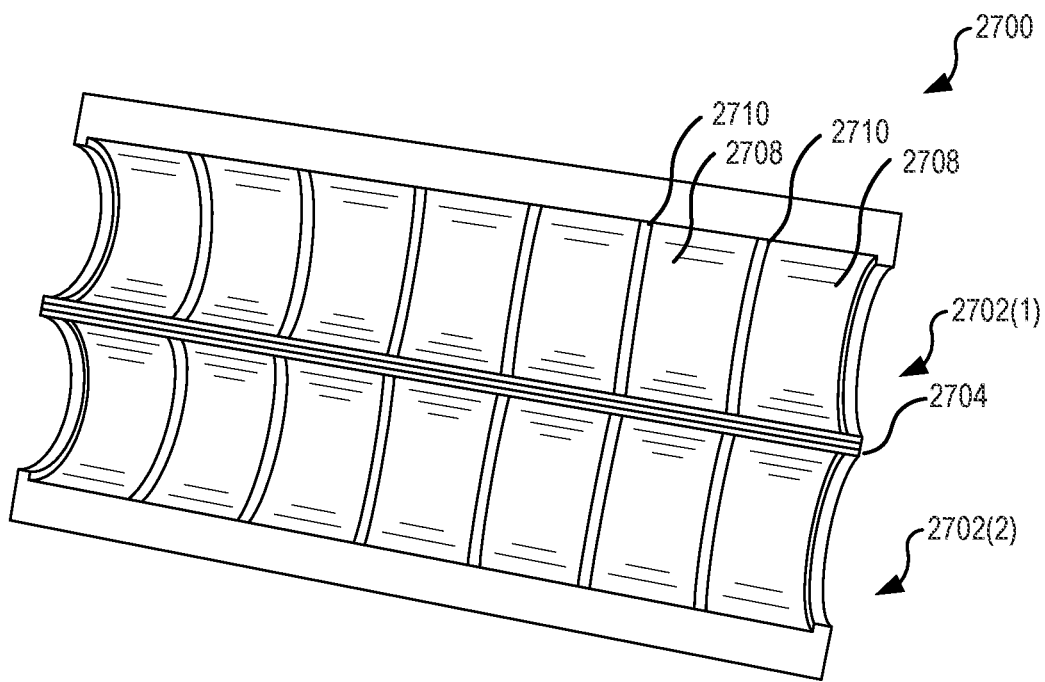
FIG. 27 illustrates an example tray for retaining a plurality of insect containers in an open state, according to at least some examples.
Figure 28:
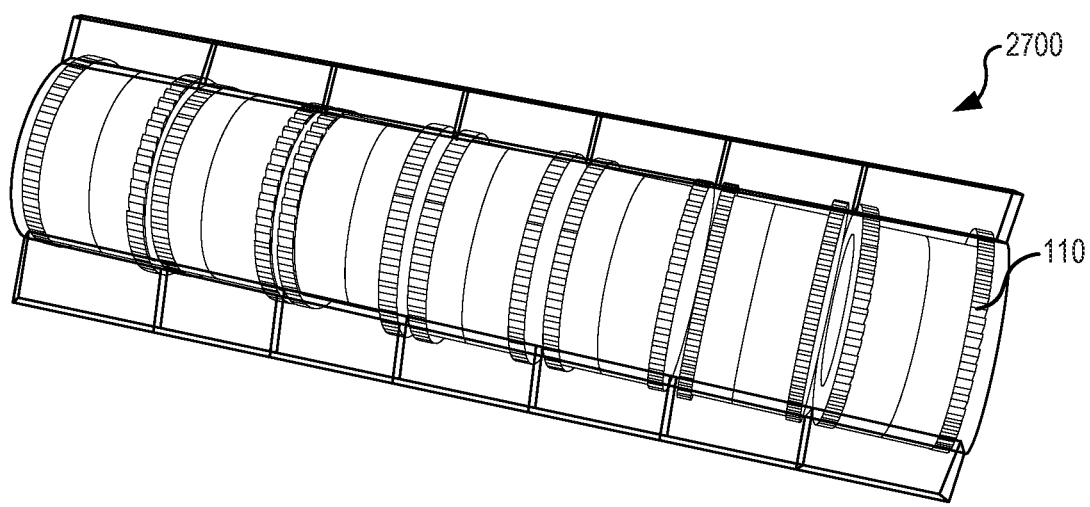
FIG. 28 illustrates the example tray from FIG. 27 in a closed state and including a plurality of insect containers, according to at least some examples.

FIG. 27 illustrates an example tray 2700 for retaining a plurality of the insect containers 110 in an open state, according to at least some examples. FIG. 28 illustrates the example tray 2700 in a closed state and including insect containers 110, according to at least some examples. The tray 2700 performs a similar function as the tray 2600, but includes a different structure. In particular, the tray 2700 is formed from sheet material that has been extruded, stamped, or otherwise formed to define the tray 2700. The tray 2700 generally is defined to include two halves 2702(1) and 2702(2), like clam shell. In some examples, the two halves 2702 are formed separately and joined together at a hinge 2704. In some examples, the tray 2700 is formed from a single piece of material such that the two halves 2702 form a unitary structure. The hinge 2704 may include a live hinge formed from the same or similar material as the halves 2702. In some examples, the hinge 2704 is formed from one or more structures that attached to individual parts of the halves 2702. Each halve 2702 includes a series of alternating ridges 2710 and recesses 2608. The recesses 2710 are configured to receive the insect containers 110, as shown in FIG. 28. The ridges 2710 function to add structural rigidity to the tray 2700 and separate recess 2608 (and one insect container 110) from another. In the closed state illustrated in FIG. 28, the insect containers 110 have been placed into the recesses 2608 of the half 2702(2) and the half 2702(1) has been rotated about the hinge to enclose the insect containers 110 within the tray 2700. This functions to securely hold the insect containers 110 and keep them from opening during transport.

Figure 29:
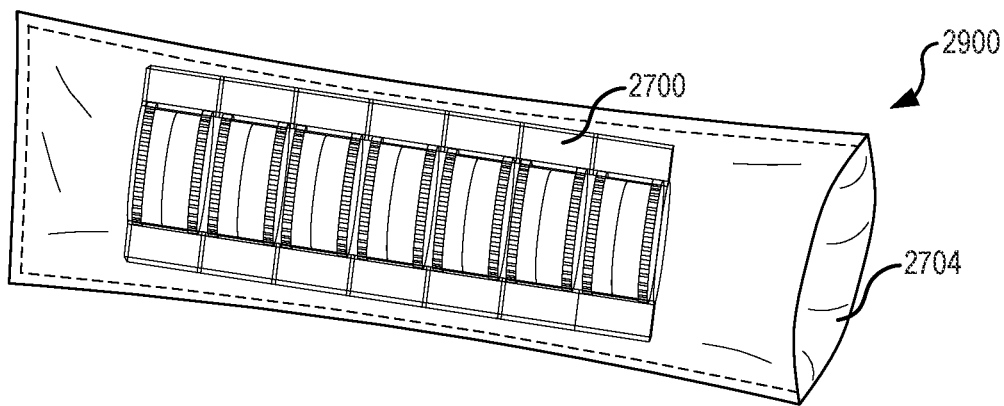
FIG. 29 illustrates an example flexible pressure vessel in a deflated state and including the example tray from FIG. 28, according to at least some examples.
Figure 30:
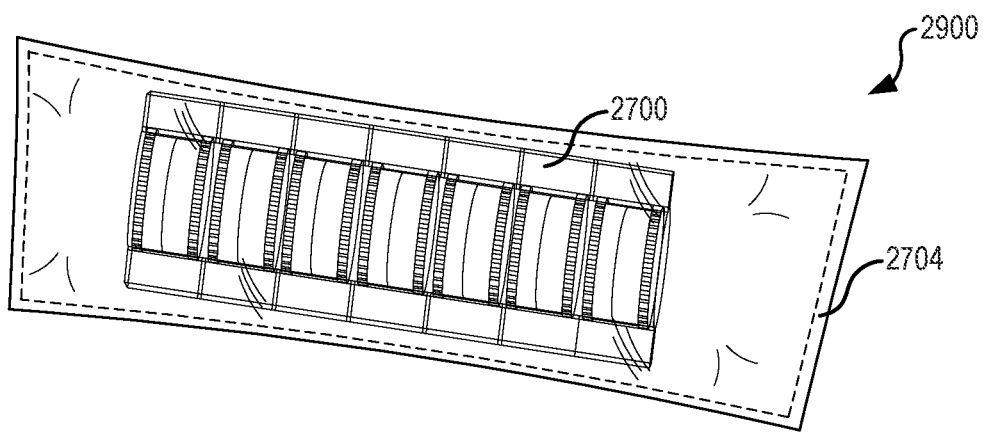
FIG. 30 illustrates the example flexible pressure vessel from FIG. 29 in an inflated state, according to at least some examples.

FIG. 29 illustrates an example flexible pressure vessel 2900 in a deflated state and including the example loaded tray 2700 from FIG. 28, according to at least some examples. FIG. 30 illustrates the example flexible pressure vessel 2900 in an inflated state, according to at least some examples. The pressure vessel 2900 may be formed from a flexible material such any suitable polyethylene or other suitable flexible material including, for example, polyethylene—Low Density, rubbers, and the like. The pressure vessel 2900 includes an opening 2902 defined at one end. The opening 2902 and the pressure vessel 2900 are sized to accommodate one or more trays 2700 holding one or more insect containers. As illustrated, a single tray 2700 having an elongated shape has been placed into the interior of the pressure vessel 2900. As shown in FIG. 30, after loading, the pressure vessel 2900 may be inflated and the openings 2902 may be sealed. In some examples, the pressure vessel 2900 is overinflated with a suitable gas mixture, air, oxygen, or the like to provide air for the insects within the insect containers. Inflating the pressure vessel 2900 also provides for compliance and protection of the tray 2700 during shipping. When access to the tray(s) 2700 is required, the pressure vessel 2900 may be cut open and disposed of.

Figure 31:
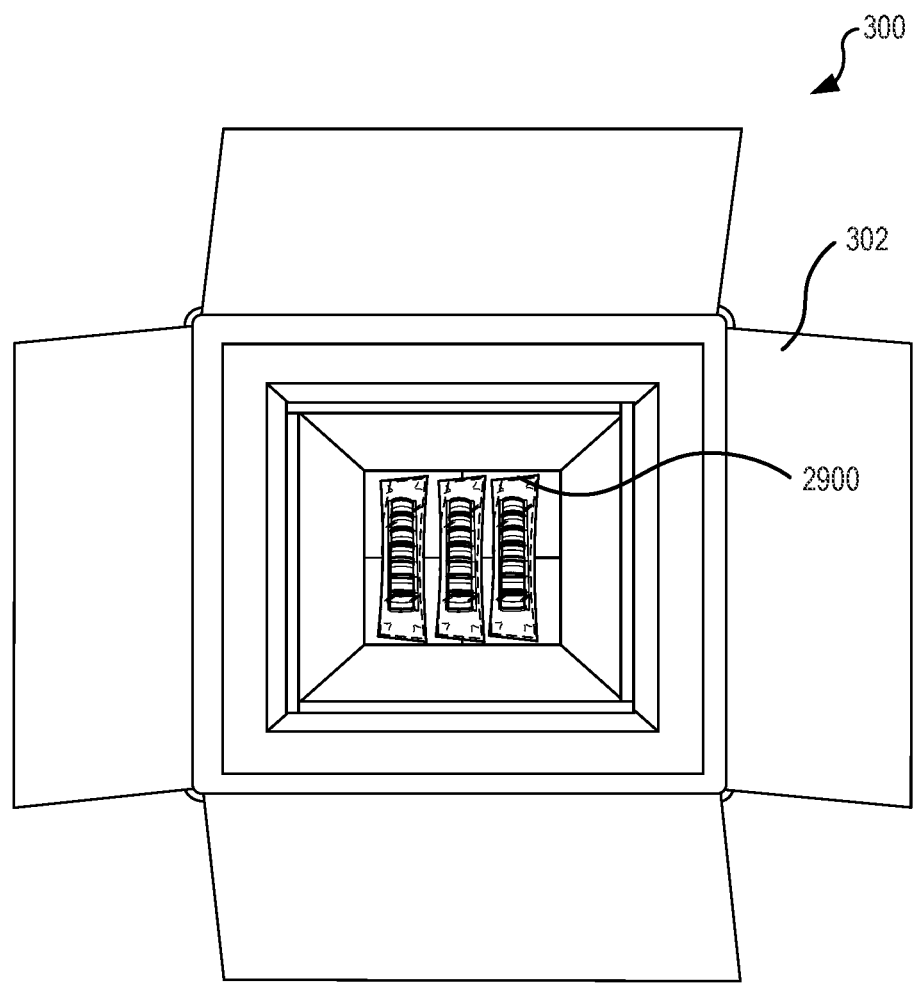
FIG. 31 illustrates a live insect transportation packaging system including a plurality of flexible pressure vessels from FIG. 30, according to at least some examples.

As shown in FIG. 31, the pressure vessels 2900 may be placed within the live insect transportation packaging system 300. Thus, the pressure vessels 2900 and 3200 (described hereafter) may be used in place of the rigid pressure vessel 308. Depending on the size of the package 302 and the pressure vessels 2900 or 3200, multiple pressure vessels may be stacked within an interior of the package 302. The other elements of the system 300 may also be provided within the package 302, as described previously.

Figure 32:
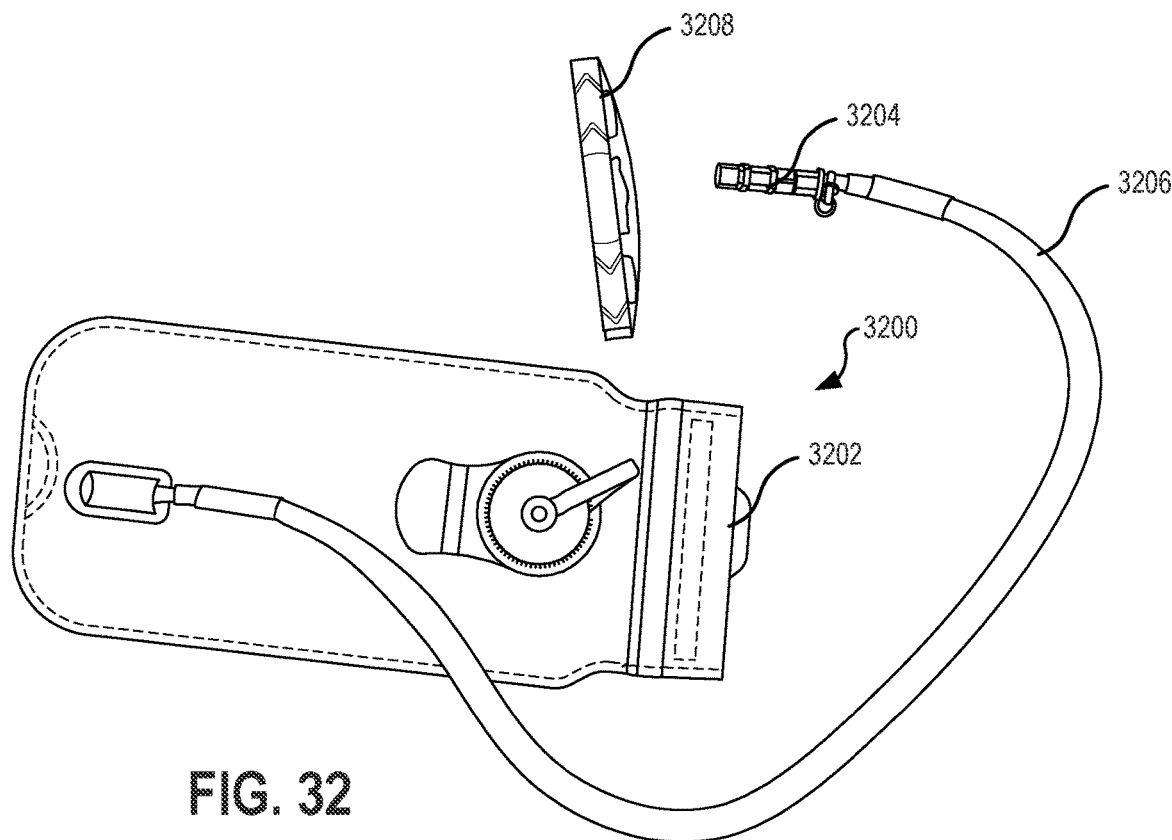
FIG. 32 illustrates an example flexible pressure vessel in a deflated state, according to at least some examples.
Figure 33:
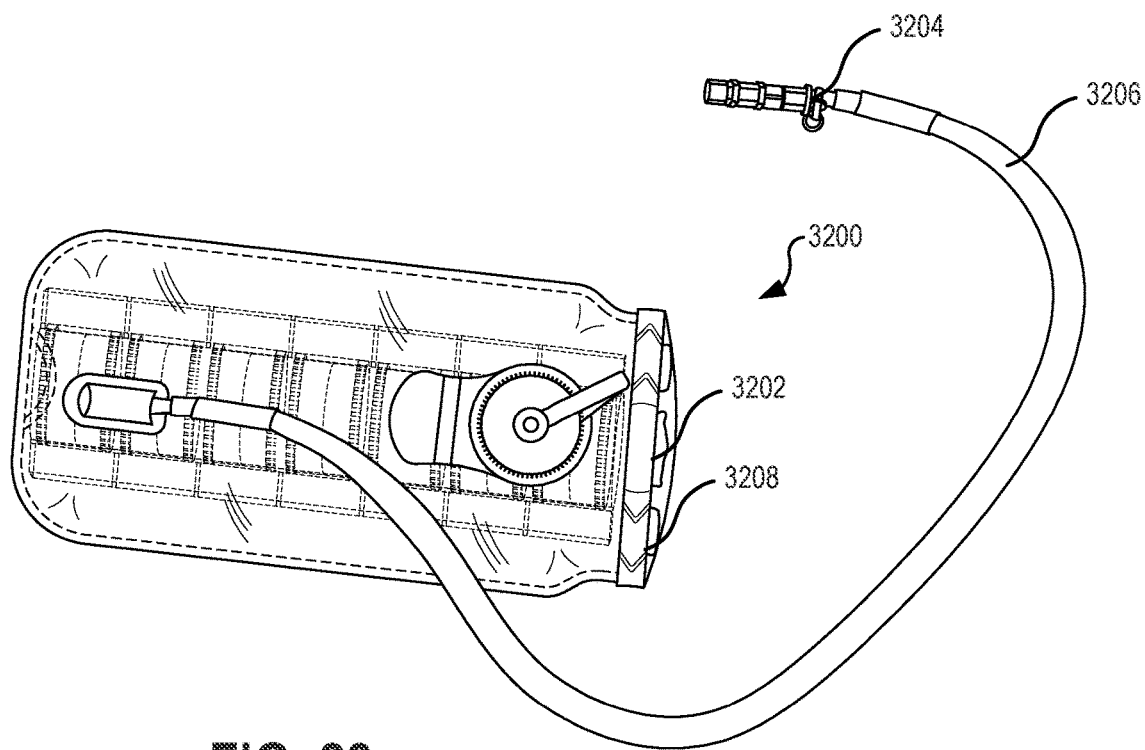
FIG. 33 illustrates the example flexible pressure vessel from FIG. 32 in an inflated state and including the example tray from FIG. 28, according to at least some examples.

FIG. 32 illustrates an example flexible pressure vessel 3200 in a deflated state, according to at least some examples. FIG. 33 illustrates the example flexible pressure vessel 3200 in an inflated state and including the tray 2700, according to at least some examples. Like the pressure vessel 2900, the pressure vessel 3200 may include a flexible body. Unlike the pressure vessel 2900, however, the pressure vessel 3200 may be reusable. For example, the pressure vessel 3200 includes a resealable opening 3202 and a valve 3204 in pneumatic communication with the pressure vessel 3200 via pipe 3206. The pressure vessel 3200 also includes a sealer 3208 to seal the resealable opening 3202. Other mechanisms for sealing the resealable opening 3202 may also be used, e.g., roll top, interlocking sliding locks, and the like. The valve 3204 may be used to introduce gas, a described with respect to pressure vessel 2900, into the pressure vessel 3200 after the opening 3202 has been sealed. In some examples, the valve 3204 is connected directly to the pressure vessel 3200, rather than using the pipe 3206.

While some examples of methods and systems herein are described in terms of software executing on various machines, the methods and systems may also be implemented as specifically configured hardware, such as field-programmable gate array (FPGA) specifically to execute the various methods. For example, examples may be implemented in digital electronic circuitry, or in computer hardware, firmware, software, or in a combination thereof. In one example, a device may include a processor or processors. The processor includes a computer-readable medium, such as a random access memory (RAM) coupled to the processor. The processor executes computer-executable program instructions stored in memory, such as executing one or more computer programs. Such processors may include a microprocessor, a digital signal processor (DSP), an application-specific integrated circuit (ASIC), field programmable gate arrays (FPGAs), and state machines. Such processors may further include programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may include, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may include code for carrying out one or more of the methods (or parts of methods) described herein.

In the following, further examples are described to facilitate the understanding of the present disclosure.

Example 1. In this example, there is provided an insect container, including:
    a first container portion and a second container portion, the first container portion configured to be coupled to the second container portion to enclose a volume, each of the first and second container portions including:
    a backing plate, wherein:
    the respective backing plate defines a plurality of vent holes providing a conduit for air to travel through the backing plate to provide air to insects when the insects are stored in the insect container; and
    the respective backing plate is rotatable about a respective axis of rotation perpendicular to the backing plate when the insect container is in an open configuration; and
    a wall extending from a first surface of the respective backing plate in a direction parallel to the respective axis of rotation, the wall defining a container perimeter and including a non-rotating coupling feature at a distal end of the wall from the backing plate, wherein the backing plate and the wall together define a cavity, and wherein the non-rotating coupling feature of the first container portion and the non-rotating coupling feature of the second container portion enable the first and second container portions to couple together to fully enclose a volume including the cavity and prevent relative rotation of the first and second container portions.

Example 2. In this example, there is provided an insect container of any of the preceding or subsequent examples, wherein each of the plurality of vent holes have a cross-sectional dimension less than a size of representative insect to be stored inside the insect container.

Example 3. In this example, there is provided an insect container of any of the preceding or subsequent examples, wherein each backing plate includes an engaging surface at a perimeter of the respective backing plate, and wherein the respective engaging surface defines a set of protrusions extending in a plane defined by the backing plate radially away from a center of the backing plate, and wherein the set of protrusions are configured to engage with a rotating mechanism at the respective engaging surface to rotate the respective first or second container portion.

Example 4. In this example, there is provided an insect container of any of the preceding or subsequent examples, wherein the set of protrusions includes gear teeth around the perimeter of the respective backing plate, and wherein each respective backing plate is circular.

Example 5. In this example, there is provided an insect container of any of the preceding or subsequent examples, wherein the container perimeter forms a circular shape.

Example 6. In this example, there is provided an insect container of any of the preceding or subsequent examples, wherein the container perimeter is concentric with the perimeter of the backing plate.

Example 7. In this example, there is provided an insect container of any of the preceding or subsequent examples, wherein the container perimeter has a first diameter and the backing plate has a second diameter, the first diameter smaller than the second diameter.

Example 8. In this example, there is provided an insect container of any of the preceding or subsequent examples, wherein the non-rotating coupling feature of the first container portion and the non-rotating coupling feature of the second container portion interface with each other to prevent rotation of the first container portion relative to the second container portion when coupled together.

Example 9. In this example, there is provided an insect container of any of the preceding or subsequent examples, wherein at least one of the first container portion or the second container portion includes a compressible foam insert.

Example 10. In this example, there is provided an insect container of any of the preceding or subsequent examples, wherein the compressible foam insert includes an inner portion and an outer portion, the inner portion concentric with the outer portion with the inner portion having a first height and the outer portion having a second height, the second height greater than the first height.

Example 11. In this example, there is provided an insect container, including:
- a first container portion, including:
  - a first circular backing plate; and
  - a first raised wall extending from a first surface of the first circular backing plate, an edge of the first raised wall opposite the first circular backing plate including a first profile; and
- a second container portion, including:
  - a second circular backing plate; and
  - a second raised wall extending from a first surface of the second circular backing plate, an edge of the second raised wall opposite the second backing plate including a second profile, wherein the first profile and the second profile mate together to:
    - releasably interlock the first container portion and the second container portion;
    - prevent rotation of the first container portion with respect to the second container portion; and
    - wherein the first container portion and the second container portion define an interior volume configured to retain a population of insects when interlocked with each other.

Example 12. In this example, there is provided an insect container of any of the preceding or subsequent examples, wherein each of the first circular backing plate and the second backing plate comprise teeth formed around respective perimeters thereof, and wherein the teeth formed in the first circular backing plate and the second circular backing plate each comprise a series of gear teeth that enable rotation of the first circular backing plate and the second circular backing plate when engaged with a rotating mechanism having mating teeth.

Example 13. In this example, there is provided an insect container of any of the preceding or subsequent examples, wherein the first profile and the second profile each comprise a scalloped profile.

Example 14. In this example, there is provided an insect container of any of the preceding or subsequent examples, wherein the first profile includes a male connector and the second profile includes a female connector, wherein the male connector and the female connector releasably couple together to secure the first container portion and the second container portion together.

Example 15. In this example, there is provided an insect container of any of the preceding or subsequent examples, further including a retaining device including a flexible band to maintain the first container portion and the second container portion in contact with one another along the edge of the first raised wall and the second raised wall, respectively.

Example 16. In this example, there is provided an insect container of any of the preceding or subsequent examples, further including a foam insert, wherein an outer perimeter of the foam insert matches an inner perimeter of the first raised wall of the first container portion.

Example 17. In this example, there is provided an insect container of any of the preceding or subsequent examples, wherein the foam insert includes a raised edge around the outer perimeter of the foam insert such that the foam insert defines an insect support cavity.

Example 18. In this example, there is provided an insect container of any of the preceding or subsequent examples, wherein the first circular backing plate and the second circular backing plate each define a plurality of vent holes providing a conduit between the first surface and a second surface of the first circular backing plate and the second circular backing plate.

Example 19. In this example, there is provided an insect container of any of the preceding or subsequent examples, wherein the vent holes each have a cross-sectional dimension less than a cephalothorax diameter of an insect.

Example 20. In this example, there is provided an insect container of any of the preceding or subsequent examples, wherein each of the first circular backing plate and the second backing plate comprise teeth formed around respective perimeters thereof, and wherein the teeth of the first circular backing plate and the teeth of the second circular backing plate extend beyond an outer perimeter of the first raised wall and the second raised wall, respectively.

Example 21. In this example, there is provided a system for loading insect containers, including:
- a trough with a bottom and walls defining a volume to receive a plurality of insect containers for loading;
- an insect dispenser maintained in a position adjacent an upper opening of the trough and defining a gas port and an insect port in a wall thereof, the insect port selectively openable to enable loading and unloading of insects into the insect container; and
- an insect container positionable within the volume to retain insects during transportation, the insect container sized to receive insects from the insect dispenser through the insect port in a compact volume after cooling within the insect dispenser;

a gas system including a conduit coupled to gas port of the insect dispenser to direct gas into the insect dispenser through the gas port; and a refrigeration system positioned to cool the trough.

Example 22. In this example, there is provided a system for loading insect containers of any of the preceding or subsequent examples, wherein the gas system directs a cooled gas into the insect dispenser.

Example 23. In this example, there is provided a system for loading insect containers of any of the preceding or subsequent examples, wherein the conduit is routed to be cooled by the refrigeration system.

Example 24. In this example, there is provided a system for loading insect containers of any of the preceding or subsequent examples, wherein the gas system directs a knockdown gas into the insect dispenser.

Example 25. In this example, there is provided a system for loading insect containers of any of the preceding or subsequent examples, wherein the gas port of the insect dispenser includes a porous covering defining openings through which the gas flows into the insect dispenser.

Example 26. In this example, there is provided a system for loading insect containers of any of the preceding or subsequent examples, further including a lid covering the trough to enclose the trough, gas system, insect dispenser, and the insect container.

Example 27. In this example, there is provided a system for loading insect containers of any of the preceding or subsequent examples, wherein the refrigeration system maintains the trough at a temperature of less than fifty degrees.

Example 28. In this example, there is provided a system for loading insect containers of any of the preceding or subsequent examples, further including a hanger system coupled to the trough, the hanger system configured to releasably retain the insect dispenser within the trough.

Example 29. In this example, there is provided a system for loading insect containers of any of the preceding or subsequent examples, wherein the refrigeration system maintains the trough at a temperature such that the insects within the insect dispenser transition from a first state to a second state.

Example 30. In this example, there is provided a system for loading insect containers of any of the preceding or subsequent examples, wherein the first state is an active state and the second state is a dormant state.

Example 31. In this example, there is provided a method for loading insect containers, including:

filling an insect dispenser with a plurality of insects, the insects in a first state;

cooling a trough to decrease a temperature within the trough below an ambient temperature;

connecting the insect dispenser to a gas system positioned adjacent the trough;

directing gas into the insect dispenser, the gas affecting the insects within the insect dispenser such that the insects transition to a second state;

positioning an insect container adjacent to a loading port of the insect dispenser within the trough;

opening the loading port of the insect dispenser to release the insects in the second state into the insect container; and sealing the insect container.

Example 32. In this example, there is provided a method for loading insect containers of any of the preceding or subsequent examples, wherein the first state is an active state and the second state is a dormant state.

Example 33. In this example, there is provided a method for loading insect containers of any of the preceding or subsequent examples, wherein the gas is a cooled gas.

Example 34. In this example, there is provided a method for loading insect containers of any of the preceding or subsequent examples, wherein the gas is cooled to a temperature of less than fifty degrees.

Example 35. In this example, there is provided a method for loading insect containers of any of the preceding or subsequent examples, wherein the gas is a knockdown gas.

Example 36. In this example, there is provided a method for loading insect containers of any of the preceding or subsequent examples, wherein the knockdown gas includes carbon dioxide or nitrogen.

Example 37. In this example, there is provided a method for loading insect containers of any of the preceding or subsequent examples, wherein the loading port is positioned at a bottom end of the insect dispenser such that opening the loading port enables the insects to travel, under gravity, into the insect container.

Example 38. In this example, there is provided a method for loading insect containers of any of the preceding or subsequent examples, further including driving insects from the insect dispenser into the insect container with a flow of gas.

Example 39. In this example, there is provided a method for loading insect containers of any of the preceding or subsequent examples, wherein connecting the insect dispenser to the gas system includes connecting a conduit of the gas system to a gas port of the insect container.

Example 40. In this example, there is provided a method for loading insect containers of any of the preceding or subsequent examples, further including driving insects from the insect dispenser through the loading port by introducing a gas into the insect dispenser.

Example 41. In this example, there is provided a method for loading insect containers of any of the preceding or subsequent examples, wherein opening the loading port to release the insects includes opening the insect port at a bottom of the insect dispenser to allow the insects to fall through the loading port into the insect container.

Example 42. In this example, there is provided an insect transportation packaging system, including:

an insulated shipping container including a shipping box with insulation lining interior surfaces of the shipping box;

a pressure vessel removable from the insulated shipping container, the pressure vessel defining a chamber body that encloses a volume within the pressure vessel;

a removable tray with recesses shaped to receive insect transportation containers and to maintain the insect transportation containers in place within the pressure vessel; and an environment management system for detecting environmental conditions within at least one of the pressure vessel or the insulated shipping container during transportation.

Example 43. In this example, there is provided an insect transportation packaging system of any of the preceding or subsequent examples, wherein the chamber body of the pressure vessel is a rigid body and the pressure vessel further includes a lid coupleable to the chamber body to seal the volume within the pressure vessel.

Example 44. In this example, there is provided an insect transportation packaging system of any of the preceding or subsequent examples, wherein the chamber body is a flexible body and the pressure vessel further includes a lid coupleable to the chamber body to seal the volume within the pressure vessel.

Example 45. In this example, there is provided an insect transportation packaging system of any of the preceding or subsequent examples, wherein the environment management system is configured to control the environment conditions and includes a carbon dioxide scrubbing system to reduce a concentration of carbon dioxide within the pressure vessel.

Example 46. In this example, there is provided an insect transportation packaging system of any of the preceding or subsequent examples, wherein the insect transportation containers each comprise:
  a first container portion and a second container portion, the first container portion configured to be coupled to the second container portion to enclose a volume, each of the first and second container portions including:
  a backing plate, wherein:
    the respective backing plate defines a plurality of vent holes providing a conduit for air to travel through the backing plate to provide air to insects stored in the insect container; and
    the respective backing plate is rotatable about a respective axis of rotation perpendicular to the backing plate when engaged with a rotating mechanism at the respective engaging surface to rotate the respective first or second container portion to agitate insects to fall from the first or second container portion when the insect transportation container is in an open configuration; and
  a wall extending from a first surface of the respective backing plate in a direction parallel to the respective axis of rotation, the wall defining a container perimeter and including a non-rotating coupling feature at a distal end of the wall from the backing plate, wherein the backing plate and the wall together define a cavity, and wherein the non-rotating coupling feature of the first container portion and the non-rotating coupling feature of the second container portion enable the first and second container portions to couple together to fully enclose a volume including the cavity and prevent relative rotation of the first and second container portions to prevent damage to insects stored therein.

Example 47. In this example, there is provided an insect transportation packaging system of any of the preceding or subsequent examples, further including a pressurized tank coupled to the pressure vessel through a regulator to maintain a constant pressure within the pressure vessel.

Example 48. In this example, there is provided an insect transportation packaging system of any of the preceding or subsequent examples, wherein the pressurized tank includes a mixture of oxygen and carbon dioxide.

Example 49. In this example, there is provided an insect transportation packaging system of any of the preceding or subsequent examples, wherein the environment management system includes a temperature sensor, a pressure sensor, a vibration sensor, an oxygen sensor, or a carbon dioxide sensor.

Example 50. In this example, there is provided an insect transportation packaging system of any of the preceding or subsequent examples, wherein the environment management system includes a controller configured to actuate an environment adjustment device to alter at least one environmental characteristic within the pressure vessel in response to measurement data from a sensor of the environment management system.

Example 51. In this example, there is provided an insect transportation packaging system of any of the preceding or subsequent examples, further including a refrigeration system to maintain a temperature within the pressure vessel at a predetermined temperature.

Example 52. In this example, there is provided an insect transportation packaging system, including:
  an insulated shipping container including a shipping box with insulation lining interior surfaces of the shipping box;
  a pressure vessel removable from the insulated shipping container, the pressure vessel configured to seal a volume within the pressure vessel;
  a container tray having a perimeter corresponding to an interior of the pressure vessel, the container tray including a set of recesses to receive insect transportation containers and to maintain the insect transportation containers in place within the pressure vessel.

Example 53. In this example, there is provided an insect transportation packaging system of any of the preceding or subsequent examples, further including:
  an environment management system including:
  environment sensors to detect environmental conditions within the volume; and
  environment adjusters to alter the environmental conditions within the volume in response to information from the environment sensors, and wherein the environment sensors comprise at least one of a temperature sensor, a humidity sensor, an oxygen sensor, a carbon dioxide sensor, or a vibration sensor.

Example 54. In this example, there is provided an insect transportation packaging system of any of the preceding or subsequent examples, further including an environment management system including:
  environment sensors to detect environmental conditions within the volume; and
  environment adjusters to alter the environmental conditions within the volume in response to information from the environment sensors, and wherein the environment adjusters comprise an oxygen source configured to introduce oxygen into the pressure vessel and carbon dioxide scrubber configured to remove carbon dioxide from the environment within the volume.

Example 55. In this example, there is provided an insect transportation packaging system of any of the preceding or subsequent examples, wherein the oxygen source is configured to introduce oxygen at a rate to maintain a pressure level within the pressure vessel.

Example 56. In this example, there is provided an insect transportation packaging system of any of the preceding or subsequent examples, wherein the environment sensors comprise an oxygen sensor and the oxygen source is configured to introduce oxygen based at least in part on oxygen level data from the oxygen sensor.

Example 57. In this example, there is provided an insect transportation packaging system of any of the preceding or subsequent examples, wherein the pressure vessel is formed from a flexible material.

Example 58. In this example, there is provided an insect transportation packaging system of any of the preceding or subsequent examples, wherein the insect transportation containers each comprise:
  a first container portion and a second container portion, the first container portion configured to be coupled to the second container portion to enclose a volume, each of the first and second container portions including:
- a backing plate having an engaging surface at a perimeter of the backing plate, wherein:
  - the respective engaging surface defines a set of protrusions extending in a plane defined by the backing plate radially away from a center of the backing plate;
  - the respective backing plate defines a plurality of vent holes providing a conduit for air to travel through the backing plate to provide air to insects stored in the insect container; and
  - the respective backing plate is rotatable about a respective axis of rotation perpendicular to the backing plate when engaged with a rotating mechanism at the respective engaging surface to rotate the respective first or second container portion to agitate insects to fall from the respective first or second container portion when the insect transportation container is in an open configuration; and
- a wall extending from a first surface of the respective backing plate in a direction parallel to the respective axis of rotation, the wall defining a container perimeter and including a non-rotating coupling feature at a distal end of the wall from the backing plate, wherein the backing plate and the wall together define a cavity, and wherein the non-rotating coupling feature of the first container portion and the non-rotating coupling feature of the second container portion enable the first and second container portions to couple together to fully enclose a volume including the cavity and prevent relative rotation of the first and second container portions to prevent damage to insects stored therein.

Example 59. In this example, there is provided a method of packaging insects for transportation, including:
- providing a shipping box, the shipping box lined with insulation on a portion of inner surfaces of the shipping box;
- providing a pressure vessel capable of maintaining an internal pressure against varying external pressures;
- placing an insect transportation container into a recess of a container tray, the container tray sized to fit within an interior of the pressure vessel, the recess shaped to receive the insect transportation container;
- placing the container tray into the interior of the pressure vessel;
- sealing the pressure vessel with the container tray therein;
- placing the pressure vessel within the shipping box; and
- closing the shipping box around the pressure vessel.

Example 60. In this example, there is provided an insect transportation packaging system of any of the preceding or subsequent examples, further including activating an environment monitoring system by at least activating one or more environment sensors to detect environmental characteristics within the pressure vessel.

Example 61. In this example, there is provided an insect transportation packaging system of any of the preceding or subsequent examples, further including placing a carbon dioxide scrubbing system within the pressure vessel.

Example 62. In this example, there is provided an insect transportation packaging system of any of the preceding or subsequent examples, further including activating an environmental adjustment system that adjusts one or more environmental characteristics within the pressure vessel.

Example 63. In this example, there is provided an insect transportation packaging system of any of the preceding or subsequent examples, wherein the environmental adjustment system includes an oxygen introduction system and a carbon dioxide scrubbing system.

Example 64. In this example, there is provided an insect transportation packaging system of any of the preceding or subsequent examples, further including placing a second insect transportation into a second recess of the container tray.

Example 65. In this example, there is provided an insect transportation packaging system of any of the preceding or subsequent examples, wherein sealing the pressure vessel with the container tray therein includes increasing a pressure level within the pressure vessel by introducing a gas including oxygen into the pressure vessel.

Example 66. In this example, there is provided an insect transportation packaging system of any of the preceding or subsequent examples, wherein increasing the pressure level within the pressure vessel includes raising the pressure level by at least three pounds per square inch, and wherein introducing the gas includes introducing the gas via an open end of the pressure vessel or via a valve of the pressure vessel.

Example 67. In this example, there is provided a carbon dioxide scrubbing system for insect transportation within a pressure vessel, including:
- a porous container allowing free exchange of fluid from an interior to an exterior of the porous container and vice versa, the porous container positioned inside the pressure vessel;
- a carbon dioxide scrubbing compound contained within the porous container;
- a gas reservoir tank, the gas reservoir tank filled with a pressurized mixture of oxygen and carbon dioxide; and
- a pressure regulator coupled in-line between the gas reservoir tank and the pressure vessel.

Example 68. In this example, there is provided an insect transportation packaging system of any of the preceding or subsequent examples, wherein the carbon dioxide scrubbing compound includes soda lime.

Example 69. In this example, there is provided an insect transportation packaging system of any of the preceding or subsequent examples, wherein the pressurized mixture of oxygen and carbon dioxide includes a less than twenty-two percent oxygen.

Example 70. In this example, there is provided an insect transportation packaging system of any of the preceding or subsequent examples, wherein the pressure regulator maintains a pressure within the pressure vessel by allowing introduction of the pressurized mixture of oxygen and carbon dioxide and the pressure is maintained at one atmosphere.

Example 71. In this example, there is provided an insect transportation packaging system of any of the preceding or subsequent examples, wherein the carbon dioxide scrubbing compound includes at least one of sodium hydroxide, potassium hydroxide, activated carbon, or lithium hydroxide.

Example 72. In this example, there is provided a method for scrubbing carbon dioxide within a pressure vessel for insect transportation, including:
- providing a pressure vessel to contain insects during transportation at a controlled temperature and pressure;
- providing a carbon dioxide scrubbing compound within the pressure vessel; and
- coupling a gas reservoir to the pressure vessel via a gas regulator, the gas reservoir including a mixture of carbon dioxide and oxygen and the gas regulator configured to introduce gas from the gas reservoir into the pressure vessel in response to a pressure within the pressure vessel dropping below a predetermined threshold.

Example 73. In this example, there is provided an insect transportation packaging system of any of the preceding or subsequent examples, wherein the pressure regulator maintains a predetermined pressure by allowing the mixture of carbon dioxide and oxygen to flow into the pressure vessel when the pressure within the pressure vessel drops below a threshold below the predetermined pressure.

Example 74. In this example, there is provided an insect transportation packaging system of any of the preceding or subsequent examples, further including providing a fan within the pressure vessel to circulate air within the pressure vessel.

Example 75. In this example, there is provided an insect transportation packaging system of any of the preceding or subsequent examples, wherein the carbon dioxide scrubbing compound includes soda lime.

Example 76. In this example, there is provided an insect transportation packaging system of any of the preceding or subsequent examples, wherein the pressurized mixture of oxygen and carbon dioxide includes less than twenty-two percent oxygen.

Example 77. In this example, there is provided a carbon dioxide scrubbing system for insect transportation within a pressure vessel, including:
  a porous container allowing free exchange of fluid from an interior to an exterior of the porous container and vice versa, the porous container positioned inside the pressure vessel;
  a carbon dioxide scrubbing compound contained within the porous container;
  a reservoir of hydrogen peroxide;
  a reaction catalyst; and
  a metering system coupled to the reservoir of hydrogen peroxide to control a flow rate of hydrogen peroxide from the reservoir to the reaction catalyst.

Example 78. In this example, there is provided an insect transportation packaging system of any of the preceding or subsequent examples, wherein the reservoir of hydrogen peroxide includes solid sodium percarbonate and water.

Example 79. In this example, there is provided an insect transportation packaging system of any of the preceding or subsequent examples, wherein the reaction catalyst includes a platinum reactant.

Example 80. In this example, there is provided an insect transportation packaging system of any of the preceding or subsequent examples, wherein the metering system includes a controller configured to control a valve in response to data from an environmental sensor within the pressure vessel.

Example 81. In this example, there is provided an insect transportation packaging system of any of the preceding or subsequent examples, wherein the controller is configured to control the valve in response to data from a pressure sensor within the pressure vessel.

Example 82. In this example, there is provided a method for scrubbing carbon dioxide within a pressure vessel for insect transportation, including:
  providing a pressure vessel to contain insects during transportation at a controlled temperature and pressure;
  providing a carbon dioxide scrubbing compound within the pressure vessel;
  providing an oxygen generation system within the pressure vessel; and
  controlling a metering system of the oxygen generation system to produce oxygen within the pressure vessel to maintain an oxygen level within the pressure vessel as insects consume oxygen.

Example 83. In this example, there is provided an insect transportation packaging system of any of the preceding or subsequent examples, wherein the oxygen generation system includes:
  a reservoir of hydrogen peroxide;
  a reaction catalyst; and
  a metering system coupled to the reservoir of hydrogen peroxide to control a flow rate of hydrogen peroxide from the reservoir to the reaction catalyst.

Example 84. In this example, there is provided an insect transportation packaging system of any of the preceding or subsequent examples, wherein the metering system includes a controller configured to control a valve in response to data from an environmental sensor within the pressure vessel.

Example 85. In this example, there is provided an insect transportation packaging system of any of the preceding or subsequent examples, further including detecting a pressure level within the pressure vessel.

Example 86. In this example, there is provided an insect transportation packaging system of any of the preceding or subsequent examples, wherein the oxygen generation system is configured to release oxygen into the pressure vessel based on the pressure level within the pressure vessel to maintain a constant pressure within the pressure vessel.

Example 87. In this example, there is provided an insect transportation container unloading system, including:
  an insect receiving chamber defining an insect loading opening;
  an insect transportation container unloader coupled to the insect receiving chamber to unload insects from insect transportation containers into the insect receiving chamber through the insect loading opening, the insect transportation container unloader including:
    an insect transportation container dock defining a recess for receiving an insect transportation container and an opening corresponding to the insect loading opening through which insects are loaded into the insect receiving chamber;
    a securing gate coupled to an actuator, the actuator positioned to position the securing gate in a securing position wherein the insect transportation container is retained within the insect transportation container dock and in a free position wherein the insect transportation container is not retained within the insect transportation container dock;
    a clamp coupled to an opening actuator, the opening actuator and clamp positionable to selectively open and close the insect transportation container within the insect transportation container dock;
    an agitation device configured to agitate insect transportation containers positioned within the insect transportation container dock; and
    a gate coupled to a gate actuator, the gate positionable by the gate actuator in:
      a first position wherein the gate seals the insect loading opening; and
      a second position wherein the gate does not seal the insect loading opening.

Example 88. In this example, there is provided an insect transportation container unloading system of any of the preceding or subsequent examples, wherein the agitation device includes a rotary device.

Example 89. In this example, there is provided an insect transportation container unloading system of any of the preceding or subsequent examples, wherein the insect container includes:

a first container portion and a second container portion, the first container portion configured to be coupled to the second container portion to enclose a volume, each of the first and second container portions including:

a backing plate having an engaging surface at a perimeter of the backing plate, wherein:

the respective engaging surface defines a set of protrusions extending in a plane defined by the backing plate radially away from a center of the backing plate;

the respective backing plate defines a plurality of vent holes providing a conduit for air to travel through the backing plate to provide air to insects stored in the insect container; and the respective backing plate is rotatable about a respective axis of rotation perpendicular to the backing plate when engaged with a rotating mechanism at the respective engaging surface to rotate the respective first or second container portion to agitate insects to fall from the respective first or second container portion when the insect transportation container is in an open configuration; and a wall extending from a first surface of the respective backing plate in a direction parallel to the respective axis of rotation, the wall defining a container perimeter and including a non-rotating coupling feature at a distal end of the wall from the backing plate, wherein the backing plate and the wall together define a cavity, and wherein the non-rotating coupling feature of the first container portion and the non-rotating coupling feature of the second container portion enable the first and second container portions to couple together to fully enclose a volume including the cavity and prevent relative rotation of the first and second container portions to prevent damage to insects stored therein.

Example 90. In this example, there is provided an insect transportation container unloading system of any of the preceding or subsequent examples, wherein the agitation device engages with the engaging surface of the insect container.

Example 91. In this example, there is provided an insect transportation container unloading system of any of the preceding or subsequent examples, further including a second insect container unloader coupled to the insect receiving chamber.

Example 92. In this example, there is provided an insect transportation container unloading system of any of the preceding or subsequent examples, wherein the insect receiving chamber releasably couples to an insect release device, the insect release device loadable from the insect receiving chamber with insects for release as part of a sterile insect technique.

Example 93. In this example, there is provided an insect transportation container unloading system, including:

an insect receiving chamber defining an insect loading opening;

an insect transportation container unloader coupled to the insect receiving chamber to unload insects from insect transportation containers into the insect receiving chamber through the insect loading opening, the insect transportation container unloader including:

an insect transportation container dock defining a recess for receiving an insect transportation container and an opening corresponding to the insect loading opening through which insects are loaded into the insect receiving chamber;

an opening actuator, the opening actuator and positionable to selectively open and close the insect transportation container within the insect transportation container dock; and an insect directing system that causes the insects to travel through the insect loading opening after the insect transportation container is opened within the insect transportation container dock.

Example 94. In this example, there is provided an insect transportation container unloading system of any of the preceding or subsequent examples, wherein the insect directing system includes an air nozzle directed between components of the insect transportation container to blow insects out of the insect transportation container.

Example 95. In this example, there is provided an insect transportation container unloading system of any of the preceding or subsequent examples, wherein the insect directing system includes a rotary agitation device that engages with the insect transportation container to rotate the insect transportation container.

Example 96. In this example, there is provided an insect transportation container unloading system of any of the preceding or subsequent examples, further including a second insect transportation container unloader coupled to the insect receiving chamber.

Example 97. In this example, there is provided an insect transportation container unloading system of any of the preceding or subsequent examples, wherein the opening actuator includes a piston that applies a force against one part of the insect transportation container to drive the insect transportation container to open.

Example 98. In this example, there is provided an insect transportation container unloading system of any of the preceding or subsequent examples, wherein the insect transportation container dock has a shape that matches the insect transportation container to receive the insect transportation container and block the insect loading opening.

Example 99. In this example, there is provided an insect transportation container unloading system of any of the preceding or subsequent examples, wherein the insect transportation container includes:

a first container portion and a second container portion, the first container portion configured to be coupled to the second container portion to enclose a volume, each of the first and second container portions including:

a backing plate having an engaging surface at a perimeter of the backing plate, wherein:

the respective engaging surface defines a set of protrusions extending in a plane defined by the backing plate radially away from a center of the backing plate;

the respective backing plate defines a plurality of vent holes providing a conduit for air to travel through the backing plate to provide air to insects stored in the insect container; and the respective backing plate is rotatable about a respective axis of rotation perpendicular to the backing plate when engaged with a rotating mechanism at the respective engaging surface to rotate the respective first or second container portion to agitate insects to fall from the respective first or second container portion when the insect transportation container is in an open configuration; and a wall extending from a first surface of the respective backing plate in a direction parallel to the respective axis of rotation, the wall defining a container perimeter and including a non-rotating coupling feature at a distal end of the wall from the backing plate, wherein the backing plate and the wall together define a cavity, and wherein the non-rotating coupling feature of the first container portion and the non-rotating coupling feature of the second container portion enable the first and second container portions to couple together to fully enclose a volume including the cavity and prevent relative rotation of the first and second container portions to prevent damage to insects stored therein.

Example 100. In this example, there is provided an insect transportation container unloading system of any of the preceding or subsequent examples, wherein the insect directing system includes a rotating device having gear teeth that engage with the engaging surface of the insect transportation container.

Example 101. In this example, there is provided a method, including:
- positioning an insect transportation container in a dock of an insect transportation container unloading system;
- positioning a securing gate in contact with the dock to secure the insect transportation container in the dock;
- separating a first portion and a second portion of the insect transportation container;
- agitating the insect transportation container to release insects from an interior volume of the insect transportation container through an opening in the dock;
- positioning a securing gate to close the opening of the dock;
- coupling the first portion and the second portion of the insect transportation container; and
- positioning the securing gate in an open position to enable removal of the insect transportation container.

Example 102. In this example, there is provided an insect transportation container unloading system of any of the preceding or subsequent examples, wherein agitating the insect transportation container includes directing air through a nozzle at the insect transportation container.

Example 103. In this example, there is provided an insect transportation container unloading system of any of the preceding or subsequent examples, wherein agitating the insect transportation container includes rotating the insect transportation container.

Example 104. In this example, there is provided an insect transportation container unloading system of any of the preceding or subsequent examples, wherein agitating the insect transportation container includes vibrating the insect transportation container.

Example 105. In this example, there is provided an insect transportation container unloading system of any of the preceding or subsequent examples, further including loading insects from the insect transportation container unloading system into an insect release device.

Example 106. In this example, there is provided an insect transportation container unloading system of any of the preceding or subsequent examples, wherein the securing gate includes a "c" shaped cutout that partially surrounds the insect transportation container to enable removal of the insect transportation container when the securing gate is positioned to close the opening of the dock.

While the present subject matter has been described in detail with respect to specific examples thereof, it will be appreciated that those skilled in the art, upon attaining an understanding of the foregoing may readily produce alterations to, variations of, and equivalents to such examples. Accordingly, it should be understood that the present disclosure has been presented for purposes of example rather than limitation, and does not preclude inclusion of such modifications, variations, and/or additions to the present subject matter as would be readily apparent to one of ordinary skill in the art. Indeed, the methods and systems described herein may be embodied in a variety of other forms; furthermore, various omissions, substitutions and changes in the form of the methods and systems described herein may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multipurpose microprocessor-based computing systems accessing stored software that programs or configures the computing system from a general purpose computing apparatus to a specialized computing apparatus implementing one or more examples of the present subject matter. Any suitable programming, scripting, or other type of language or combinations of languages may be used to implement the teachings contained herein in software to be used in programming or configuring a computing device.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included herein are for ease of explanation only and are not meant to be limiting.

The various features and processes described above may be used independently of one another, or may be combined in various ways. All possible combinations and sub-combinations are intended to fall within the scope of the present disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described herein may be configured differently than described. For example, elements may be added to, removed from, or rearranged compared to the disclosed examples.

What is claimed is:

1. An insect container, comprising;
a first container portion and a second container portion, the first container portion configured to be coupled to the second container portion to enclose a volume, each of the first and second container portions comprising:
a backing plate, wherein:
the respective backing plate defines a plurality of vent holes providing a conduit for air to travel through the backing plate to provide air to insects when the insects are stored in the insect container; and
the respective backing plate is rotatable about a respective axis of rotation perpendicular to the backing plate when the insect container is in an open configuration; and
a wall extending from a first surface of the respective backing plate in a direction parallel to the respective axis of rotation, the wall defining a container perimeter and including a non-rotating coupling feature at a distal end of the wall from the backing plate, wherein:
the backing plate and the wall together define a cavity;
the non-rotating coupling feature of the first container portion comprises a continuous perimeter of male interfaces or a continuous perimeter of female interfaces;
the non-rotating coupling feature of the second container portion comprises a continuous perimeter of corresponding female interfaces or a continuous perimeter of corresponding male interfaces; and
the non-rotating coupling feature of the first container portion and the non-rotating coupling feature of the second container portion enable the first and second container portions to couple together to fully enclose a volume comprising the cavity and prevent relative rotation of the first and second container portions.

2. The insect container of claim 1, wherein each of the plurality of vent holes have a cross-sectional dimension less than a size of representative insect to be stored inside the insect container.

3. The insect container of claim 1, wherein each backing plate comprises an engaging surface at a perimeter of the respective backing plate, and wherein the respective engaging surface defines a set of protrusions extending in a plane defined by the backing plate radially away from a center of the backing plate, and wherein the set of protrusions are configured to engage with a rotating mechanism at the respective engaging surface to rotate the respective first or second container portion.

4. The insect container of claim 3, wherein the set of protrusions comprises gear teeth around the perimeter of the respective backing plate, and wherein each respective backing plate is circular.

5. The insect container of claim 1, wherein the container perimeter forms a circular shape and wherein the container perimeter is concentric with the perimeter of the backing plate.

6. The insect container of claim 1, wherein the container perimeter has a first diameter and the backing plate has a second diameter, the first diameter smaller than the second diameter.

7. The insect container of claim 1, wherein at least one of the first container portion or the second container portion comprises a compressible foam insert.

8. The insect container of claim 7, wherein the compressible foam insert comprises an inner portion and an outer portion, the inner portion concentric with the outer portion with the inner portion having a first height and the outer portion having a second height, the second height greater than the first height.

9. The insect container of claim 1, wherein:
the continuous perimeter of male interfaces or the continuous perimeter of female interfaces of the non-rotating coupling feature of the first container portion are first scalloped surfaces; and
the continuous perimeter of corresponding female interfaces or the continuous perimeter of corresponding male interfaces of the non-rotating coupling feature of the second container portion are second scalloped surfaces.

10. An insect container, comprising;
a first container portion, comprising:
a first circular backing plate; and
a first raised wall extending from a first surface of the first circular backing plate, an edge of the first raised wall opposite the first circular backing plate including a first profile comprising a continuous perimeter of male interfaces or a continuous perimeter of female interfaces;
a second container portion, comprising:
a second circular backing plate; and
a second raised wall extending from a second surface of the second circular backing plate, an edge of the second raised wall opposite the second backing plate including a second profile comprising a continuous perimeter of corresponding female interfaces or a continuous perimeter of corresponding male interfaces, wherein the first profile and the second profile mate together to:
releasably interlock the first container portion and the second container portion; and
prevent rotation of the first container portion with respect to the second container portion; and
wherein the first container portion and the second container portion define an interior volume configured to retain a population of insects when interlocked with each other.

11. The insect container of claim 10, wherein each of the first circular backing plate and the second circular backing plate comprise teeth formed around respective perimeters thereof, and wherein the teeth formed in the first circular backing plate and the second circular backing plate each comprise a series of gear teeth that enable rotation of the first circular backing plate and the second circular backing plate when engaged with a rotating mechanism having mating teeth.

12. The insect container of claim 10, wherein the first profile and the second profile each comprise a scalloped profile.

13. The insect container of claim 10, wherein the first profile comprises a male connector and the second profile comprises a female connector, wherein the male connector and the female connector releasably couple together to secure the first container portion and the second container portion together.

14. The insect container of claim 10, further comprising a retaining device comprising a flexible band to maintain the first container portion and the second container portion in contact with one another along the edge of the first raised wall and the second raised wall, respectively.

15. The insect container of claim 10, further comprising a foam insert, wherein an outer perimeter of the foam insert matches an inner perimeter of the first raised wall of the first container portion, and wherein the foam insert comprises a raised edge around the outer perimeter of the foam insert such that the foam insert defines an insect support cavity.

16. The insect container of claim 10, wherein the first circular backing plate and the second circular backing plate each define a plurality of vent holes providing a conduit between the first surface and a second third surface of the first circular backing plate and the second surface and a fourth surface of the second circular backing plate.

17. The insect container of claim 16, wherein the vent holes each have a cross-sectional dimension less than a cephalothorax diameter of an insect.

18. The insect container of claim 10, wherein each of the first circular backing plate and the second circular backing plate comprise teeth formed around respective perimeters thereof, and wherein the teeth of the first circular backing plate and the teeth of the second circular backing plate extend beyond an outer perimeter of the first raised wall and the second raised wall, respectively.

* * * * *